(12) United States Patent
Hayakawa et al.

(10) Patent No.: US 6,180,560 B1
(45) Date of Patent: Jan. 30, 2001

(54) THERMOSENSITIVE RECORDING MATERIAL AND COLOR DEVELOPER COMPOUND THEREFOR

(75) Inventors: Kunio Hayakawa; Mitsunobu Morita, both of Shizuoka (JP)

(73) Assignee: Ricoh Company, Ltd., Tokyo (JP)

( * ) Notice: Under 35 U.S.C. 154(b), the term of this patent shall be extended for 0 days.

(21) Appl. No.: 09/134,689

(22) Filed: Aug. 14, 1998

(30) Foreign Application Priority Data

| Aug. 14, 1997 | (JP) | 9-233381 |
| Nov. 10, 1997 | (JP) | 9-323851 |
| Nov. 10, 1997 | (JP) | 9-323852 |
| Nov. 19, 1997 | (JP) | 9-335141 |
| Nov. 19, 1997 | (JP) | 9-335142 |
| Nov. 27, 1997 | (JP) | 9-344162 |
| Dec. 9, 1997 | (JP) | 9-356211 |
| Dec. 18, 1997 | (JP) | 9-364686 |
| Dec. 18, 1997 | (JP) | 9-364687 |
| Feb. 9, 1998 | (JP) | 10-042936 |
| Mar. 27, 1998 | (JP) | 10-098156 |
| May 18, 1998 | (JP) | 10-153632 |

(51) Int. Cl.⁷ .................................................. B41M 5/30
(52) U.S. Cl. ........................... 503/216; 503/200; 503/226
(58) Field of Search ................................. 503/216, 217, 503/225, 200, 226

(56) References Cited

U.S. PATENT DOCUMENTS

| 4,140,862 | 2/1979 | Dotson, Jr. et al. | 560/83 |
| 5,306,687 | 4/1994 | Furuya et al. | 503/207 |
| 5,447,900 | 9/1995 | Suzaki et al. | 503/207 |
| 5,489,501 | 2/1996 | Torii et al. | 430/341 |

FOREIGN PATENT DOCUMENTS

| 631783 | 6/1936 | (DE) . |
| 2088889 | * 6/1982 | (GB) . |
| 9267566 | 10/1997 | (JP) . |

OTHER PUBLICATIONS

Lustig; Chemische Berichte, vol. 28, 1895, p. 2992, line 5.

V. Braun: Chemische Berichte, vol. 37, 1904, p. 3586, lines 12–13.

V. Braun: Chemische Berichte, vol. 42, 1909, p. 4551, line 31.

Ball et al., "Calcium ionophores as cardiac stimulants," Eur.J. Med. Chem.Chim.Ther.;Vol. 20,No. 2,1985, pp.137–143.

Drewes et al., "Synthesis of new macrocycles, Part IV. Two–step synthesis of dimeric phthalic esters." J.Chem. Soc. Perkin Trans. 1,1974,pp.2578–2580.

* cited by examiner

*Primary Examiner*—Bruce H. Hess
(74) *Attorney, Agent, or Firm*—Cooper & Dunham LLP

(57) ABSTRACT

A thermosensitive recording material has a support and a thermosensitive coloring layer formed thereon containing a leuco dye and a color developer capable of inducing color formation in the leuco dye upon application of heat thereto, with the color developer including at least one compound (A) having in a molecule thereof at least two aromatic ring moieties with specific structures, selected from the group consisting of an aromatic ring moiety having at least one carboxyl group and electron-attracting functional group, an aromatic ring moiety having at least one carboxyl group and electron-donating functional group, and an aromatic ring moiety having at least one carboxyl group, free of the electron-attracting and electron-donating functional groups. An aromatic carboxylic acid compound serving as the above-mentioned compound (A) and the producing method thereof are also disclosed.

23 Claims, 19 Drawing Sheets

THERMOSENSITIVE RECORDING MATERIAL AND COLOR DEVELOPER COMPOUND THEREFOR

BACKGROUND OF THE INVENTION

1. Field of the Invention

The present invention relates to a thermosensitive recording material comprising as the main components a leuco dye serving as a coloring agent and a color developer capable of inducing color formation in the leuco dye upon application of heat thereto. In addition, the present invention also relates to an aromatic carboxylic acid compound useful as the color developer for use in the thermosensitive recording material, and the production method of the above-mentioned compound.

2. Discussion of Background

Generally, a thermosensitive recording material comprises a support and a thermosensitive coloring layer formed thereon, which comprises as the main components a colorless or light colored electron-donating dye precursor, and an electron-accepting color developer. These dye precursor and color developer are caused to react instantaneously upon the application of heat thereto to produce recorded images, for instance, using a thermal head, heat pen or laser beam, as disclosed in Japanese Patent Publications 43-4160 and 45-14039.

A thermosensitive recording material is used in a wide variety of fields, for example, as the recording material for an electronic computer, facsimile apparatus, ticket vending apparatus, label printer, and recorder because it has the advantages that recording can be achieved using a relatively simple apparatus, maintenance is simple, and there is no noise development.

The above-mentioned thermosensitive recording material employing such an electron-donating dye precursor and an electron-accepting color developer has excellent characteristics such as good appearance and nice touch and is capable of producing images with high coloring density, but also has the disadvantage that the image preservability thereof is poor. To be more specific, when image areas formed in the thermosensitive recording material come in contact with plastics such as polyvinyl chloride, images are decolorized by plasticizers and additives contained in such plastics, or when the image areas come in contact with chemicals contained in foods or cosmetics, such image areas are easily decolorized or the background is easily colored.

To improve the preservation stability of the image recorded in the thermosensitive recording material, it is proposed to use color developers with high reliability. For instance, the use of a phenolsulfone compound as the color developer is disclosed in Japanese Laid-Open Patent Applications 58-82788 and 60-13852; a metallic salt of benzoic acid, disclosed in Japanese Laid-Open Patent Application 61-47292; and a substituted salicylic acid compound, disclosed in Japanese Laid-Open Patent Application 62-169681. However, even though the aforementioned compounds are used as the color developers, the fastness to plasticizers of the image areas formed in the thermosensitive recording material is not sufficient.

Furthermore, the use of a monoester of nitrophthalic acid is proposed in Japanese Laid-Open Patent Application 62-80089, but this compound is unsatisfactory in terms of the fastness to plasticizers of the image areas formed in the thermosensitive recording material. In addition, a sulfonylurea-group-containing compound is used as the color developer in Japanese Laid-Open Patent Application 6-255262. When this type of compound is used as the color developer, the coloring sensitivity extremely deteriorates although the fastness to plasticizers of the image area is improved.

In Japanese Laid-Open Patent Application 9-267566, it is proposed to use as the color developer a compound excluded in the present invention, that is, a compound (B) as will be described in detail later, and metallic salts thereof. However, these compounds have the shortcomings that the image area formed in the thermosensitive recording material is readily decolorized under the circumstances of high temperature.

By the way, it is believed that synthesis of a nitrophthalamide dimer, in particular, a 3-nitrophthalamide dimer can be achieved by amidation reaction of 3-nitrophthalic acid by use of an amine compound. A reaction between 3-nitrophthalic anhydride and an amine compound is reported, for example, in IDDIAN J. CHEM., VOL. 7, 634–635 (1969) and J. Am. Chem. Soc., Vol. 57, 1064–1065 (1935). According to those references, as shown in the following reaction schemes (1) and (2), the amidation reaction of 3-nitrophthalic anhydride takes place at the 1-position of 3-nitrophthalic acid due to steric hindrance when an aromatic primary amine such as aniline is used as the amine compound; while the amidation reaction is carried out at the 2-position thereof when ammonium is used as the amine compound because this reaction is less subjected to steric hindrance.

[Reaction Schemes]

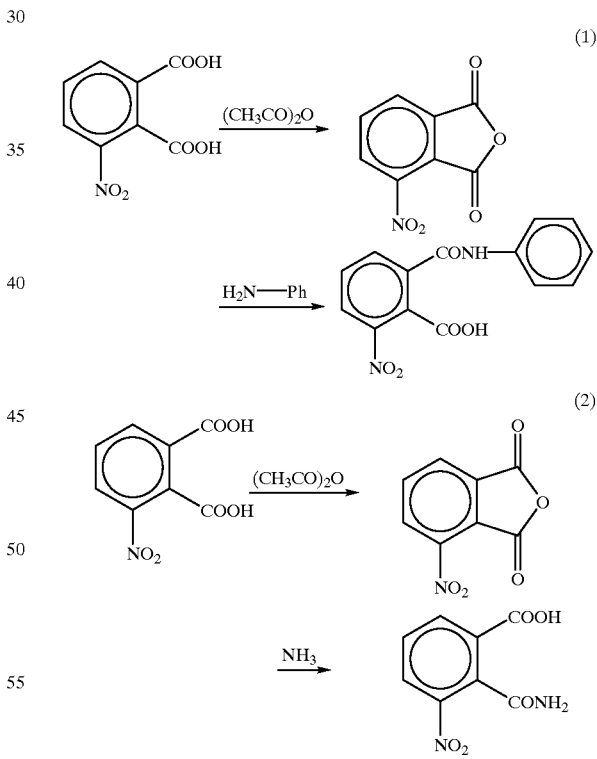

It is considered that the difference in reactivity as shown in the reaction schemes (1) and (2) results from the steric hindrance caused when carbonyl group in 3-nitrophthalic anhydride is attacked by an amine compound.

When 3-nitrophthalamide dimers of the following formulas (V) and (VI) were separately synthesized by allowing 3-nitrophthalic anhydride to react with a diamine compound under the same conditions as stated in the aforementioned references, there was obtained a mixture of the isomers of formulas (V) and (VI).

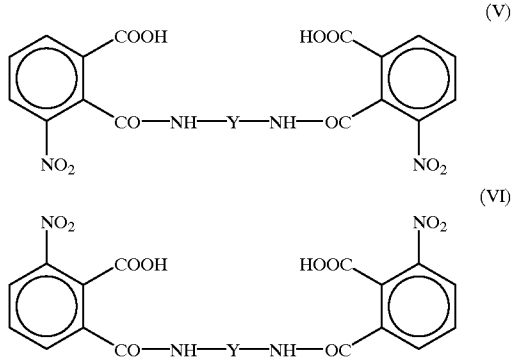

wherein Y represents, for example, an alkylene group having 2 to 12 carbon atoms, a xylylene group, In this case, although those two 3-nitrophthalamide dimers (V) and (VI) can be isolated from each other, each compound cannot be efficiently obtained as a pure product because the separation is very difficult.

Further, the aforementioned 3-nitrophthalamide dimers (V) and (VI) can be independently synthesized in accordance with the following reaction schemes (3) and (4):

[Reaction Schemes]

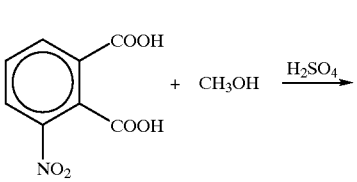

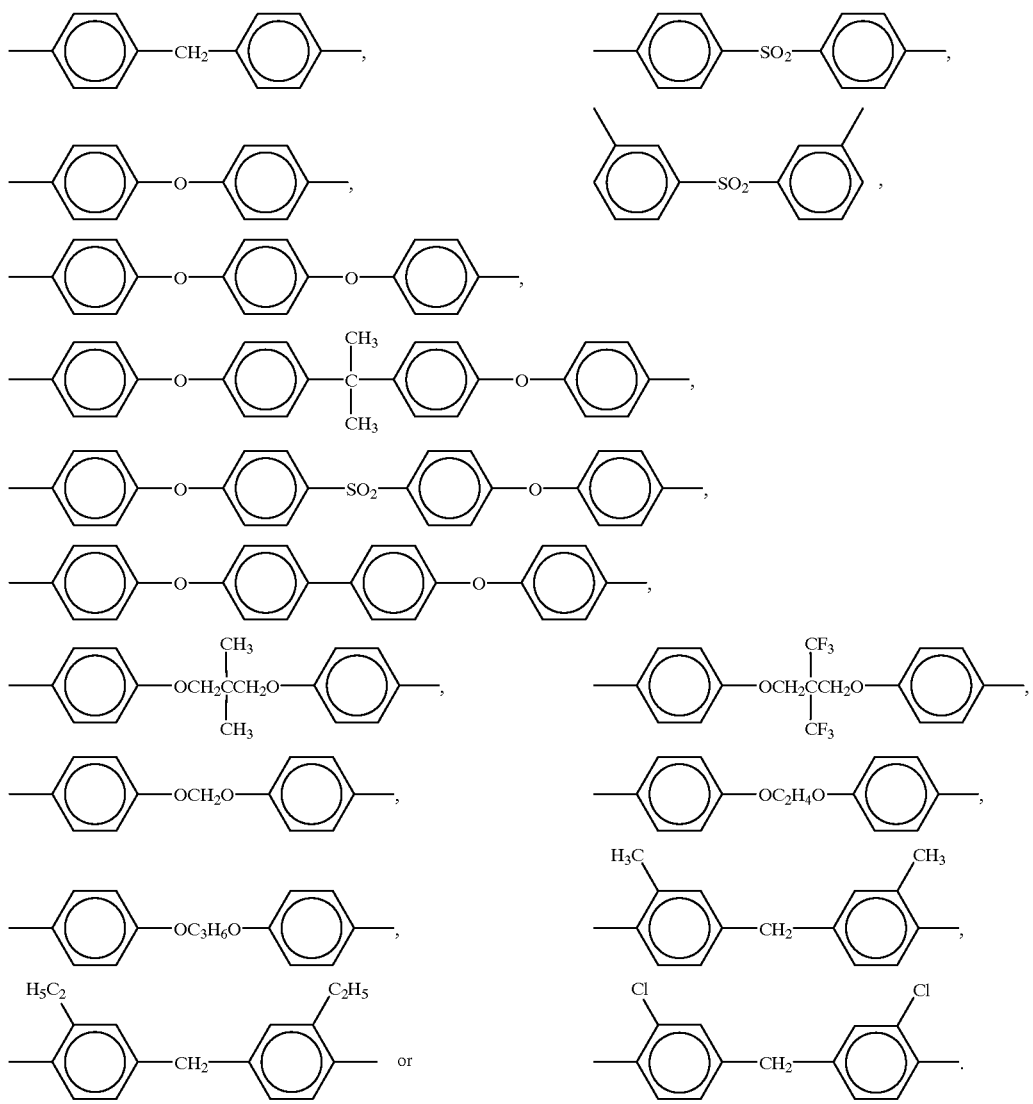

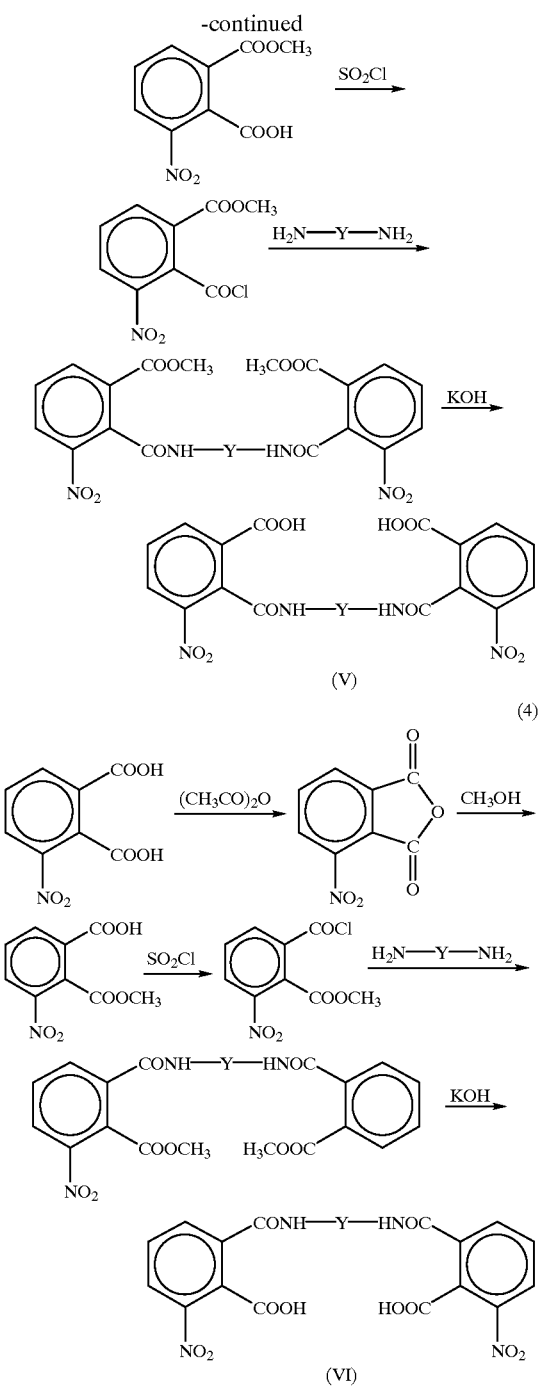

However, the above-mentioned reaction schemes (3) and (4) are very long and include complicated reaction steps, so that they are not practical. There is increasing a demand for the establishment of efficient synthesis method.

SUMMARY OF THE INVENTION

Accordingly, a first object of the present invention is to provide a thermosensitive recording material capable of producing recorded images therein which images are superior in preservation stability, in particular, the oil resistance, the plasticizer resistance, and the heat resistance.

A second object of the present invention is to provide an aromatic carboxylic acid compound which is useful as the color developer, when used in the thermosensitive recording material, capable of producing recorded images with improved preservation stability.

A third object of the present invention is to provide a method of producing the above-mentioned aromatic carboxylic acid compound, in particular, a 3-nitrophthalamide dimer, in the form of a pure product without including the isomers thereof.

The above-mentioned first object of the present invention can be achieved by a thermosensitive recording material comprising a support and a thermosensitive coloring layer formed thereon comprising a leuco dye and a color developer capable of inducing color formation in the leuco dye upon application of heat thereto, with the color developer comprising at least one compound (A) having in a molecule thereof at least two aromatic ring moieties selected from the group consisting of (i) an aromatic ring moiety having at least one carboxyl group and at least one electron-attracting functional group, (ii) an aromatic ring moiety having at least one carboxyl group and at least one electron-donating functional group, and (iii) an aromatic ring moiety having at least one carboxyl group, free of the electron-attracting functional group and the electron-donating functional group, provided that from compounds having two of the aromatic ring moieties (iii) serving as the compound (A), a compound of the following formula (B) is excluded:

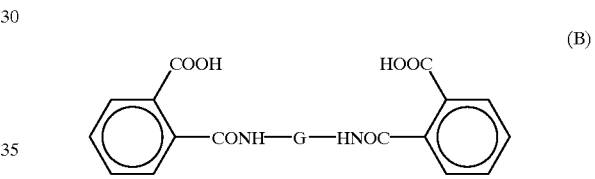

wherein G is —$C_nH_{2n-2}$— (in which n is an integer of 2 to 6),

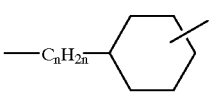

(in which n is an integer of 2 to 6),

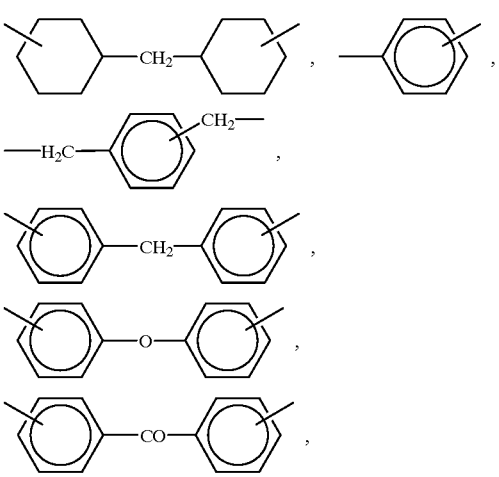

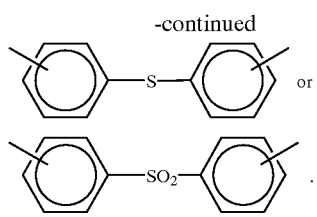

In the thermosensitive recording material of the present invention, it is preferable that at least two of the aromatic ring moieties for use in the compound (A) be bonded by ester linkage or amide linkage, and that the aromatic ring moieties in the molecule be different.

Further, it is preferable that the above-mentioned electron-attracting functional group be selected from the group consisting of nitro group and ester group, and that the electron-donating functional group be selected from the group consisting of hydroxyl group, alkoxyl group and sulfonyloxy group.

In addition, the thermosensitive recording material may further comprise an intermediate layer, which is provided between the support and the thermosensitive coloring layer and comprises minute spherical void particles comprising a thermoplastic resin.

The second object of the present invention can be achieved by an aromatic carboxylic acid compound of formula (I):

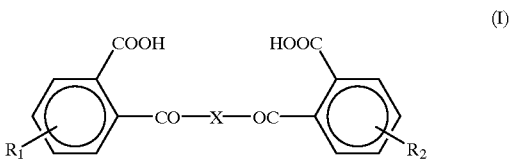

wherein $R^1$ and $R^2$ optionally are the same or different and are each a hydrogen atom, nitro group, hydroxyl group, an alkoxyl group, sulfonyloxy group, an alkyl group, an aralkyl group, an aryl group, an alkyloxycarbonyl group, an aralkyloxycarbonyl group or an aryloxycarbonyl group; and X is —NHYHN— group or —OZO— group, in which Y is an alkylene group having 2 to 12 carbon atoms, a xylylene group,

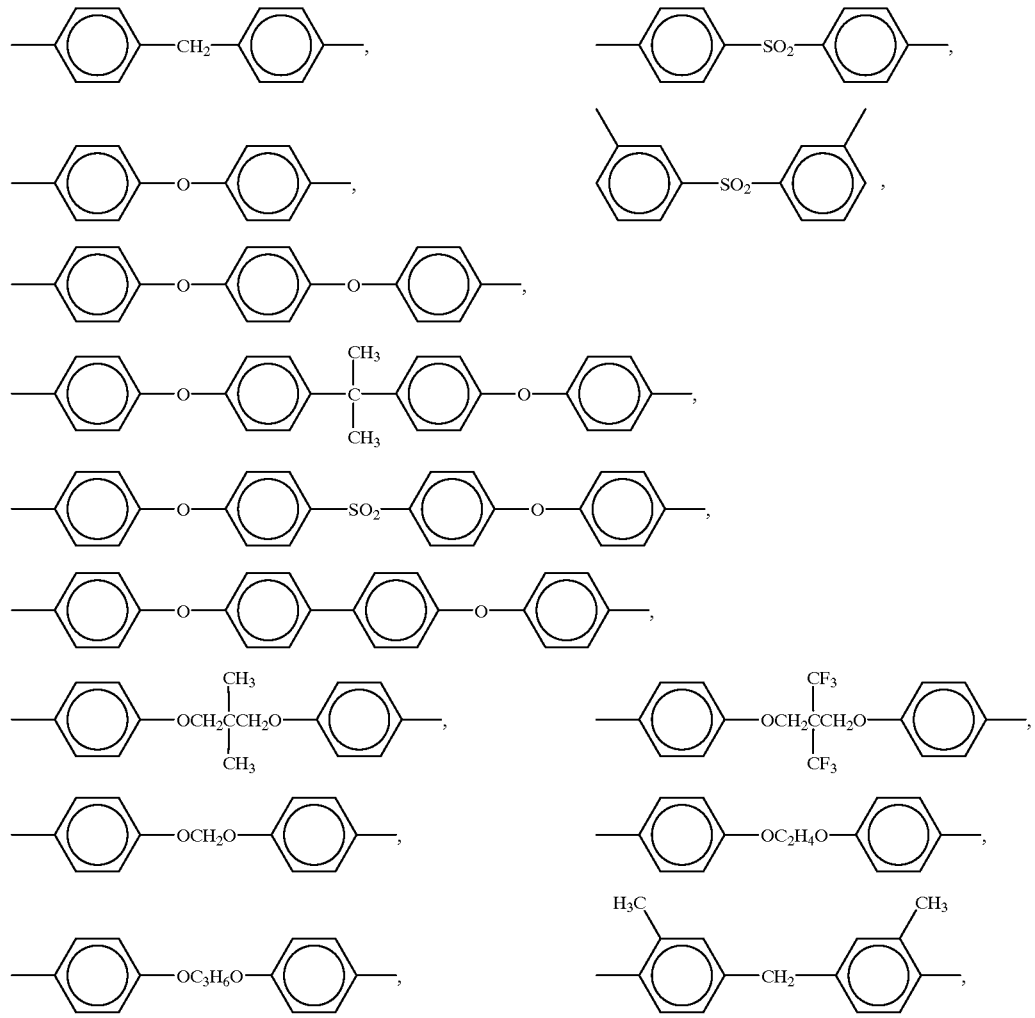

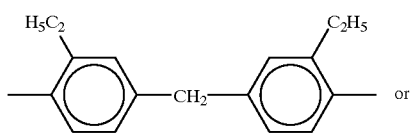 or 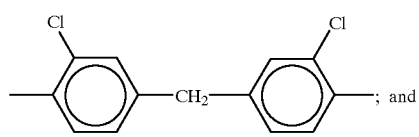 ; and

Z is an alkylene group having 2 to 12 carbon atoms, a xylylene group, an oxalkylene group, a bisoxalkylene group, a trioxalkylene group,

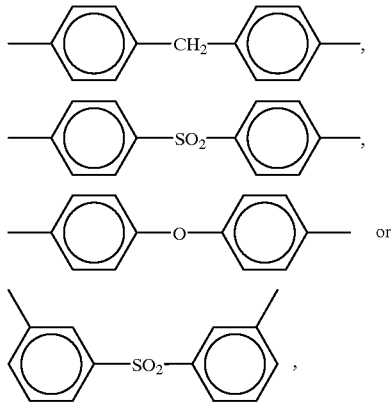

provided that when $R^1$ and $R^2$ are each hydrogen atom, X is not —NHYHN— group in which Y represents an alkylene group having 2 to 12 carbon atoms, a xylylene group,

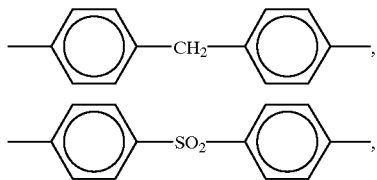

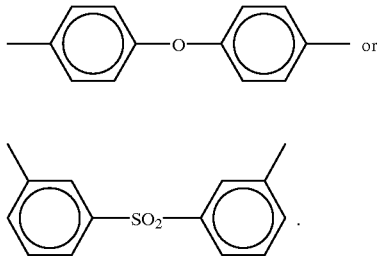

The third object of the present invention can be achieved by a method of producing an aromatic carboxylic acid compound of formula (I'):

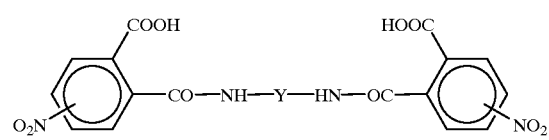

(I')

wherein Y is an alkylene group having 2 to 12 carbon atoms, a xylylene group,

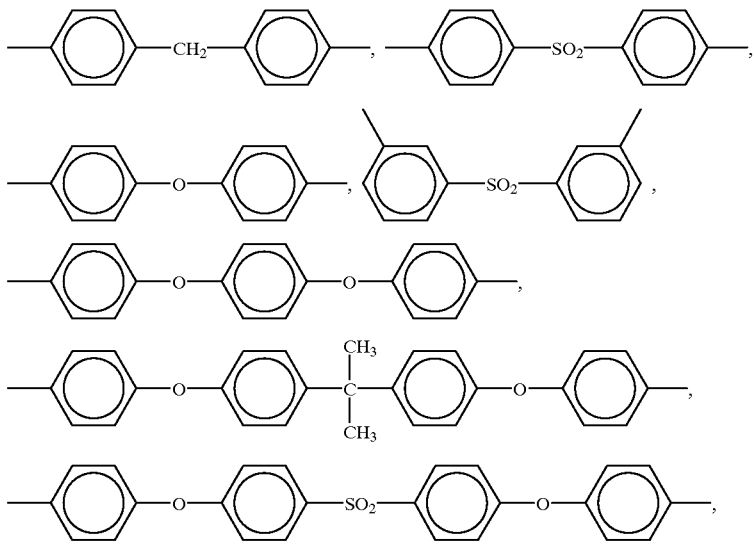

-continued

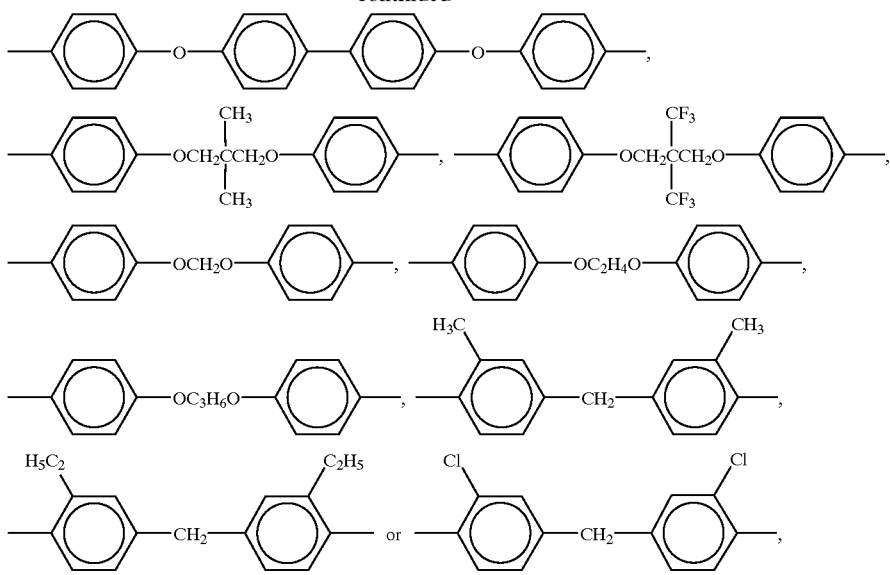

comprising the step of allowing a nitrophthalic anhydride of formula (II) to react with a compound of formula (III):

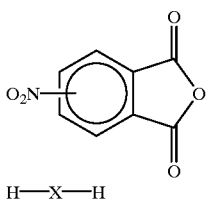

(II)

(III)

H—X—H wherein X is —NHYHN— group in which Y is the same as that previously defined.

Further, the third object of the present invention can be achieved by a method of producing an aromatic carboxylic acid compound of formula (V):

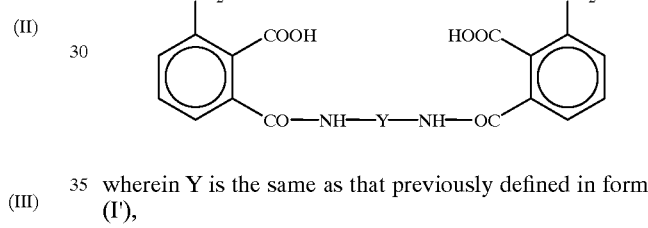

(V)

wherein Y is the same as that previously defined in formula (I'), comprising the step of allowing 3-nitrophthalic anhydride to react with a diamine compound of formula (IV) using a reaction solvent selected from the group consisting of acetic acid, tetrahydrofuran and nitrobenzene:

$H_2N—Y—NH_2$ (IV)

wherein Y is the same as that previously defined.

Furthermore, the third object of the present invention can also be achieved by a method of producing an aromatic carboxylic acid compound of formula (VI):

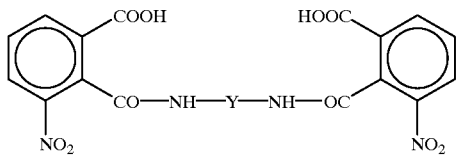

(VI)

wherein Y is the same as that previously defined in formula (I'), comprising the steps of dissolving 3-nitrophthalic anhydride in acetic anhydride to prepare an acetic anhydride solution of 3-nitrophthalic anhydride, and adding a diamine compound of formula (IV) in small portions to the acetic anhydride solution of 3-nitrophthalic anhydride so as to dissolve the diamine compound in the acetic anhydride solution:

$H_2N—Y—NH_2$ (IV)

wherein Y is the same as that previously defined.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
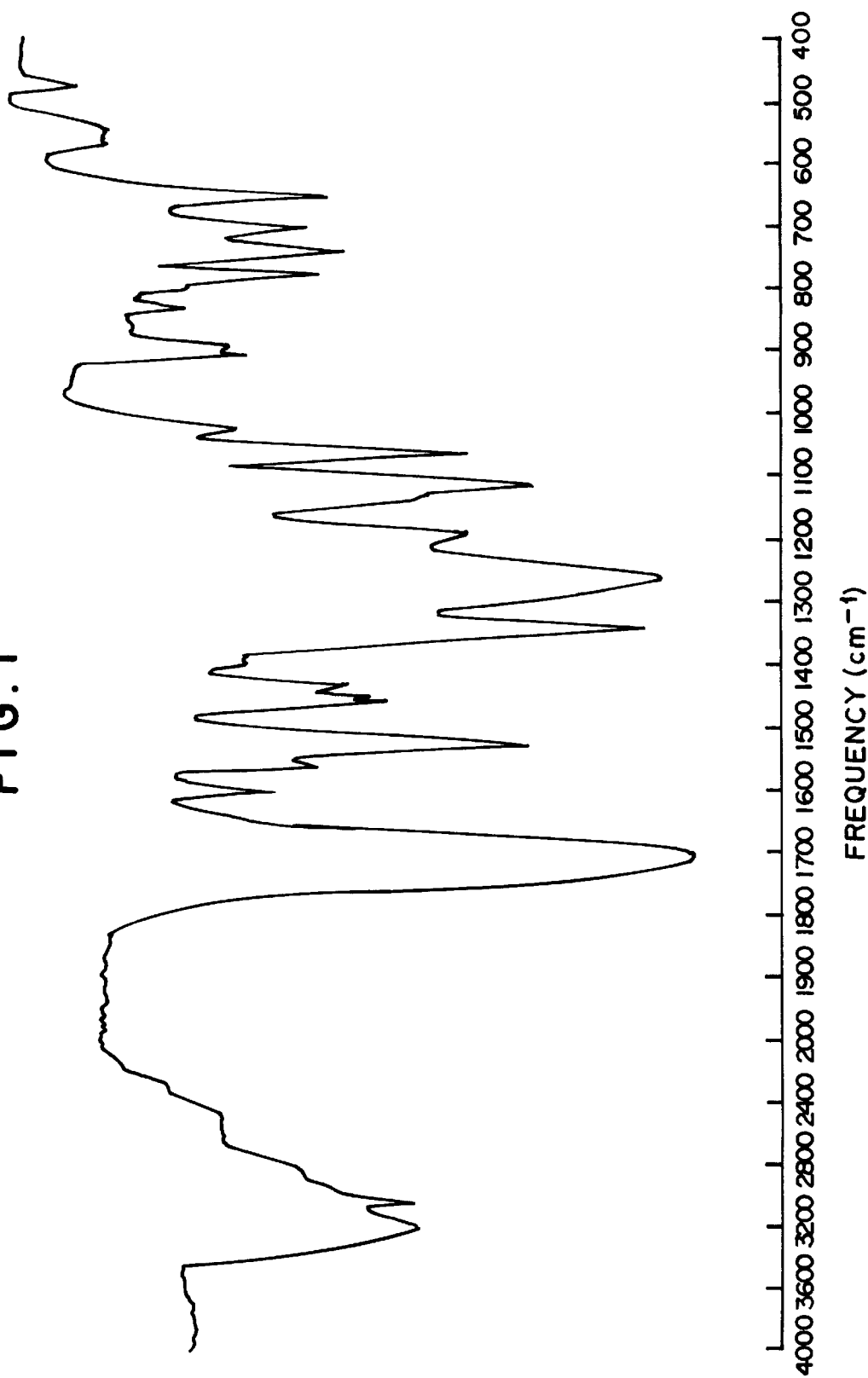
FIG. 1 is an IR spectrum of a compound No. 1 obtained in Preparation Example 1.

The thermosensitive recording material of the present invention comprises as the color developer at least one compound (A) having in a molecule thereof at least two aromatic ring moieties selected from the group consisting of:

(i) an aromatic ring moiety having at least one carboxyl group and at least one electron-attracting functional group, (ii) an aromatic ring moiety having at least one carboxyl group and at least one electron-donating functional group, and (iii) an aromatic ring moiety, having at least one carboxyl group, free of the electron-attracting functional group and the electron-donating functional group,
provided that from compounds having two of the aromatic ring moieties (iii) serving as the compound (A), a compound of formula (B) is excluded:

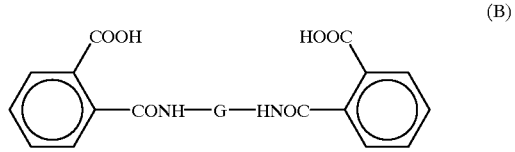

(B)

wherein G is —$C_nH_{2n-2}$— (in which n is an integer of 2 to 6),

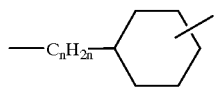

(in which n is an integer of 2 to 6),

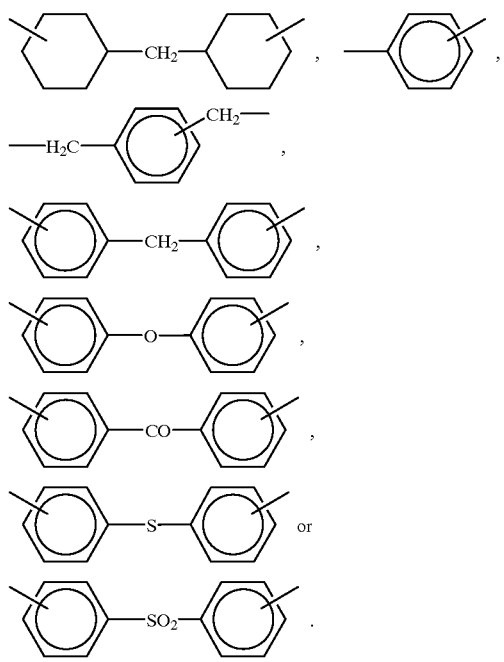

Examples of the above-mentioned compound (A) include a compound represented by the following formula (VII):

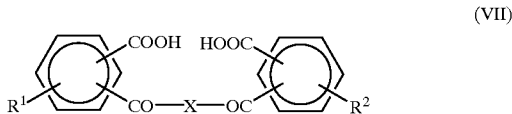

(VII)

wherein $R^1$ and $R^2$ optionally are the same or different and are each a hydrogen atom, nitro group, a halogen atom, cyano group, carbonyl group, sulfonyl group, hydroxyl group, an alkoxyl group, sulfonyloxy group, an alkyl group, an aralkyl group, an aryl group, an alkyloxycarbonyl group, an aralkyloxycarbonyl group, or an aryloxycarbonyl group; and X is —NHYHN— group or —OYO— group,
in which Y is a bivalent group derived from an aliphatic hydrocarbon, a bivalent group derived from an aliphatic hydrocarbon which has at least one hetero atom, carbonyl group, sulfonyl group, ester linkage and aromatic ring in the main chain thereof, or a bivalent group derived from bivalent aromatic hydrocarbons which are bonded by at least one hetero atom, carbonyl group, sulfonyl group, ester linkage, alkylene, or an aliphatic hydrocarbon including a hetero atom in the main chain thereof.

Specific examples of Y include an alkylene having 1 to 8 carbon atoms, an oxalkylene, a bisoxalkylene, a trisoxalkylene, xylylene, phenylene, biphenylene, naphthylene, and a bivalent group represented by the following formula:

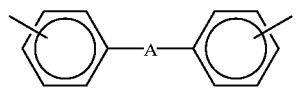

wherein A represents an alkylene group which may have ester group, sulfonyl group, or ether linkage.

To be more specific, Y represents the following groups;
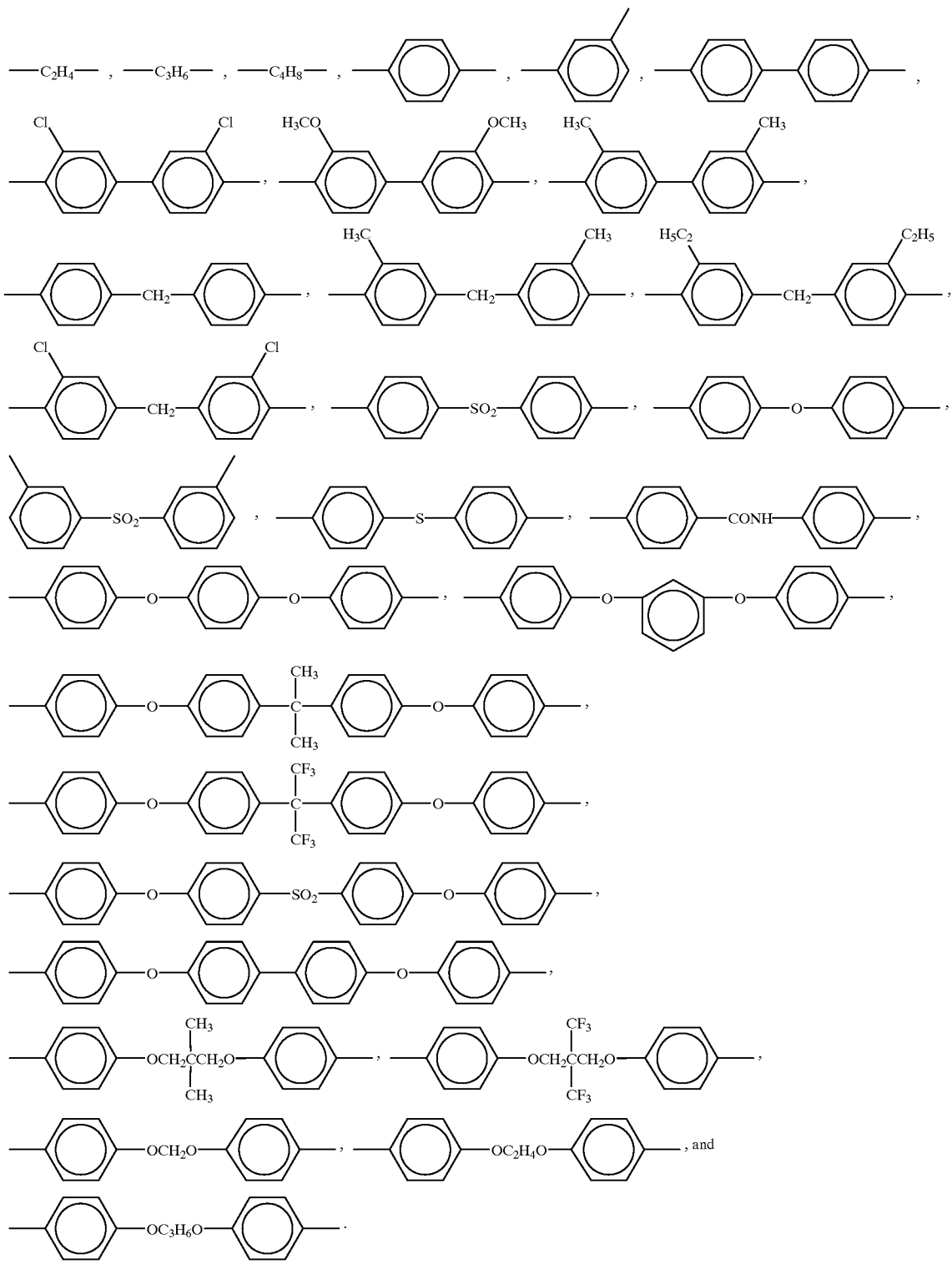
In the formula (VII), $R^1$ and $R^2$ may be different in the molecule thereof, as mentioned above.
In the present invention, as the compound (A) represented by formula (VII), a compound of the following formula (I) is preferable:

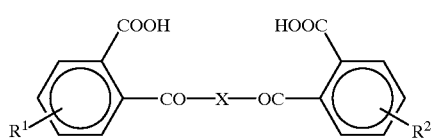
(I)
wherein $R^1$, $R^2$ and X are the same as those previously defined, provided that when $R^1$ and $R^2$ are each a hydrogen atom, X is not —NHYHN— group in which Y represents $C_nH_{2n-2}$ (in which n is an integer of 2 to 6),
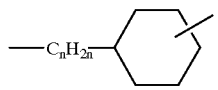
(in which n is an integer of 2 to 6),
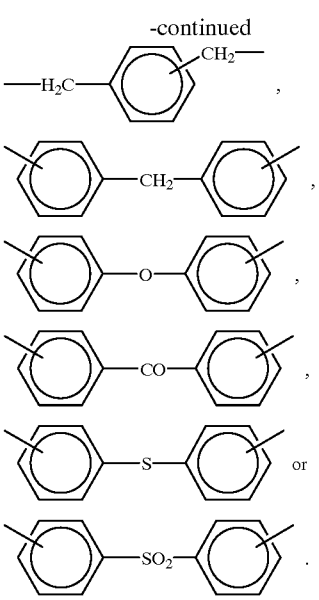
Specific examples of the compound represented by formula (I) are shown below.

TABLE 1
| Compound No. | Structure |
|---|---|
| 1 | 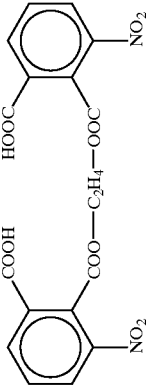 |
| 2 | 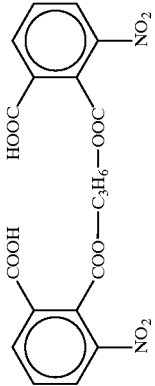 |
| 3 | 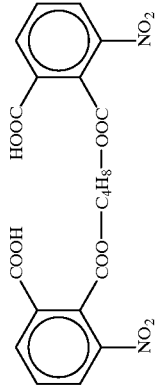 |
| 4 | 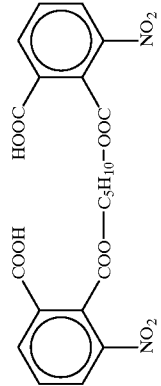 |
| 5 | 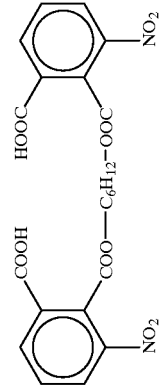 |

TABLE 1-continued

| Compound No. | Structure |
|---|---|
| 6 | (structure) |
| 7 | (structure) |
| 8 | (structure) |
| 9 | (structure) |
| 10 | (structure) |
| 11 | (structure) |

TABLE 1-continued

| Compound No. | Structure |
|---|---|
| 12 | HOOC-C6H3(NO2)-COO-C2H4OC2H4OC2H4-OOC-C6H3(NO2)-COOH |
| 13 | HOOC-C6H3(NO2)-COO-C2H4OC2H4OC2H4OC2H4-OOC-C6H3(NO2)-COOH |
| 14 | HOOC-C6H3(NO2)-COO-CH2-C(CH3)2-CH2-OOC-C6H3(NO2)-COOH |
| 15 | HOOC-C6H3(NO2)-COO-CH2-C6H4-CH2-OOC-C6H3(NO2)-COOH |
| 16 | HOOC-C6H3(NO2)-COO-C6H4-OOC-C6H3(NO2)-COOH |

TABLE 1-continued

| Compound No. | Structure |
|---|---|
| 17 | HOOC-C6H3(NO2)-O-CO-C6H4-C6H4-OOC-C6H3(NO2)-COOH |
| 18 | HOOC-C6H3(NO2)-OOC-C10H4-COO-C6H3(NO2)-COOH |
| 19 | HOOC-C6H3(NO2)-CO-NH-C2H4-NH-OC-C6H3(NO2)-COOH |
| 20 | HOOC-C6H3(NO2)-CO-NH-C2H4-NH-OC-C6H3(NO2)-COOH |
| 21 | HOOC-C6H3(NO2)-CO-NH-C4H8-NH-OC-C6H3(NO2)-COOH |

TABLE 1-continued

| Compound No. | Structure |
|---|---|
| 22 | HOOC-C6H3(NO2)-CO-NH-C6H12-NH-CO-C6H3(NO2)-COOH |
| 23 | HOOC-C6H3(NO2)-CONH-C6H4-SO2-C6H4-HNOC-C6H3(NO2)-COOH |
| 24 | HOOC-C6H3(NO2)-CO-NH-C6H4-NH-CO-C6H3(NO2)-COOH |
| 25 | HOOC-C6H3(NO2)-CO-NH-CH2-C6H4-CH2-NH-CO-C6H3(NO2)-COOH |
| 26 | HOOC-C6H3(NO2)-CO-NH-C6H4-CH2-C6H4-NH-CO-C6H3(NO2)-COOH |

TABLE 1-continued

| Compound No. | Structure |
|---|---|
| 27 | HOOC-C₆H₃(NO₂)-CO-NH-C₆H₄-O-C₆H₄-NH-CO-C₆H₃(NO₂)-COOH |
| 28 | HOOC-C₆H₃(NO₂)-CO-NH-C₆H₄-SO₂-C₆H₄-NH-CO-C₆H₃(NO₂)-COOH |
| 29 | HOOC-C₆H₃(NO₂)-COO-C₂H₄-OOC-C₆H₃(NO₂)-COOH |
| 30 | HOOC-C₆H₃(NO₂)-COO-C₃H₆-OOC-C₆H₃(NO₂)-COOH |
| 31 | HOOC-C₆H₃(NO₂)-COO-C₄H₈-OOC-C₆H₃(NO₂)-COOH |

TABLE 1-continued
| Compound No. | Structure |
|---|---|
| 32 | 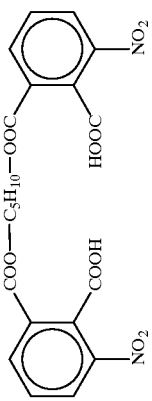 |
| 33 | 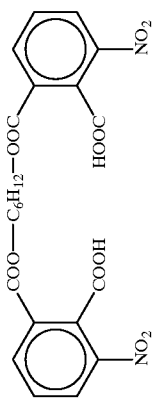 |
| 34 | 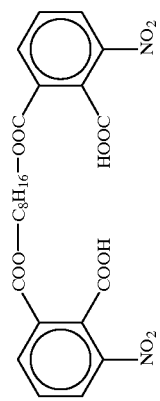 |
| 35 | 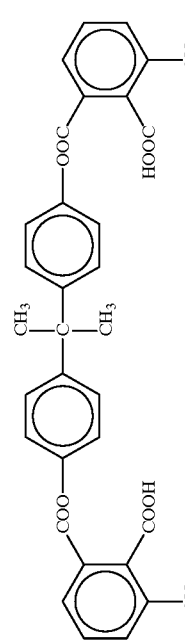 |
| 36 | 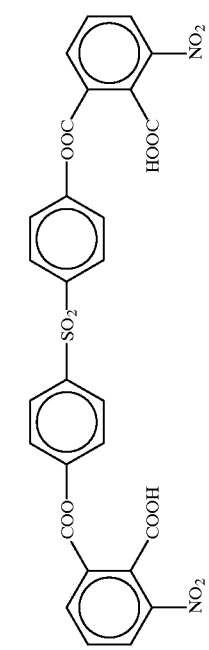 |

TABLE 1-continued

| Compound No. | Structure |
|---|---|
| 37 | (structure) |
| 38 | (structure) |
| 39 | (structure) |
| 40 | (structure) |
| 41 | (structure) |

TABLE 1-continued

| Compound No. | Structure |
|---|---|
| 42 | 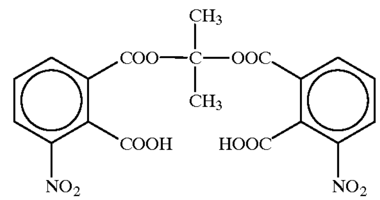 |
| 43 | 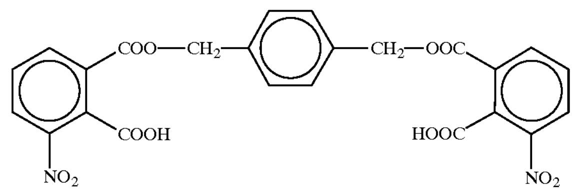 |
| 44 | 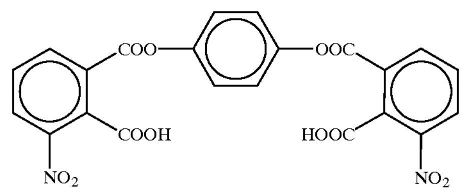 |
| 45 | 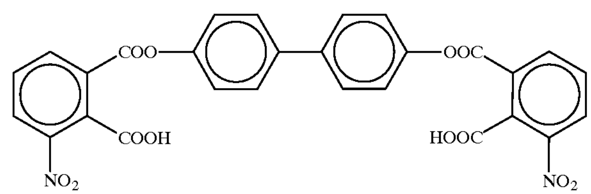 |
| 46 | 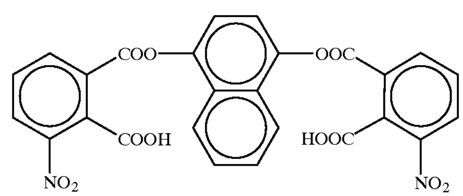 |

TABLE 1-continued

| Compound No. | Structure |
|---|---|
| 47 | HOOC-C$_6$H$_3$(NO$_2$)-CO-NH-C$_2$H$_4$-NH-OC-C$_6$H$_3$(NO$_2$)-COOH |
| 48 | HOOC-C$_6$H$_3$(NO$_2$)-CO-NH-C$_3$H$_6$-NH-OC-C$_6$H$_3$(NO$_2$)-COOH |
| 49 | HOOC-C$_6$H$_3$(NO$_2$)-CO-NH-C$_4$H$_8$-NH-OC-C$_6$H$_3$(NO$_2$)-COOH |
| 50 | HOOC-C$_6$H$_3$(NO$_2$)-CO-NH-C$_6$H$_{12}$-NH-OC-C$_6$H$_3$(NO$_2$)-COOH |
| 51 | (NO$_2$)(HOOC)C$_6$H$_3$-CONH-C$_6$H$_4$-SO$_2$-C$_6$H$_4$-CONH-C$_6$H$_3$(COOH)(NO$_2$) |

TABLE 1-continued

| Compound No. | Structure |
|---|---|
| 52 | (structure) |
| 53 | (structure) |
| 54 | (structure) |
| 55 | (structure) |
| 56 | (structure) |

TABLE 1-continued

| Compound No. | Structure |
|---|---|
| 57 | HOOC-C6H3(NO2)-COO-C2H4-OOC-C6H3(NO2)-COOH (with O2N and NO2 substituents) |
| 58 | HOOC-C6H3(NO2)-COO-C3H6-OOC-C6H3(NO2)-COOH |
| 59 | HOOC-C6H3(NO2)-COO-C4H8-OOC-C6H3(NO2)-COOH |
| 60 | HOOC-C6H3(NO2)-COO-C6H4-C(CH3)2-C6H4-OOC-C6H3(NO2)-COOH |
| 61 | HOOC-C6H3(NO2)-COO-C6H4-SO2-C6H4-OOC-C6H3(NO2)-COOH |
| 62 | HOOC-C6H3(NO2)-CO-NH-C2H4-NH-OC-C6H3(NO2)-COOH |
| 63 | HOOC-C6H3(NO2)-CO-NH-C3H6-NH-OC-C6H3(NO2)-COOH |

TABLE 1-continued

| Compound No. | Structure |
|---|---|
| 64 | (structure) |
| 65 | (structure) |
| 66 | (structure) |
| 67 | (structure) |
| 68 | (structure) |
| 69 | (structure) |

TABLE 1-continued

| Compound No. | Structure |
|---|---|
| 70 | HOOC-C₆H₃(O₂N)-COO-C₂H₄-OOC-C₆H₃(NO₂)-COOH |
| 71 | HOOC-C₆H₃(O₂N)-COO-C₃H₆-OOC-C₆H₃(NO₂)-COOH |
| 72 | HOOC-C₆H₃(O₂N)-COO-C₄H₈-OOC-C₆H₃(NO₂)-COOH |
| 73 | Bis[4-(3-carboxy-4-nitrobenzoyloxy)phenyl]propane (2,2-bis-phenyl with C(CH₃)₂ bridge) |
| 74 | Bis[4-(3-carboxy-4-nitrobenzoyloxy)phenyl] sulfone (SO₂ bridge) |
| 75 | HOOC-C₆H₃(O₂N)-CO-NH-C₂H₄-NH-OC-C₆H₃(NO₂)-COOH |
| 76 | HOOC-C₆H₃(O₂N)-CO-NH-C₃H₆-NH-OC-C₆H₃(NO₂)-COOH |

TABLE 1-continued

| Compound No. | Structure |
|---|---|
| 77 | (4-nitro-2-carboxyphenyl)-CO-NH-C6H4-NH-CO-(2-carboxy-4-nitrophenyl) |
| 78 | (4-nitro-2-carboxyphenyl)-CO-NH-CH2-C6H4-CH2-NH-CO-(2-carboxy-4-nitrophenyl) |
| 79 | (4-nitro-2-carboxyphenyl)-CO-NH-C6H4-CH2-C6H4-NH-CO-(2-carboxy-4-nitrophenyl) |
| 80 | (4-nitro-2-carboxyphenyl)-CO-NH-C6H4-O-C6H4-NH-CO-(2-carboxy-4-nitrophenyl) |
| 81 | (4-nitro-2-carboxyphenyl)-CO-NH-C6H4-SO2-C6H4-NH-CO-(2-carboxy-4-nitrophenyl) |
| 82 | (tetrachloro-carboxyphenyl)-COO-C2H4-OOC-(tetrachloro-carboxyphenyl) |

TABLE 1-continued

| Compound No. | Structure |
|---|---|
| 83 | (structure) |
| 84 | (structure) |
| 85 | (structure) |
| 86 | (structure) |

TABLE 1-continued
| Compound No. | Structure |
|---|---|
| 87 | 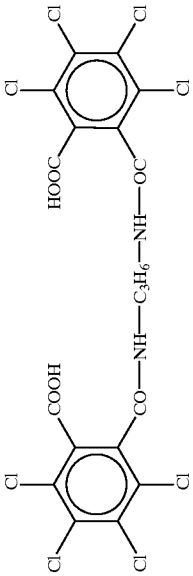 |
| 88 | 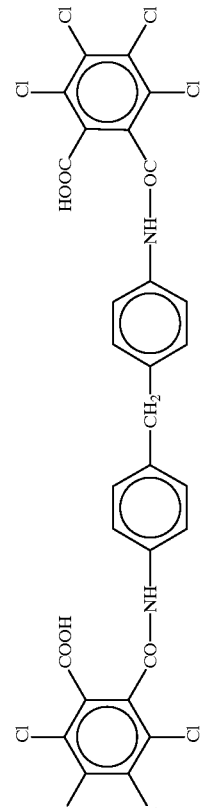 |
| 89 | 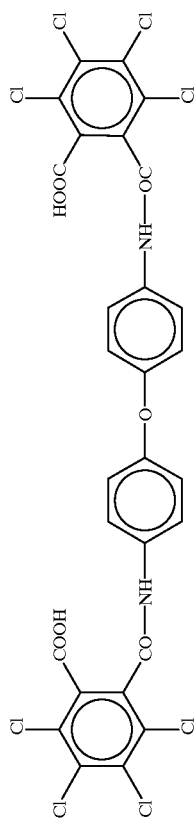 |
| 90 | 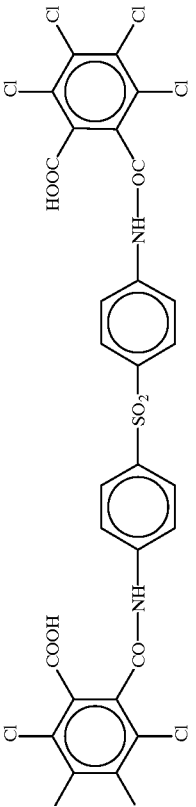 |
| 91 | 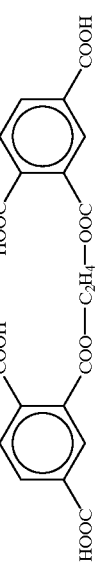 |

TABLE 1-continued

| Compound No. | Structure |
|---|---|
| 92 | (structure) |
| 93 | (structure) |
| 94 | (structure) |
| 95 | (structure) |
| 96 | (structure) |
| 97 | (structure) |

TABLE 1-continued

| Compound No. | Structure |
|---|---|
| 98 | (structure) |
| 99 | (structure) |
| 100 | (structure) |
| 101 | (structure) |
| 102 | (structure) |
| 103 | (structure) |
| 104 | (structure) |

TABLE 1-continued

| Compound No. | Structure |
|---|---|
| 105 | HOOC-C₆H₃(COOH)-CO-NH-C₃H₆-NH-OC-C₆H₃(COOH)-COOH |
| 106 | HOOC-C₆H₃(COOH)-CO-NH-C₆H₄-CH₂-C₆H₄-NH-OC-C₆H₃(COOH)-COOH |
| 107 | HOOC-C₆H₃(COOH)-CO-NH-C₆H₄-O-C₆H₄-NH-OC-C₆H₃(COOH)-COOH |
| 108 | HOOC-C₆H₃(COOH)-CO-NH-C₆H₄-SO₂-C₆H₄-NH-OC-C₆H₃(COOH)-COOH |
| 109 | H₃COOC-C₆H₃(COOH)-CONH-C₂H₄-HNOC-C₆H₃(COOH)-COOCH₃ |
| 110 | H₃COOC-C₆H₃(COOH)-CO-NH-C₃H₆-HN-OC-C₆H₃(COOH)-COOCH₃ |
| 111 | H₃COOC-C₆H₃(COOH)-CO-NH-C₄H₈-HN-OC-C₆H₃(COOH)-COOCH₃ |

TABLE 1-continued

| Compound No. | Structure |
|---|---|
| 112 | HOOC–C₆H₃(COOH)–CO–NH–C₆H₁₂–NH–OC–C₆H₃(COOCH₃)–COOCH₃ (with H₃COOC substituent) |
| 113 | H₃COOC–C₆H₃(COOH)–CO–NH–C₆H₄–CH₂–C₆H₄–NH–OC–C₆H₃(COOCH₃)–COOCH₃ (HOOC substituent) |
| 114 | H₃COOC–C₆H₃(COOH)–CO–NH–C₆H₄–O–C₆H₄–NH–OC–C₆H₃(COOCH₃)–COOCH₃ (HOOC substituent) |
| 115 | H₃COOC–C₆H₃(COOH)–CO–NH–C₆H₄–SO₂–C₆H₄–NH–OC–C₆H₃(COOCH₃)–COOCH₃ (HOOC substituent) |
| 116 | H₃COOC–C₆H₃(COOH)–CO–NH–C₆H₄–SO₂–C₆H₄–NH–OC–C₆H₃(COOCH₃)–COOCH₃ (HOOC substituent, meta-linked) |
| 117 | H₅C₂OOC–C₆H₃(COOH)–CO–NH–C₂H₄–NH–OC–C₆H₃(COOC₂H₅)–COOH |
| 118 | H₅C₂OOC–C₆H₃(COOH)–CO–NH–C₃H₆–NH–OC–C₆H₃(COOC₂H₅)–COOH |

TABLE 1-continued

| Compound No. | Structure |
|---|---|
| 119 | (structure) |
| 120 | (structure) |
| 121 | (structure) |
| 122 | (structure) |
| 123 | (structure) |
| 124 | (structure) |
| 125 | (structure) |

TABLE 1-continued

| Compound No. | Structure |
|---|---|
| 126 | (structure with C₃H₆ linker) |
| 127 | (structure with C₄H₈ linker) |
| 128 | (structure with C₆H₁₂ linker) |
| 129 | (structure with CH₂ bridge between phenyl rings) |
| 130 | (structure with O bridge between phenyl rings) |
| 131 | (structure with SO₂ bridge between phenyl rings) |

TABLE 1-continued

| Compound No. | Structure |
|---|---|
| 132 | 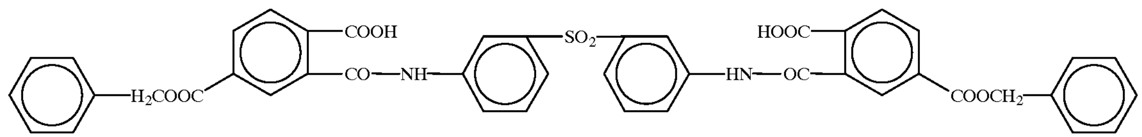 |
| 133 | 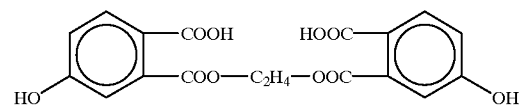 |
| 134 | 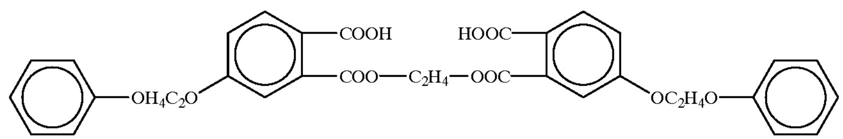 |
| 135 | 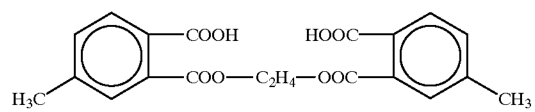 |
| 136 | 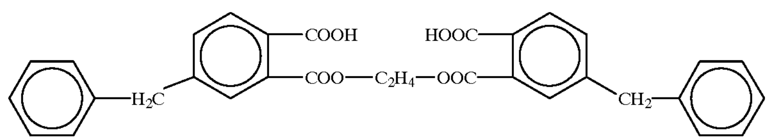 |
| 137 | 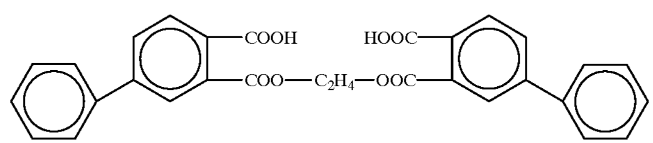 |
| 138 | 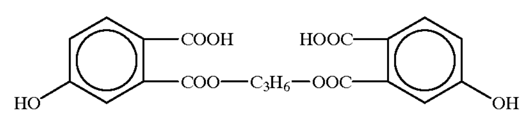 |

TABLE 1-continued

| Compound No. | Structure |
|---|---|
| 139 | 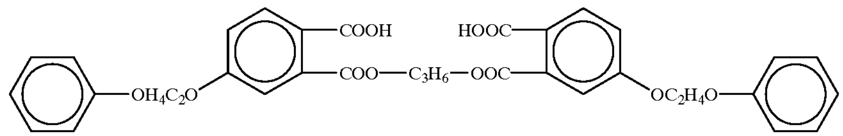 |
| 140 | 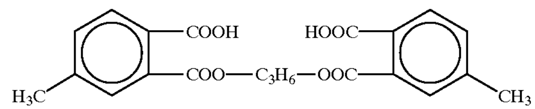 |
| 141 | 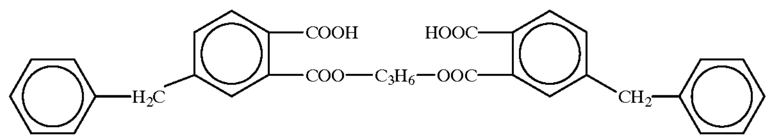 |
| 142 | 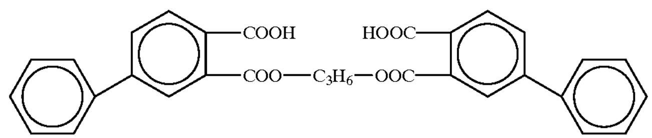 |
| 143 | 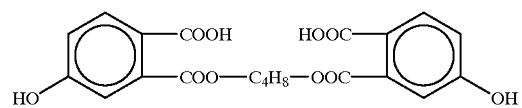 |
| 144 | 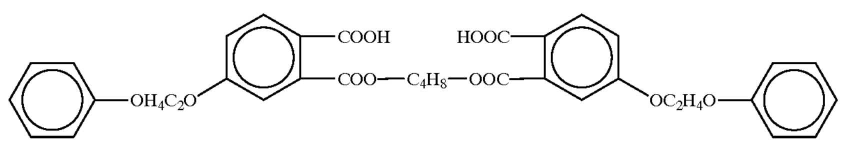 |
| 145 | 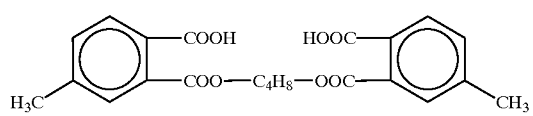 |

TABLE 1-continued

| Compound No. | Structure |
|---|---|
| 146 | HOOC-C6H3(CH2Ph)-COO-C4H8-OOC-C6H3(CH2Ph)-COOH |
| 147 | HOOC-C6H3(Ph)-COO-C4H8-OOC-C6H3(Ph)-COOH |
| 148 | HOOC-C6H3(OH)-COO-C5H10-OOC-C6H3(OH)-COOH |
| 149 | HOOC-C6H3(OC2H4O-Ph)-COO-C5H10-OOC-C6H3(OC2H4O-Ph)-COOH |
| 150 | HOOC-C6H3(CH3)-COO-C5H10-OOC-C6H3(CH3)-COOH |
| 151 | HOOC-C6H3(CH2Ph)-COO-C5H10-OOC-C6H3(CH2Ph)-COOH |
| 152 | HOOC-C6H3(Ph)-COO-C5H10-OOC-C6H3(Ph)-COOH |

TABLE 1-continued

| Compound No. | Structure |
|---|---|
| 153 | HOOC-C6H4(OH)-COO-C6H12-OOC-C6H4-OH |
| 154 | HOOC-C6H4(OC2H4O-C6H5)-COO-C6H12-OOC-C6H4-OC2H4O-C6H5 |
| 155 | HOOC-C6H4(CH3)-COO-C6H12-OOC-C6H4-CH3 |
| 156 | HOOC-C6H4(CH2-C6H5)-COO-C6H12-OOC-C6H4-CH2-C6H5 |
| 157 | HOOC-C6H4(C6H5)-COO-C6H12-OOC-C6H4-C6H5 |
| 158 | HOOC-C6H4(OH)-COO-C8H16-OOC-C6H4-OH |
| 159 | HOOC-C6H4(OC2H4O-C6H5)-COO-C8H16-OOC-C6H4-OC2H4O-C6H5 |

TABLE 1-continued

| Compound No. | Structure |
|---|---|
| 160 | (structure) |
| 161 | (structure) |
| 162 | (structure) |
| 163 | (structure) |
| 164 | (structure) |
| 165 | (structure) |

TABLE 1-continued

| Compound No. | Structure |
|---|---|
| 166 | (structure) |
| 167 | (structure) |
| 168 | (structure) |
| 169 | (structure) |
| 170 | (structure) |
| 171 | (structure) |

TABLE 1-continued

| Compound No. | Structure |
|---|---|
| 172 | 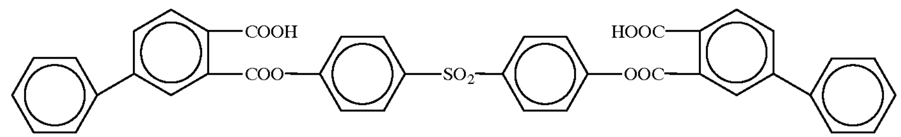 |
| 173 | 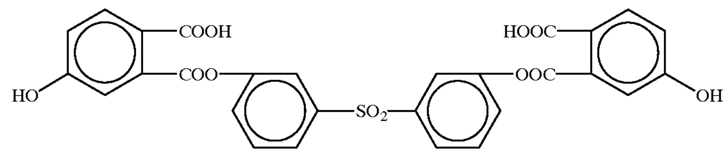 |
| 174 | 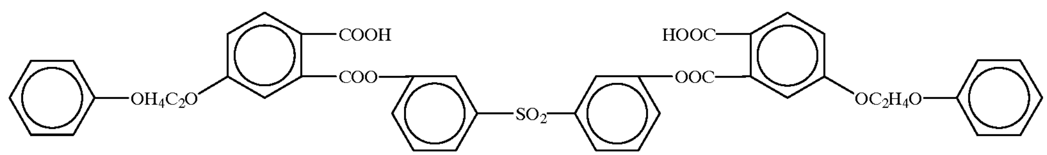 |
| 175 | 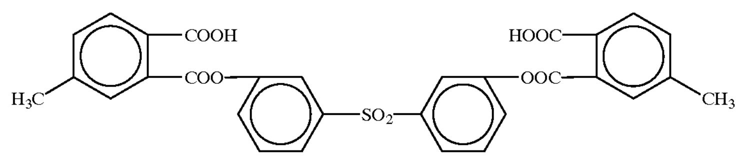 |
| 176 | 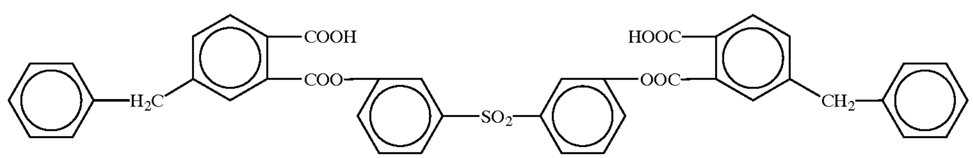 |
| 177 | 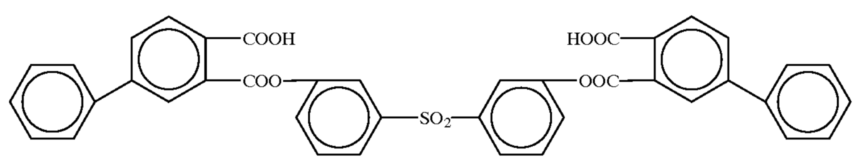 |

TABLE 1-continued
| Compound No. | Structure |
|---|---|
| 178 | 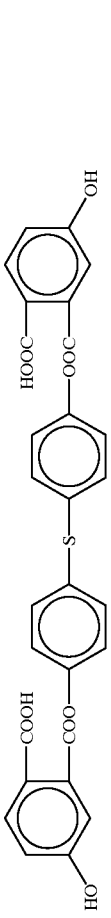 |
| 179 | 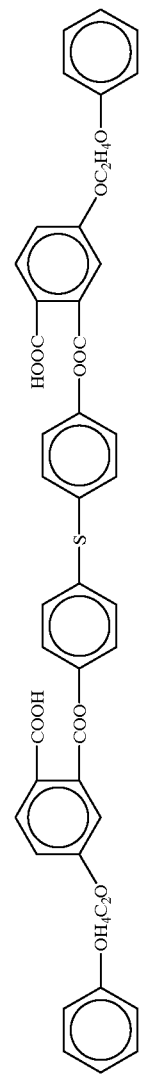 |
| 180 | 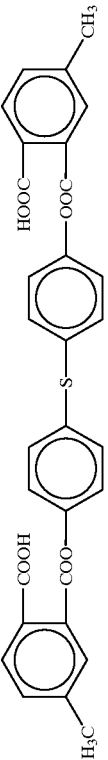 |
| 181 | 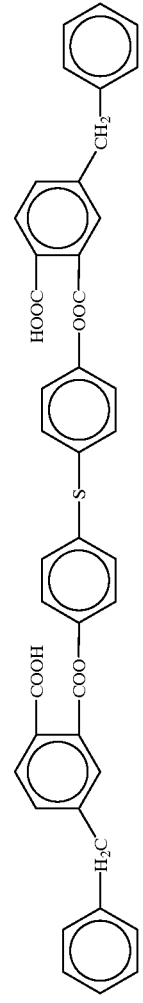 |
| 182 | 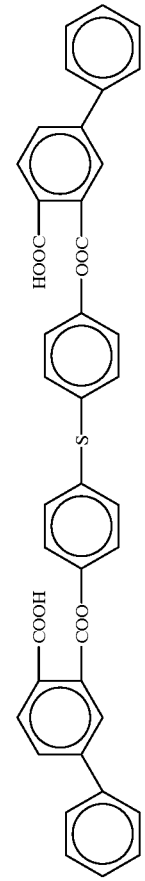 |
| 183 | 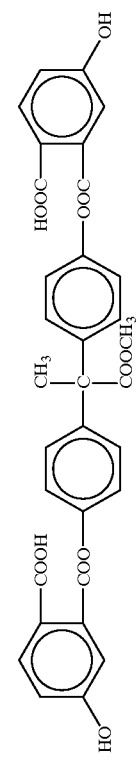 |

TABLE 1-continued

| Compound No. | Structure |
|---|---|
| 184 | 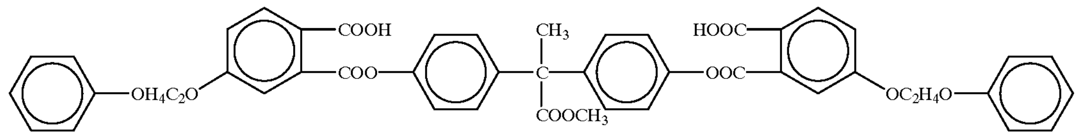 |
| 185 | 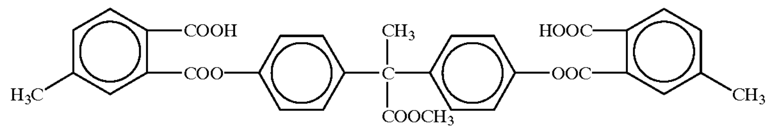 |
| 186 | 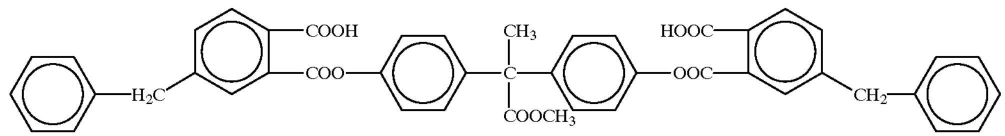 |
| 187 | 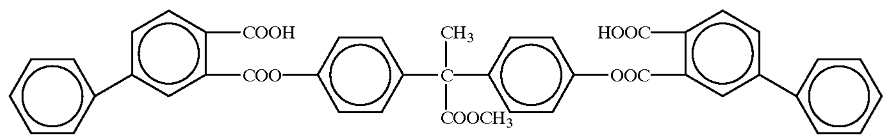 |
| 188 | 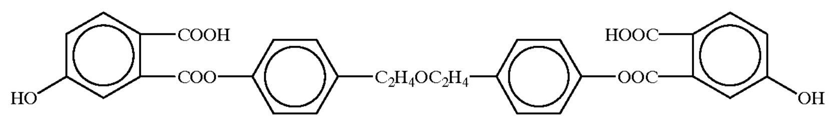 |
| 189 | 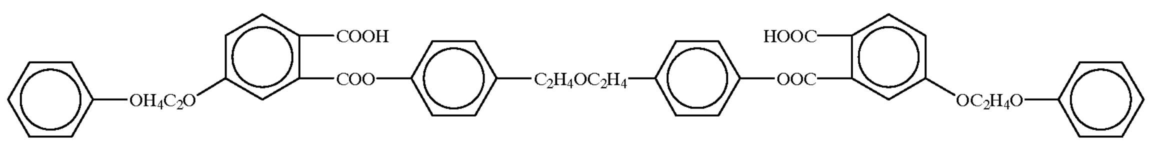 |

TABLE 1-continued

| Compound No. | Structure |
|---|---|
| 190 | 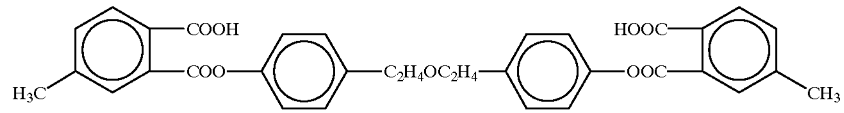 |
| 191 | 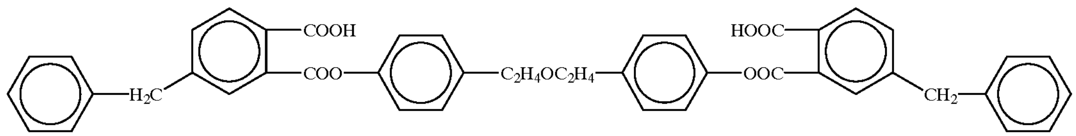 |
| 192 | 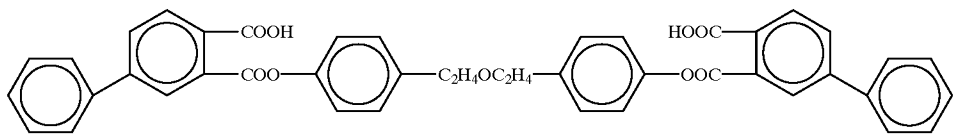 |
| 193 | 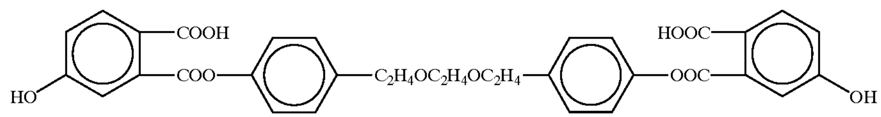 |
| 194 | 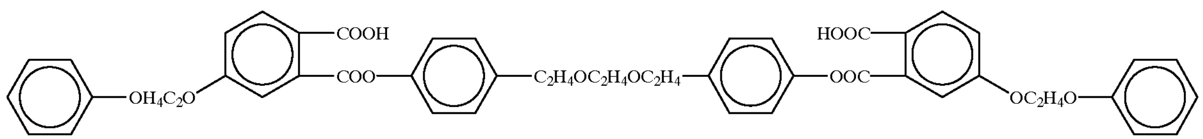 |
| 195 | 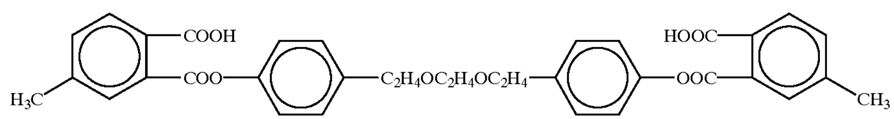 |
| 196 | 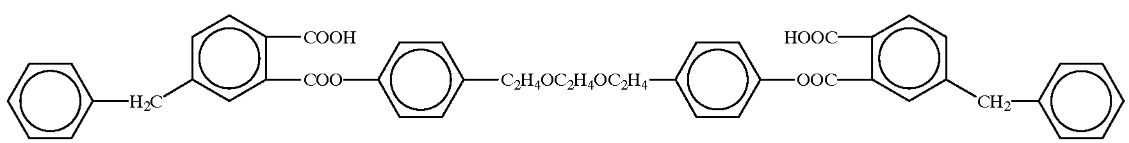 |

TABLE 1-continued

| Compound No. | Structure |
|---|---|
| 197 | HOOC-C6H3(-C6H5)-COO-C6H4-C2H4OC2H4OC2H4-C6H4-OOC-C6H3(-C6H5)-COOH |
| 198 | HO-C6H3(-COOH)-OOC-C6H4-C2H4OC2H4OC2H4-C6H4-COO-C6H3(-COOH)-OH |
| 199 | C6H5-OC2H4O-C6H3(-COOH)-OOC-C6H4-C2H4OC2H4OC2H4-C6H4-COO-C6H3(-COOH)-OC2H4O-C6H5 |
| 200 | H3C-C6H3(-COOH)-OOC-C6H4-C2H4OC2H4OC2H4-C6H4-COO-C6H3(-COOH)-CH3 |
| 201 | C6H5-CH2-C6H3(-COOH)-OOC-C6H4-C2H4OC2H4OC2H4-C6H4-COO-C6H3(-COOH)-CH2-C6H5 |
| 202 | C6H5-C6H3(-COOH)-OOC-C6H4-C2H4OC2H4OC2H4-C6H4-COO-C6H3(-COOH)-C6H5 |

TABLE 1-continued

| Compound No. | Structure |
|---|---|
| 203 | 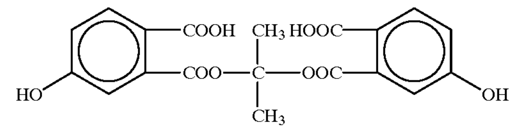 |
| 204 | 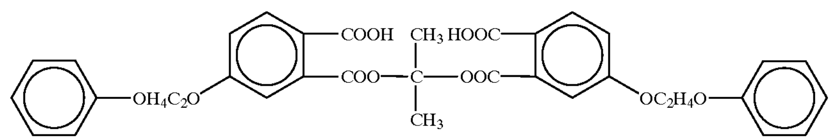 |
| 205 | 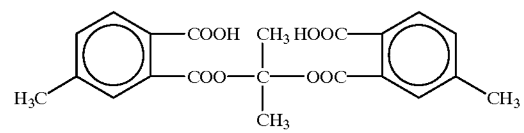 |
| 206 | 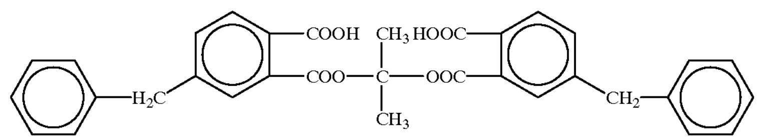 |
| 207 | 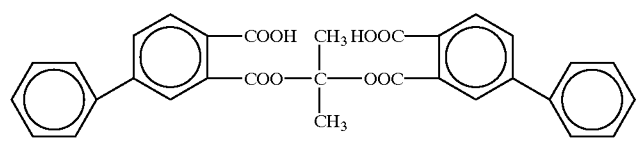 |
| 208 | 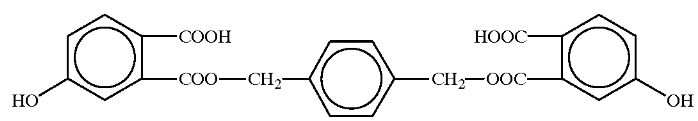 |

TABLE 1-continued

| Compound No. | Structure |
|---|---|
| 209 | (structure) |
| 210 | (structure) |
| 211 | (structure) |
| 212 | (structure) |
| 213 | (structure) |
| 214 | (structure) |
| 215 | (structure) |

TABLE 1-continued

| Compound No. | Structure |
|---|---|
| 216 | 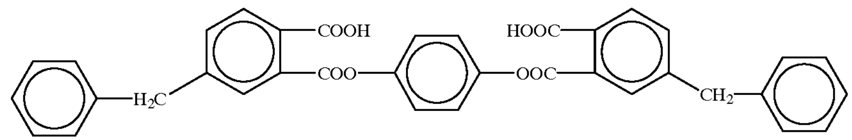 |
| 217 | 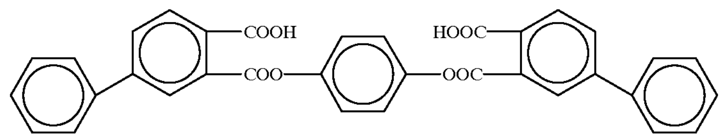 |
| 218 | 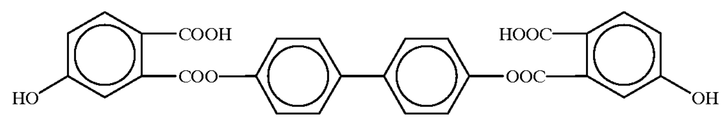 |
| 219 | 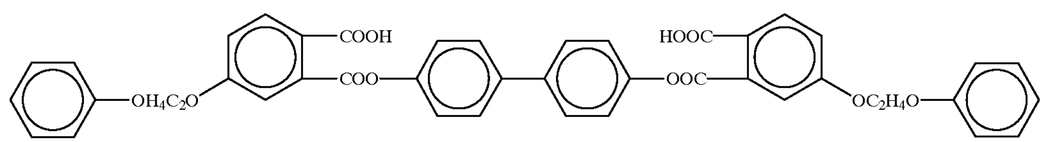 |
| 220 | 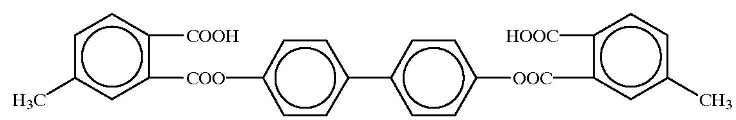 |
| 221 | 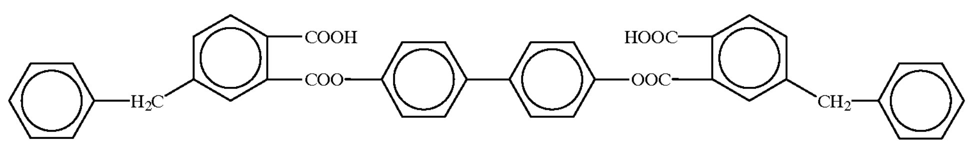 |

TABLE 1-continued

| Compound No. | Structure |
|---|---|
| 222 | 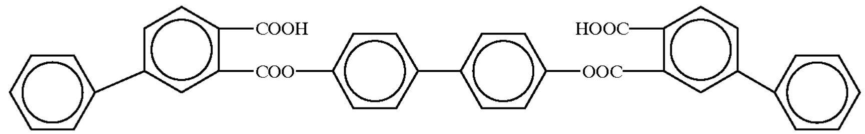 |
| 223 | 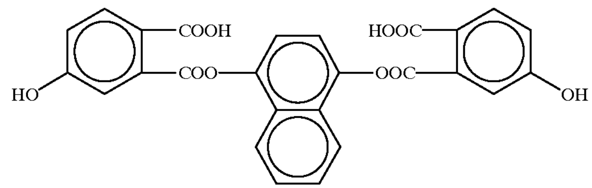 |
| 224 | 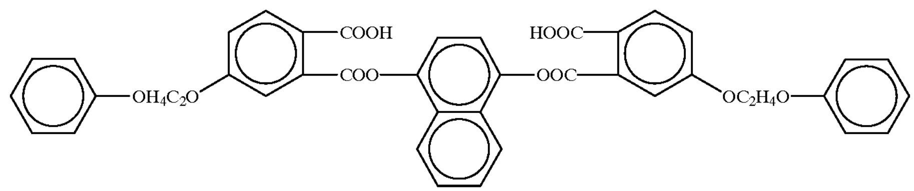 |
| 225 | 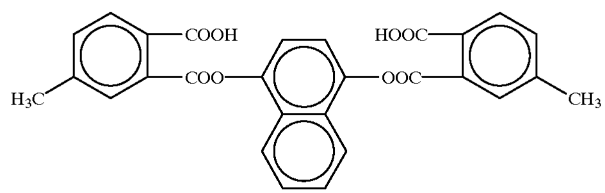 |
| 226 | 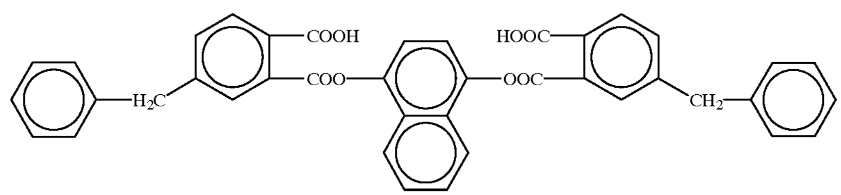 |

TABLE 1-continued

| Compound No. | Structure |
|---|---|
| 227 | (structure) |
| 228 | (structure) |
| 229 | (structure) |
| 230 | (structure) |
| 231 | (structure) |

TABLE 1-continued

| Compound No. | Structure |
|---|---|
| 232 | 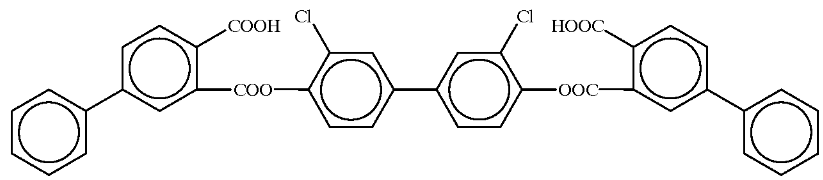 |
| 233 | 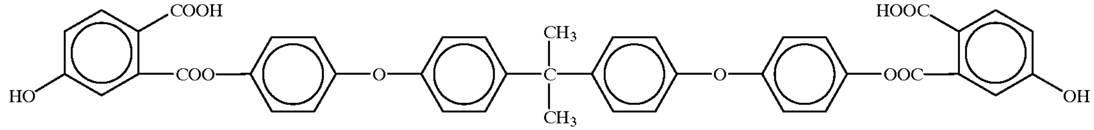 |
| 234 | 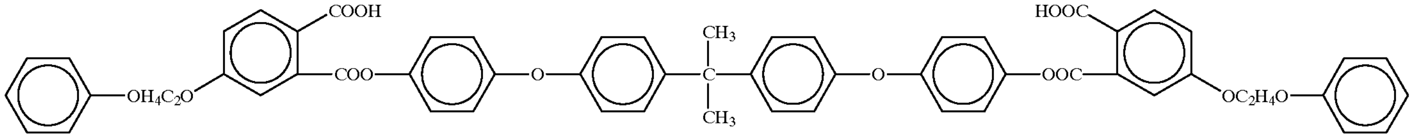 |
| 235 | 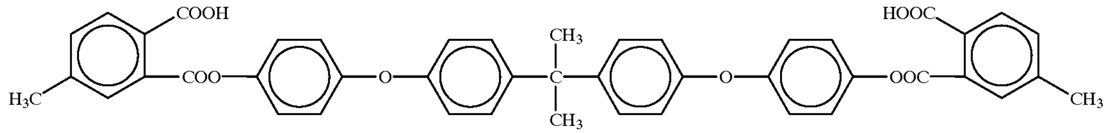 |
| 236 | 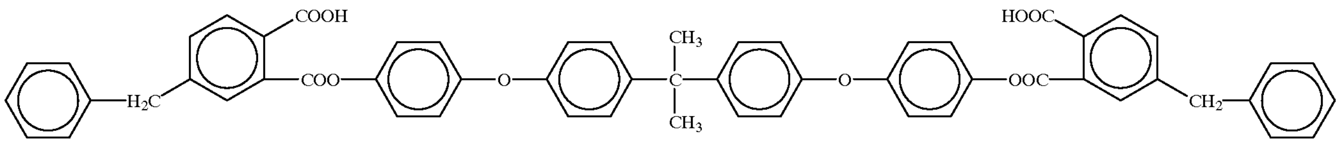 |
| 237 | 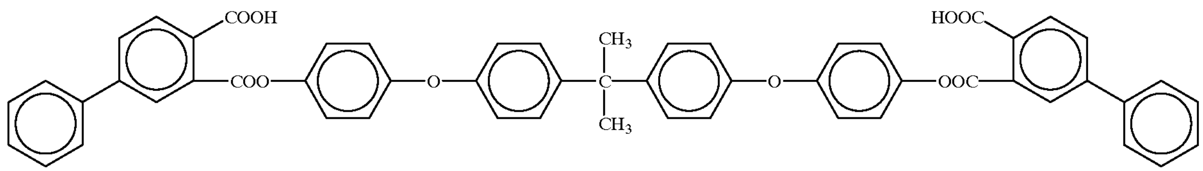 |

TABLE 1-continued

| Compound No. | Structure |
|---|---|
| 238 | 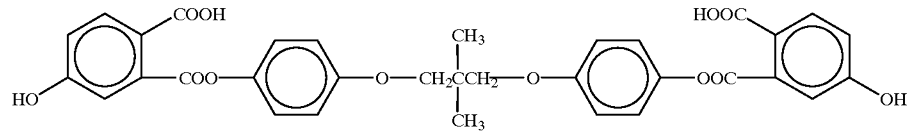 |
| 239 | 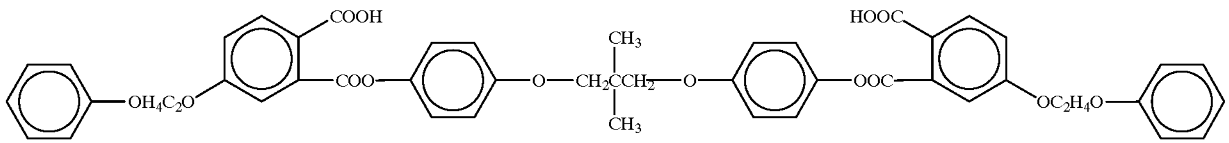 |
| 240 | 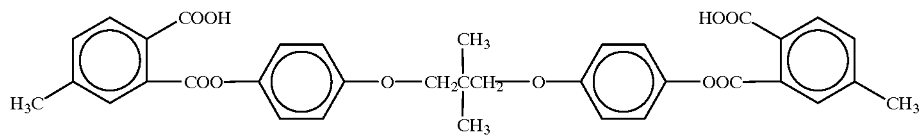 |
| 241 | 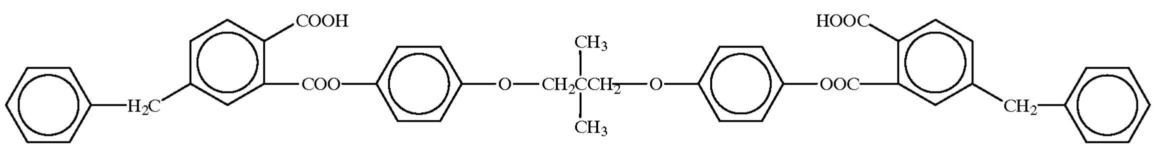 |
| 242 | 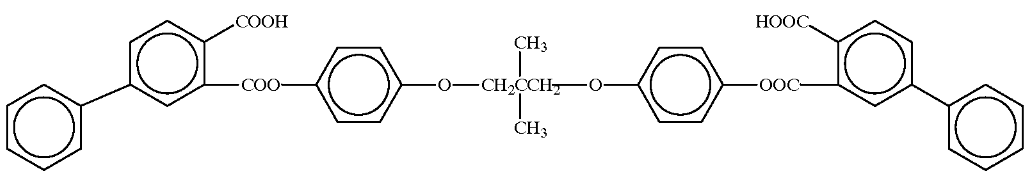 |
| 243 | 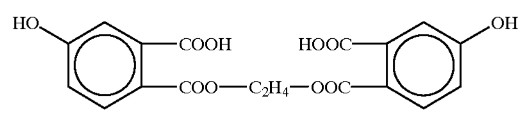 |

TABLE 1-continued

| Compound No. | Structure |
|---|---|
| 244 | (structure) |
| 245 | (structure) |
| 246 | (structure) |
| 247 | (structure) |
| 248 | (structure) |
| 249 | (structure) |
| 250 | (structure) |

TABLE 1-continued
| Compound No. | Structure |
|---|---|
| 251 | 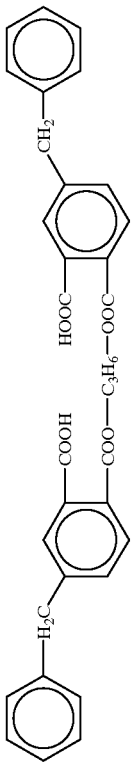 |
| 252 | 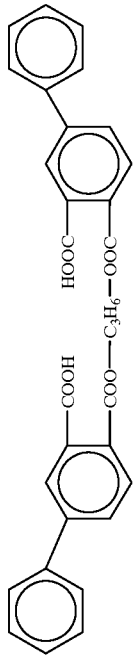 |
| 253 | 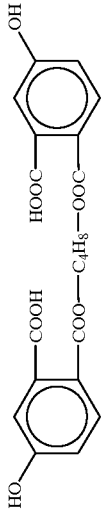 |
| 254 | 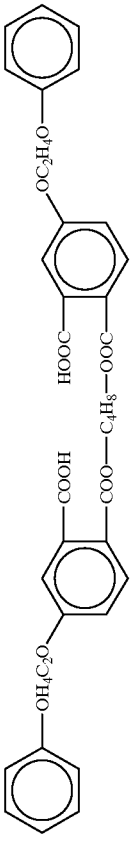 |
| 255 | 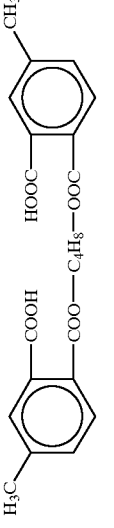 |
| 256 | 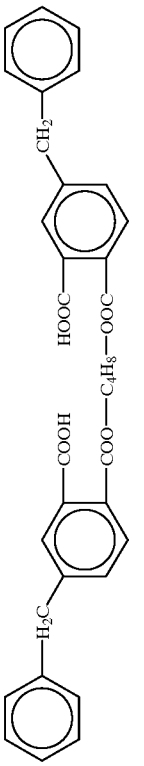 |
| 257 | 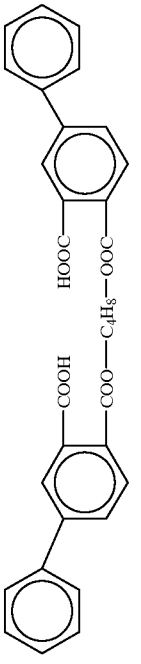 |

TABLE 1-continued

| Compound No. | Structure |
|---|---|
| 258 | (structure) |
| 259 | (structure) |
| 260 | (structure) |
| 261 | (structure) |
| 262 | (structure) |
| 263 | (structure) |
| 264 | (structure) |

TABLE 1-continued

| Compound No. | Structure |
|---|---|
| 265 | 4-methylphenyl 4-methylsalicylate linked via –COO–C₆H₁₂–OOC– |
| 266 | 3-benzylphenyl 3-benzylsalicylate linked via –COO–C₆H₁₂–OOC– |
| 267 | 3-phenylphenyl 3-phenylsalicylate linked via –COO–C₆H₁₂–OOC– |
| 268 | 4-hydroxyphenyl 4-hydroxysalicylate linked via –COO–C₈H₁₆–OOC– |
| 269 | 4-phenoxyethoxyphenyl 4-phenoxyethoxysalicylate linked via –COO–C₈H₁₆–OOC– |
| 270 | 4-methylphenyl 4-methylsalicylate linked via –COO–C₈H₁₆–OOC– |
| 271 | 3-benzylphenyl 3-benzylsalicylate linked via –COO–C₈H₁₆–OOC– |

TABLE 1-continued

| Compound No. | Structure |
| --- | --- |
| 272 | 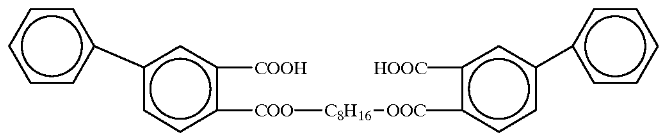 |
| 273 | 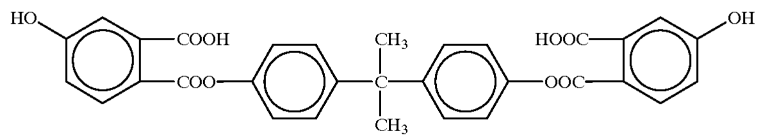 |
| 274 | 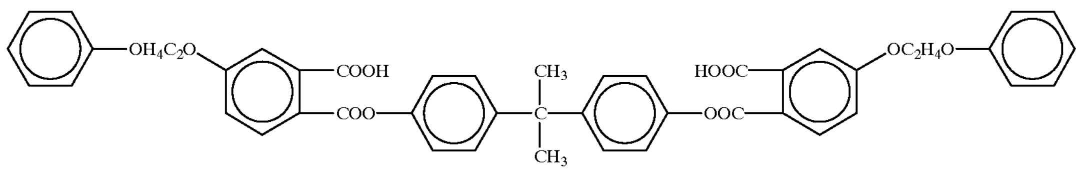 |
| 275 | 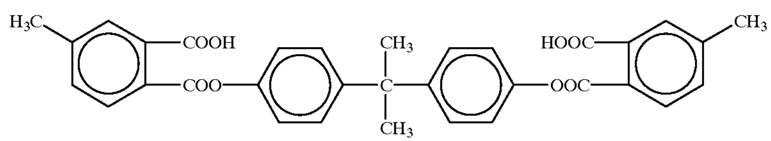 |
| 276 | 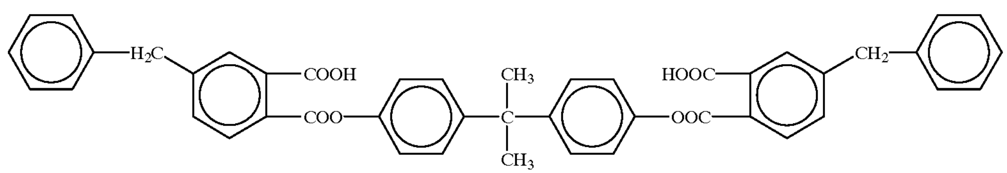 |
| 277 | 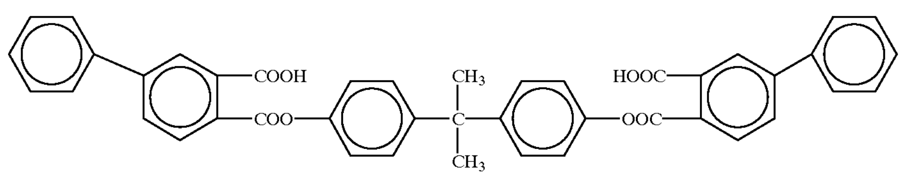 |

TABLE 1-continued
| Compound No. | Structure |
|---|---|
| 278 | 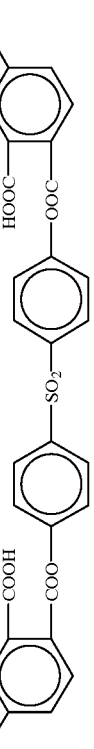 |
| 279 | 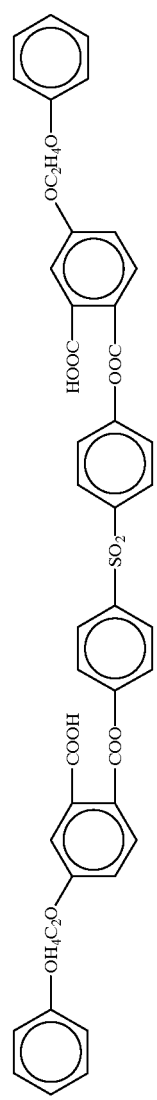 |
| 280 | 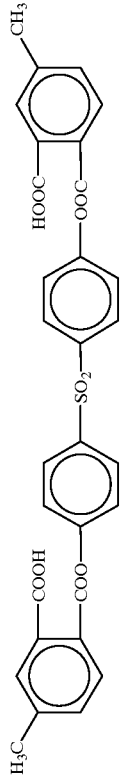 |
| 281 | 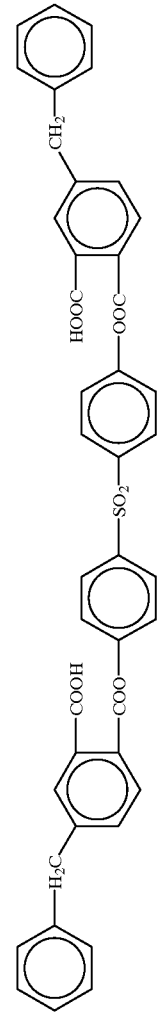 |
| 282 | 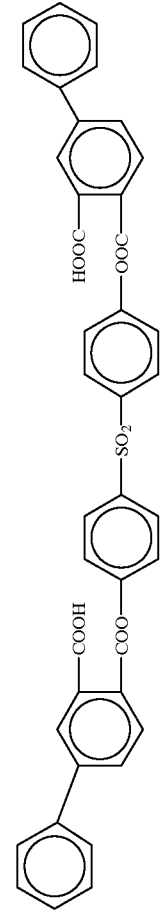 |
| 283 | 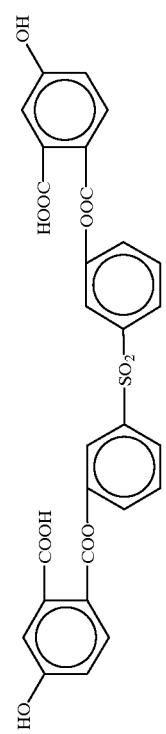 |

TABLE 1-continued

| Compound No. | Structure |
|---|---|
| 284 | 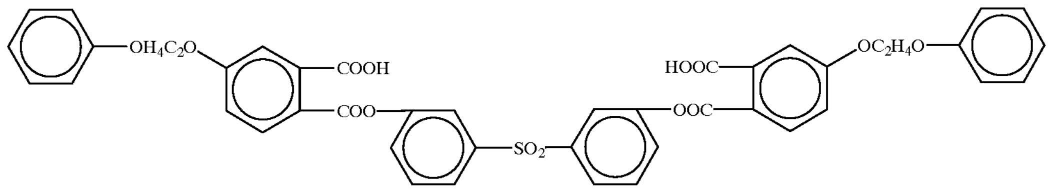 |
| 285 | 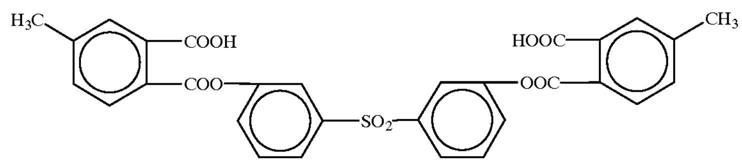 |
| 286 | 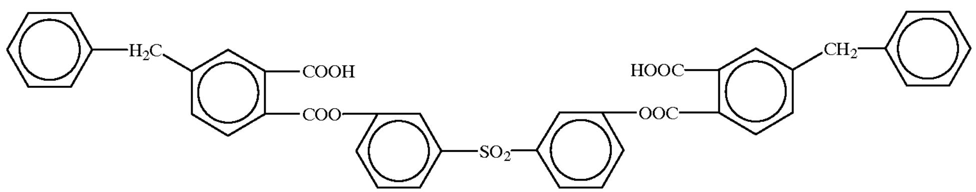 |
| 287 | 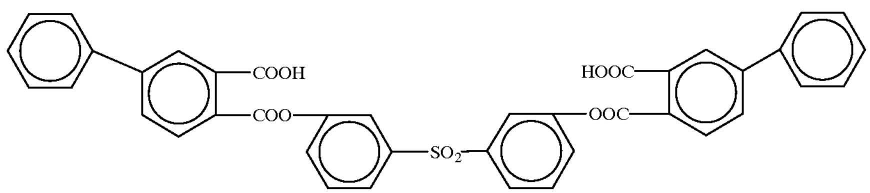 |
| 288 | 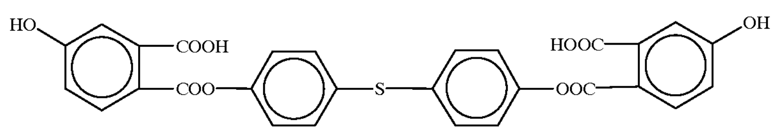 |

TABLE 1-continued

| Compound No. | Structure |
|---|---|
| 289 | (structure) |
| 290 | (structure) |
| 291 | (structure) |
| 292 | (structure) |
| 293 | (structure) |
| 294 | (structure) |

TABLE 1-continued

| Compound No. | Structure |
|---|---|
| 295 | 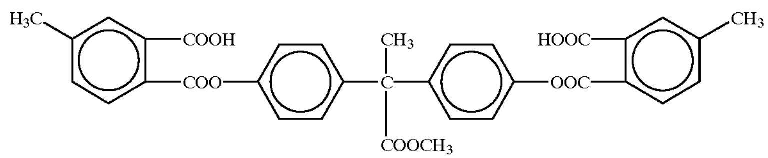 |
| 296 | 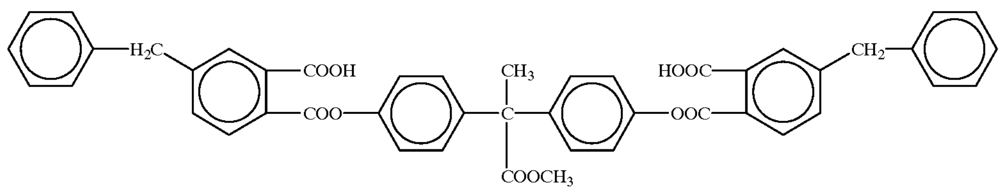 |
| 297 | 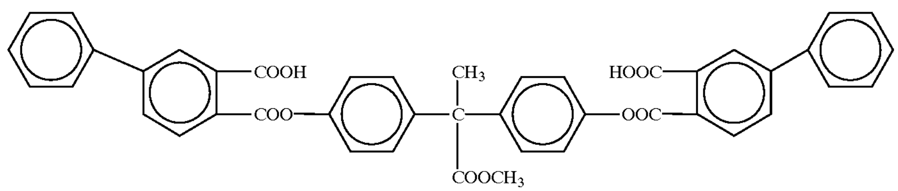 |
| 298 | 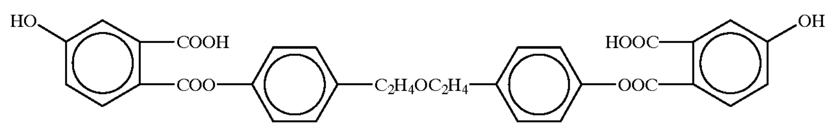 |
| 299 | 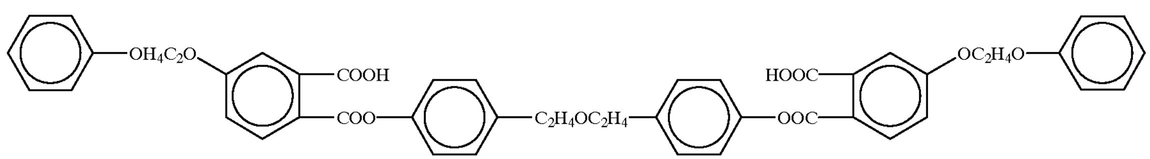 |
| 300 | 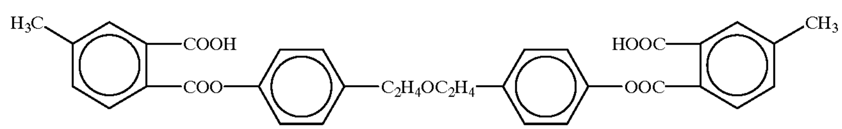 |

TABLE 1-continued

| Compound No. | Structure |
|---|---|
| 301 | 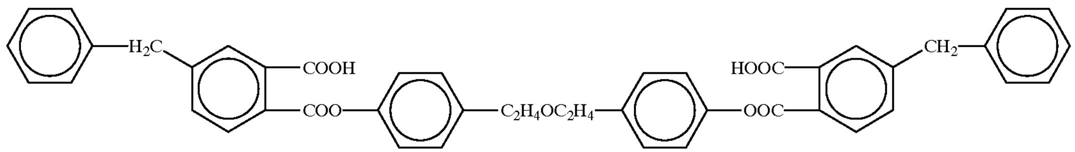 |
| 302 | 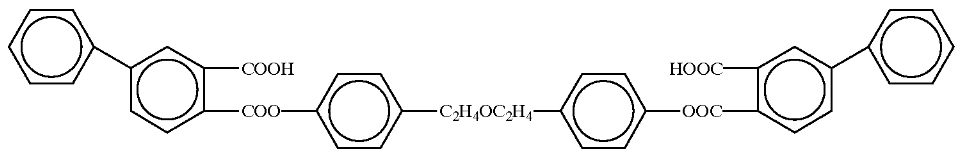 |
| 303 | 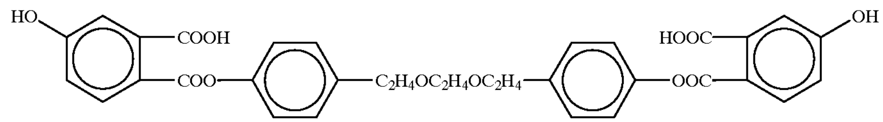 |
| 304 | 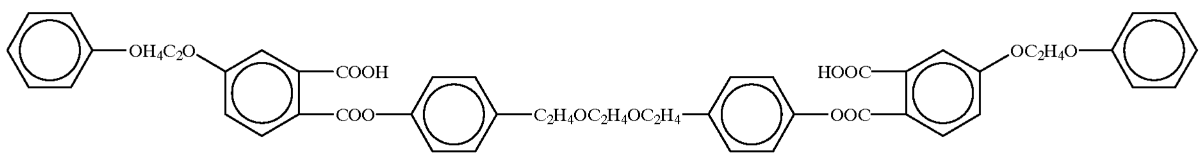 |
| 305 | 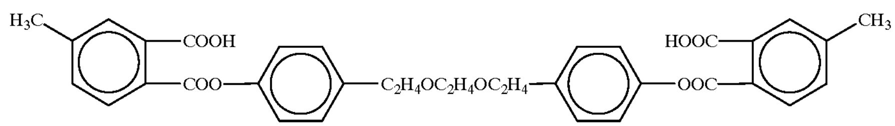 |
| 306 | 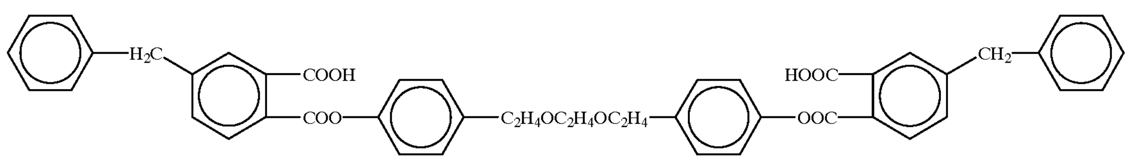 |

TABLE 1-continued

| Compound No. | Structure |
|---|---|
| 307 | (structure) |
| 308 | (structure) |
| 309 | (structure) |
| 310 | (structure) |
| 311 | (structure) |
| 312 | (structure) |

TABLE 1-continued

| Compound No. | Structure |
|---|---|
| 313 | (structure) |
| 314 | (structure) |
| 315 | (structure) |
| 316 | (structure) |
| 317 | (structure) |
| 318 | (structure) |

TABLE 1-continued

| Compound No. | Structure |
|---|---|
| 319 | 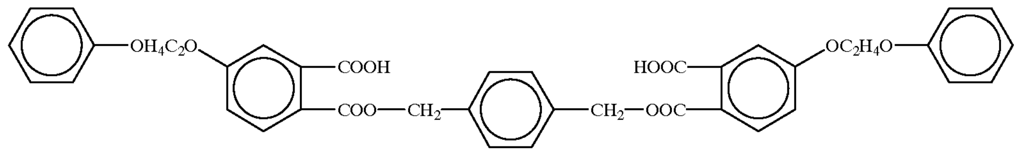 |
| 320 | 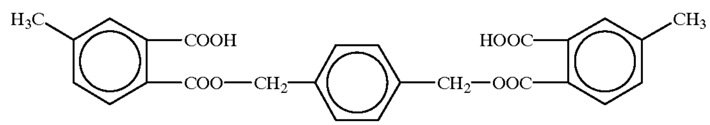 |
| 321 | 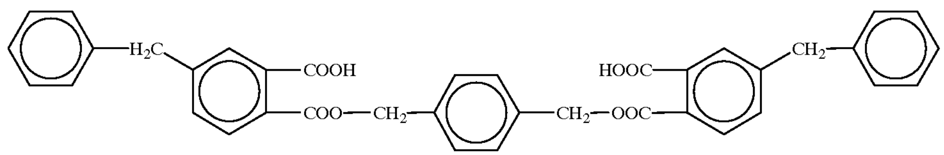 |
| 322 | 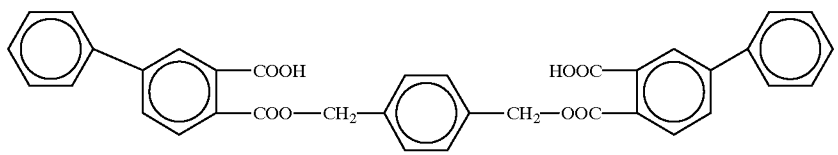 |
| 323 | 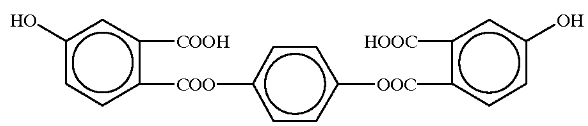 |
| 324 | 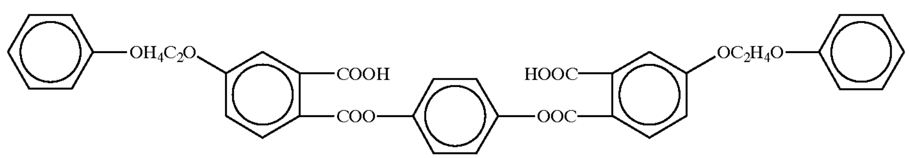 |

TABLE 1-continued

| Compound No. | Structure |
|---|---|
| 325 | 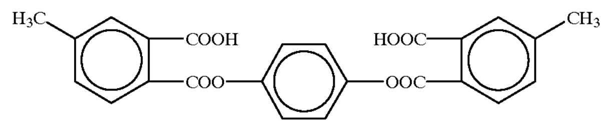 |
| 326 | 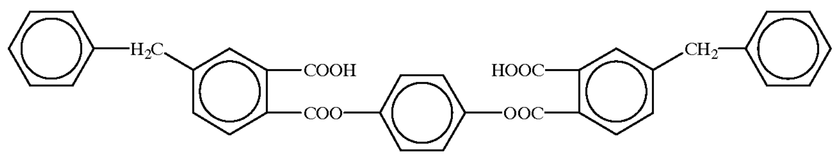 |
| 327 | 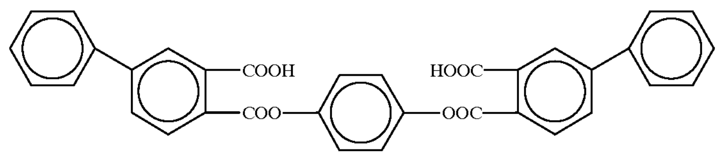 |
| 328 | 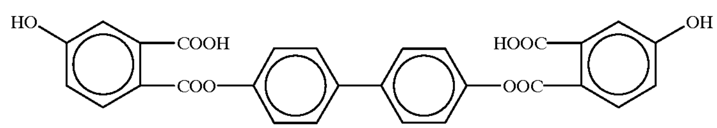 |
| 329 | 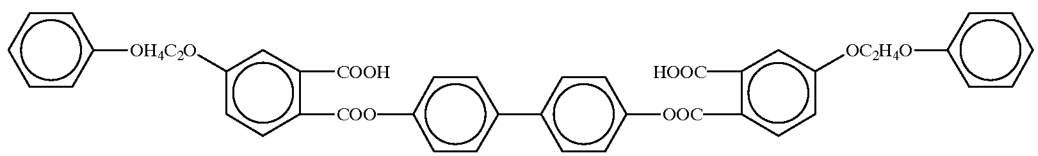 |
| 330 | 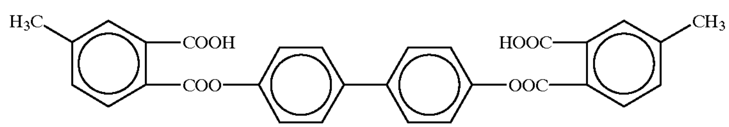 |

TABLE 1-continued
| Compound No. | Structure |
|---|---|
| 331 | 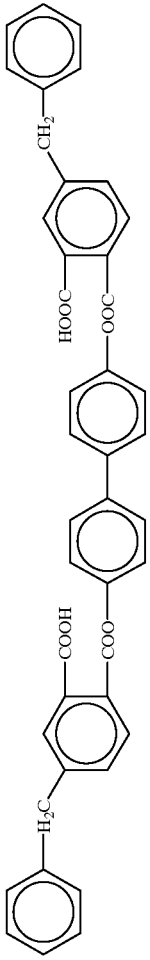 |
| 332 | 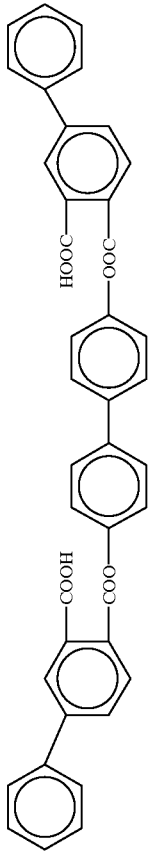 |
| 333 | 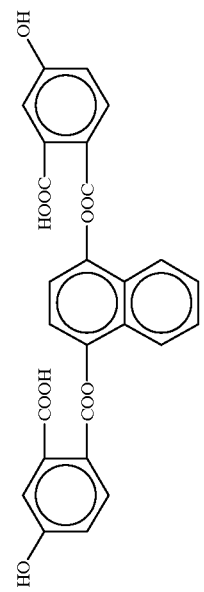 |
| 334 | 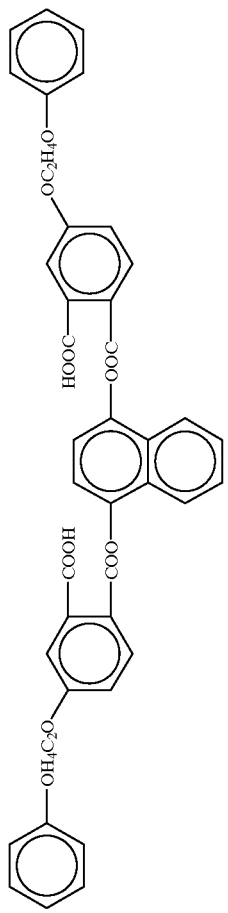 |
| 335 | 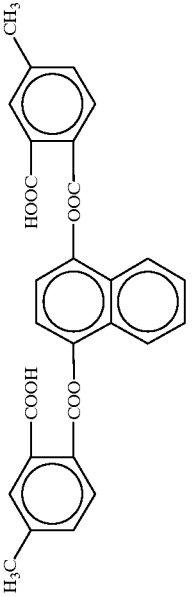 |

TABLE 1-continued

| Compound No. | Structure |
|---|---|
| 336 | (structure) |
| 337 | (structure) |
| 338 | (structure) |
| 339 | (structure) |
| 340 | (structure) |

TABLE 1-continued

| Compound No. | Structure |
|---|---|
| 341 | 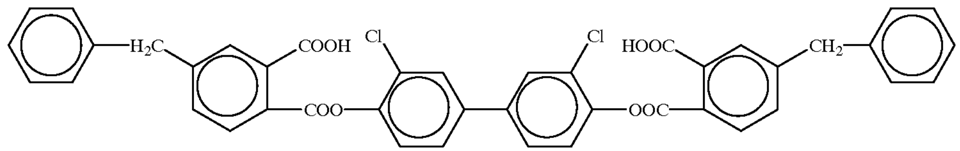 |
| 342 | 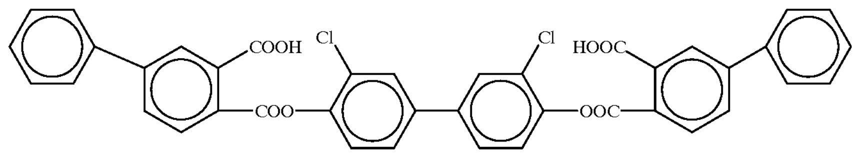 |
| 343 | 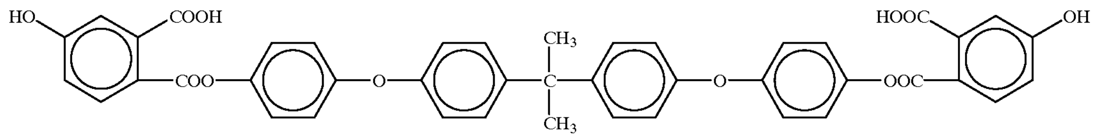 |
| 344 | 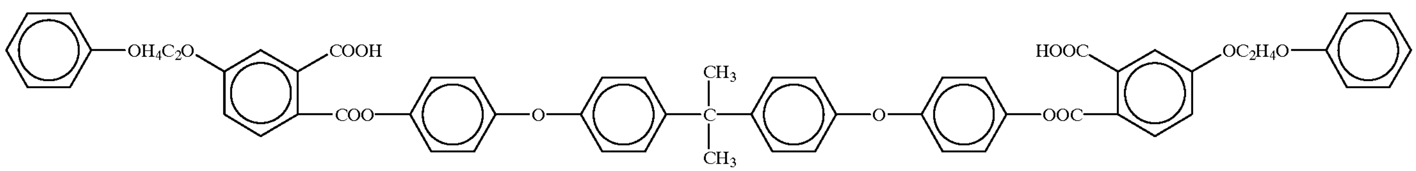 |
| 345 | 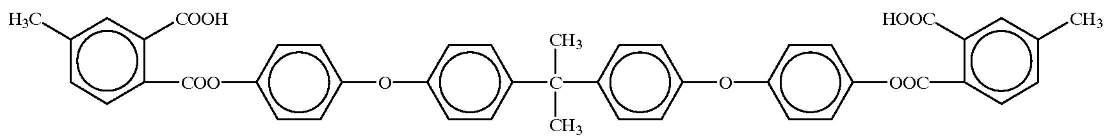 |
| 346 | 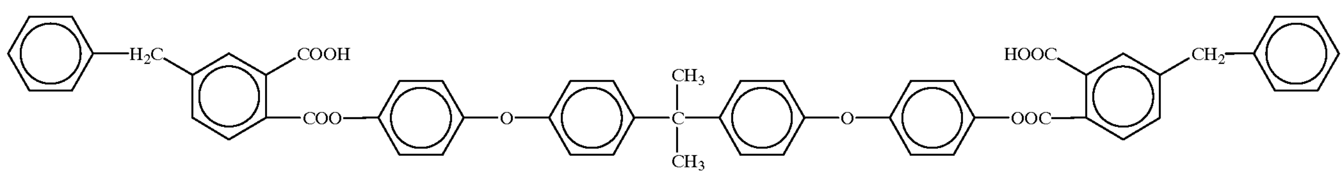 |

TABLE 1-continued

| Compound No. | Structure |
|---|---|
| 347 | 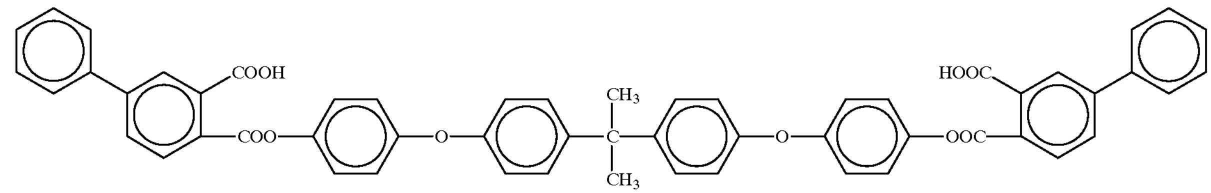 |
| 348 | 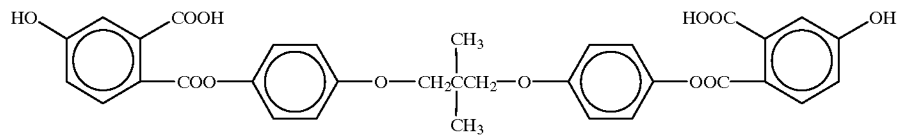 |
| 349 | 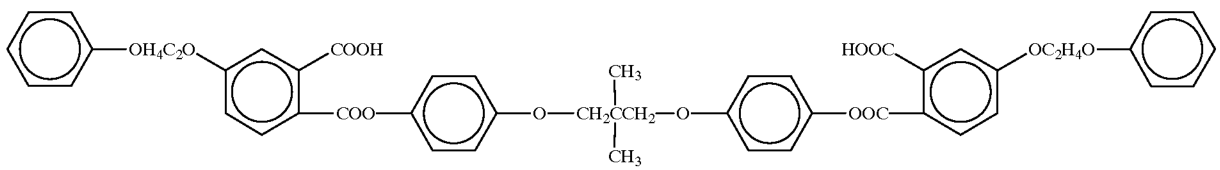 |
| 350 | 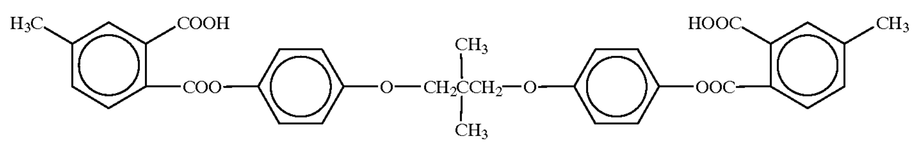 |
| 351 | 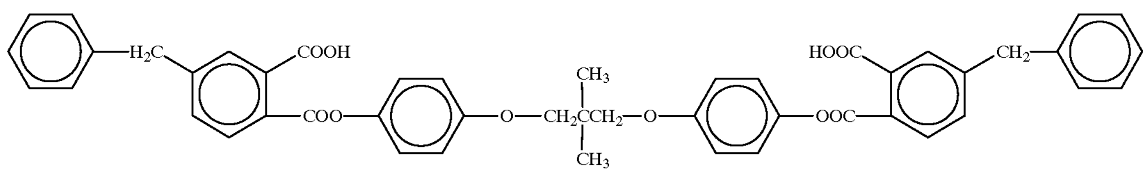 |

TABLE 1-continued

| Compound No. | Structure |
|---|---|
| 352 | (structure) |
| 353 | (structure) |
| 354 | (structure) |
| 355 | (structure) |
| 356 | (structure) |
| 357 | (structure) |

TABLE 1-continued

| Compound No. | Structure |
|---|---|
| 358 | 4-H₃C-C₆H₄-SO₂-O-C₆H₃(COOH)(CONH-C₂H₄-HNOC)-C₆H₃(COOH)(CONH)-O-SO₂-C₆H₄-CH₃-4 |
| 359 | 4-HO-C₆H₃(COOH)(CONH-C₃H₆-HNOC)-C₆H₃(COOH)(CONH)-OH-4 |
| 360 | C₆H₅-O-C₂H₄-O-C₆H₃(COOH)(CONH-C₃H₆-HNOC)-C₆H₃(COOH)(CONH)-O-C₂H₄-O-C₆H₅ |
| 361 | 4-H₃C-C₆H₃(COOH)(CONH-C₃H₆-HNOC)-C₆H₃(COOH)(CONH)-CH₃-4 |
| 362 | 4-(C₆H₅-CH₂)-C₆H₃(COOH)(CONH-C₃H₆-HNOC)-C₆H₃(COOH)(CONH)-CH₂-C₆H₅-4 |
| 363 | 4-(C₆H₅)-C₆H₃(COOH)(CONH-C₃H₆-HNOC)-C₆H₃(COOH)(CONH)-C₆H₅-4 |

TABLE 1-continued

| Compound No. | Structure |
|---|---|
| 364 | (structure) |
| 365 | (structure) |
| 366 | (structure) |
| 367 | (structure) |
| 368 | (structure) |
| 369 | (structure) |
| 370 | (structure) |

TABLE 1-continued

| Compound No. | Structure |
| --- | --- |
| 371 | HO–C6H4–CONH–C6H12–HNOC–C6H4–OH (with COOH and HOOC groups) |
| 372 | PhOC2H4O–C6H4–CONH–C6H12–HNOC–C6H4–OC2H4OPh (with COOH and HOOC groups) |
| 373 | H3C–C6H4–CONH–C6H12–HNOC–C6H4–CH3 (with COOH and HOOC groups) |
| 374 | PhCH2–C6H4–CONH–C6H12–HNOC–C6H4–CH2Ph (with COOH and HOOC groups) |
| 375 | Ph–C6H4–CONH–C6H12–HNOC–C6H4–Ph (with COOH and HOOC groups) |
| 376 | (4-H3C-C6H4)–O–SO2–C6H4–CONH–C6H12–HNOC–C6H4–SO2–O–(4-C6H4-CH3) (with COOH and HOOC groups) |
| 377 | HO–C6H3(COOH)–CONH–C2H4OC2H4–HNOC–C6H3(HOOC)–OH |

TABLE 1-continued

| Compound No. | Structure |
|---|---|
| 378 | (structure) |
| 379 | (structure) |
| 380 | (structure) |
| 381 | (structure) |
| 382 | (structure) |
| 383 | (structure) |

TABLE 1-continued

| Compound No. | Structure |
|---|---|
| 384 | (structure) |
| 385 | (structure) |
| 386 | (structure) |
| 387 | (structure) |
| 388 | (structure) |
| 389 | (structure) |

TABLE 1-continued

| Compound No. | Structure |
|---|---|
| 390 | 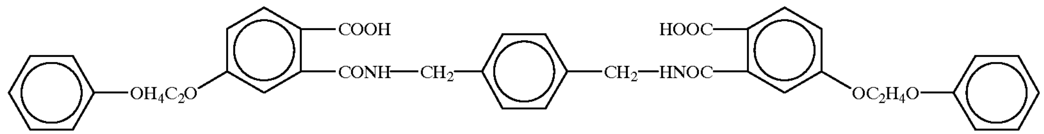 |
| 391 | 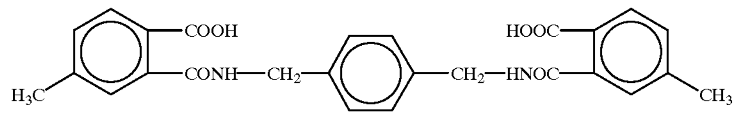 |
| 392 | 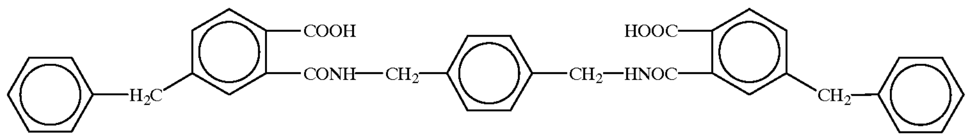 |
| 393 | 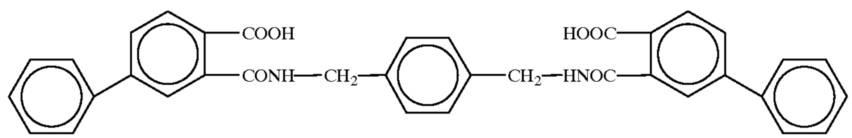 |
| 394 | 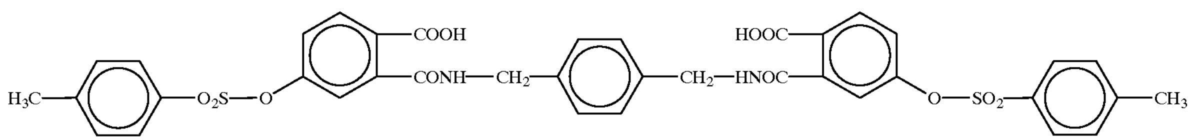 |
| 395 | 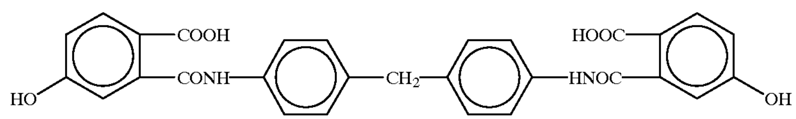 |

TABLE 1-continued

| Compound No. | Structure |
|---|---|
| 396 | 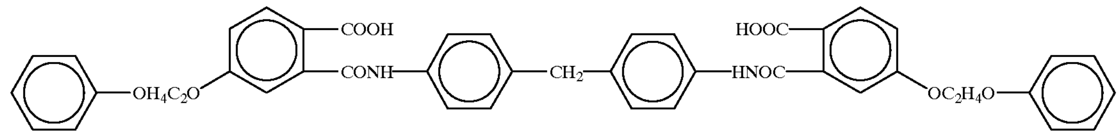 |
| 397 | 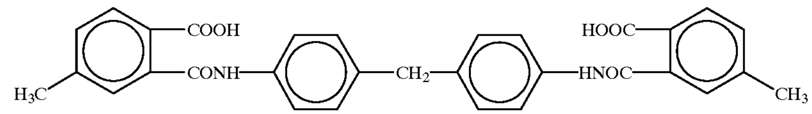 |
| 398 | 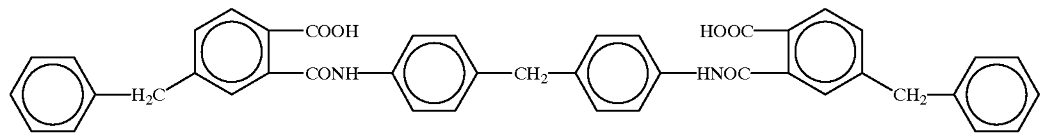 |
| 399 | 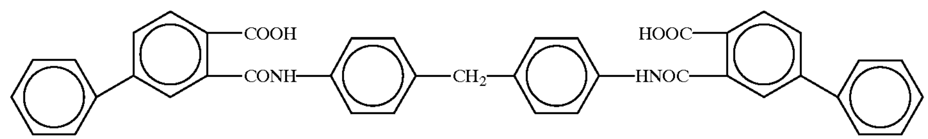 |
| 400 | 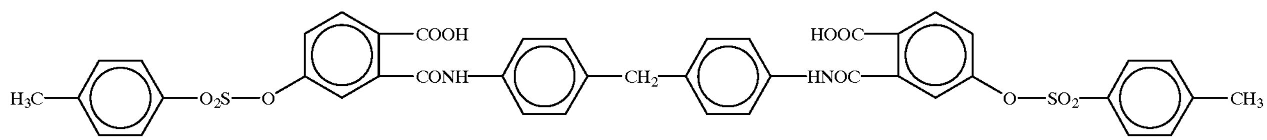 |
| 401 | 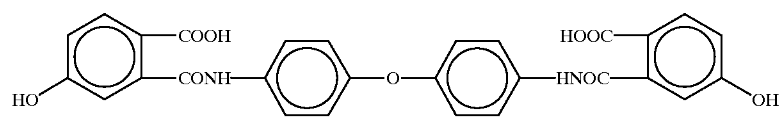 |

TABLE 1-continued

| Compound No. | Structure |
|---|---|
| 402 | 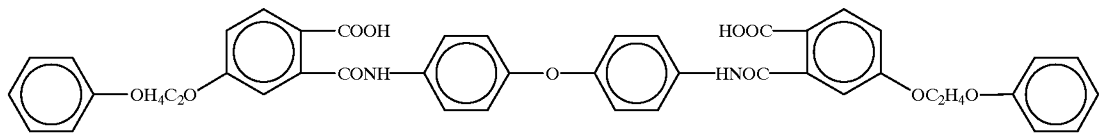 |
| 403 | 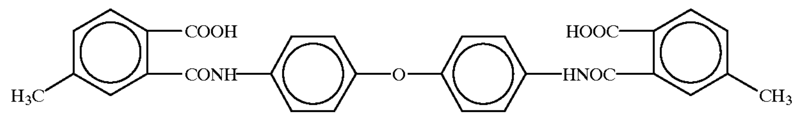 |
| 404 | 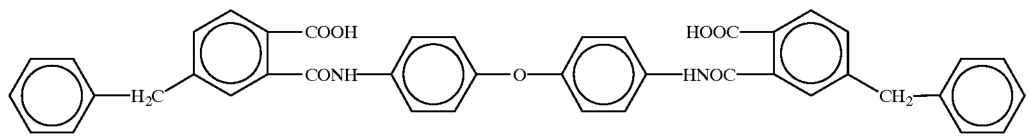 |
| 405 | 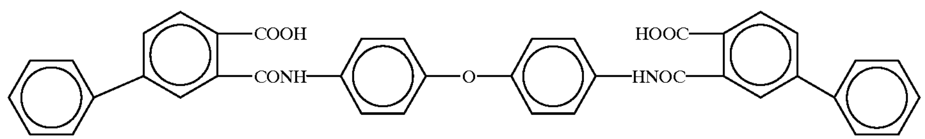 |
| 406 | 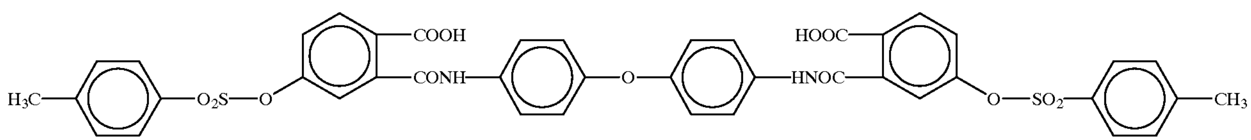 |
| 407 | 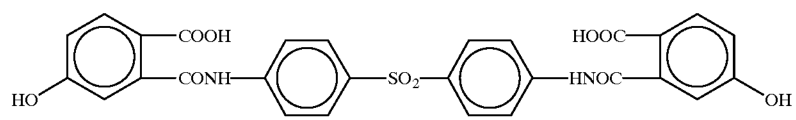 |

TABLE 1-continued

| Compound No. | Structure |
|---|---|
| 408 | (chemical structure) |
| 409 | (chemical structure) |
| 410 | (chemical structure) |
| 411 | (chemical structure) |
| 412 | (chemical structure) |
| 413 | (chemical structure) |

TABLE 1-continued

| Compound No. | Structure |
|---|---|
| 414 | 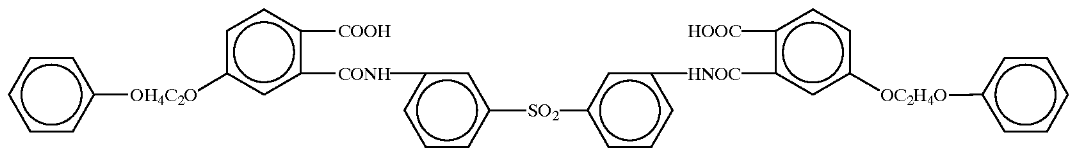 |
| 415 | 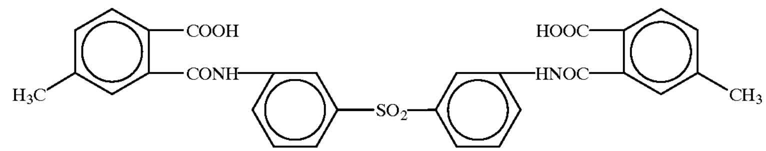 |
| 416 | 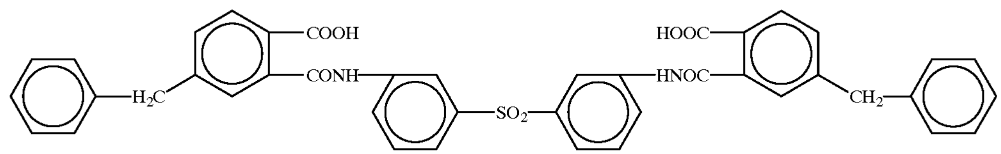 |
| 417 | 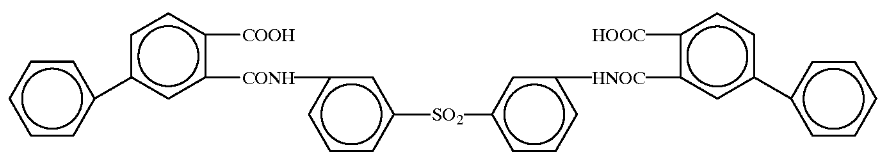 |
| 418 | 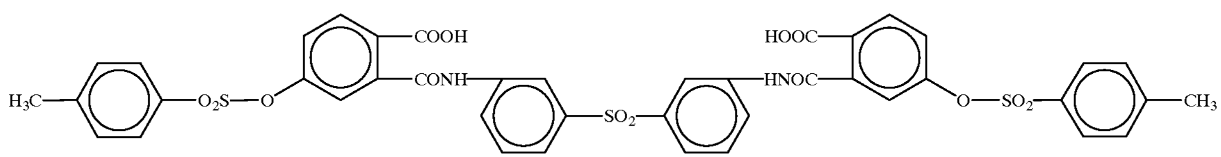 |
| 419 | 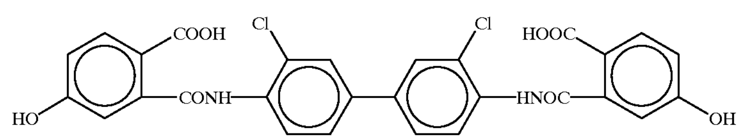 |

TABLE 1-continued

| Compound No. | Structure |
| --- | --- |
| 420 | 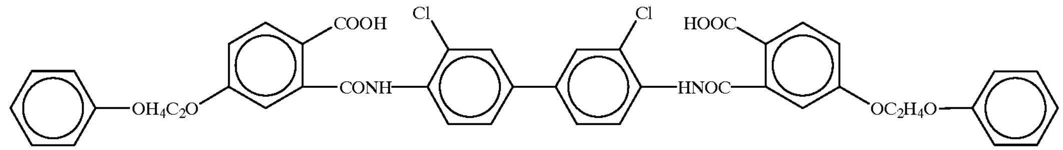 |
| 421 | 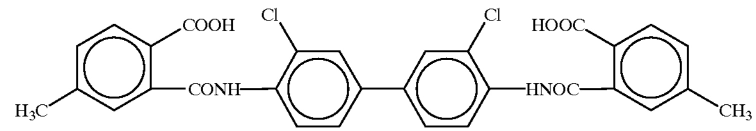 |
| 422 | 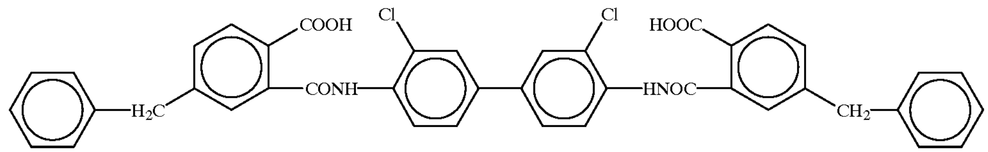 |
| 423 | 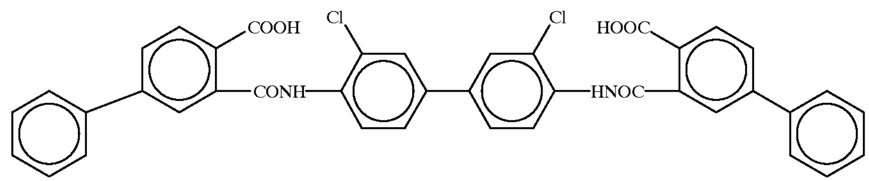 |
| 424 | 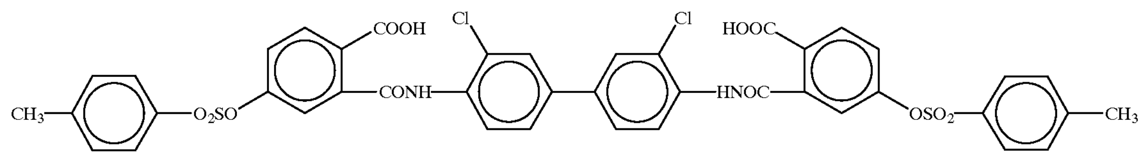 |
| 425 | 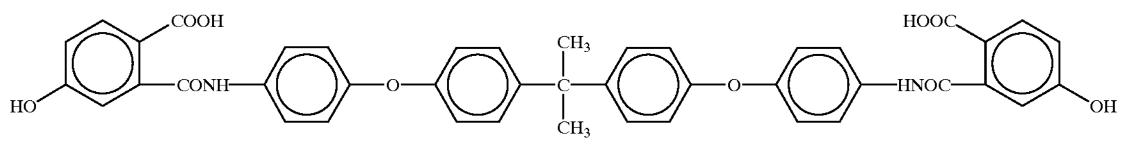 |

TABLE 1-continued

| Compound No. | Structure |
|---|---|
| 426 | (structure) |
| 427 | (structure) |
| 428 | (structure) |
| 429 | (structure) |
| 430 | (structure) |
| 431 | (structure) |

TABLE 1-continued

| Compound No. | Structure |
|---|---|
| 432 | 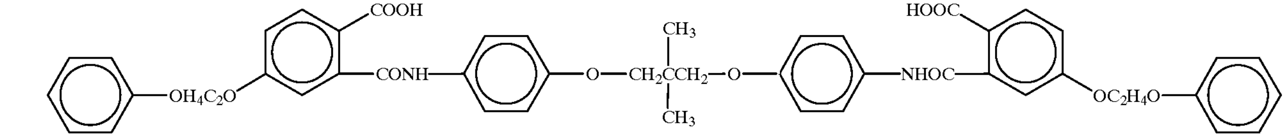 |
| 433 | 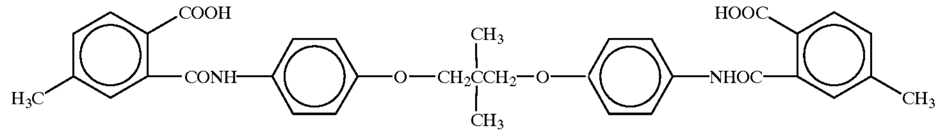 |
| 434 | 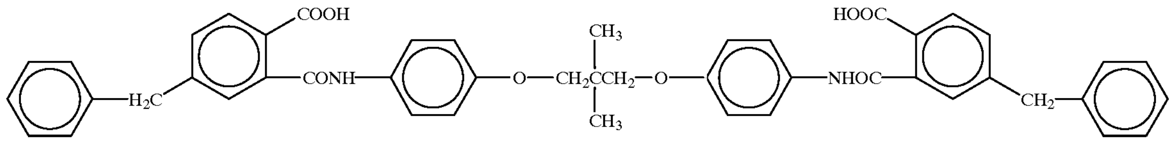 |
| 435 | 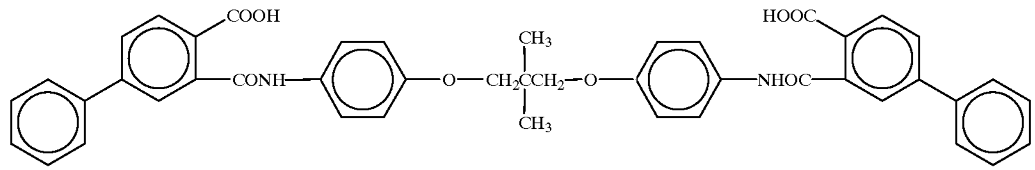 |
| 436 | 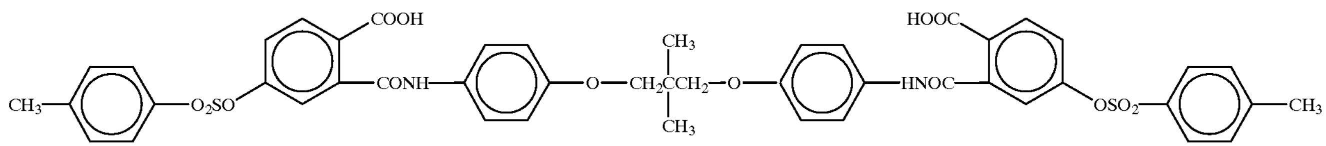 |
| 437 | 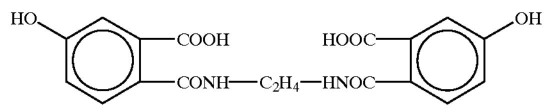 |

TABLE 1-continued

| Compound No. | Structure |
|---|---|
| 438 | (structure) |
| 439 | (structure) |
| 440 | (structure) |
| 441 | (structure) |
| 442 | (structure) |
| 443 | (structure) |
| 444 | (structure) |

TABLE 1-continued

| Compound No. | Structure |
|---|---|
| 445 | 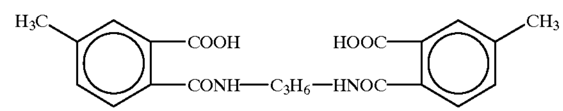 |
| 446 | 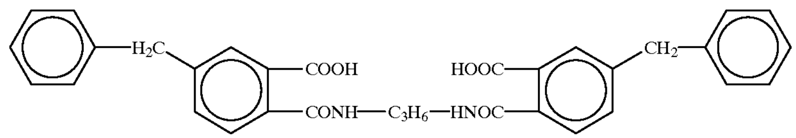 |
| 447 | 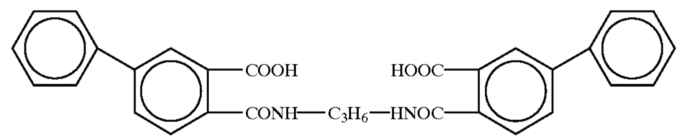 |
| 448 | 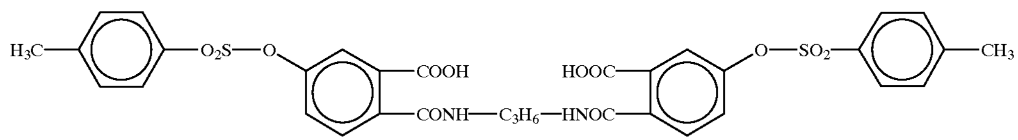 |
| 449 | 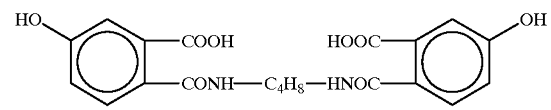 |
| 450 | 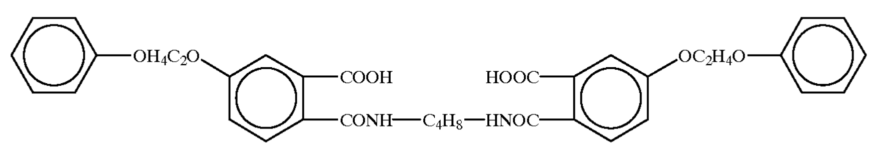 |
| 451 | 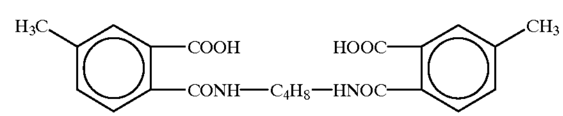 |

TABLE 1-continued

| Compound No. | Structure |
|---|---|
| 452 | 4-benzyl substituted benzene with COOH and CONH-C$_4$H$_8$-HNOC linked to 4-benzyl substituted benzene with HOOC and CONH-C$_4$H$_8$-HNOC |
| 453 | 4-phenyl substituted benzene with COOH and CONH-C$_4$H$_8$-HNOC linked to 4-phenyl substituted benzene with HOOC |
| 454 | 4-(4-methylphenylsulfonyloxy) benzene with COOH and CONH-C$_4$H$_8$-HNOC linked analogously |
| 455 | 4-hydroxy benzene with COOH and CONH-C$_6$H$_{12}$-HNOC linked to 4-hydroxy benzene with HOOC |
| 456 | 4-(2-phenoxyethoxy) benzene with COOH and CONH-C$_6$H$_{12}$-HNOC linked analogously |
| 457 | 4-methyl benzene with COOH and CONH-C$_6$H$_{12}$-HNOC linked to 4-methyl benzene with HOOC |

TABLE 1-continued

| Compound No. | Structure |
|---|---|
| 458 | (structure) |
| 459 | (structure) |
| 460 | (structure) |
| 461 | (structure) |
| 462 | (structure) |
| 463 | (structure) |

TABLE 1-continued

| Compound No. | Structure |
|---|---|
| 464 | 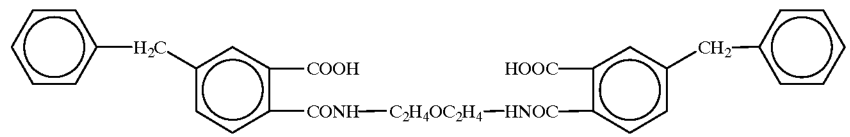 |
| 465 | 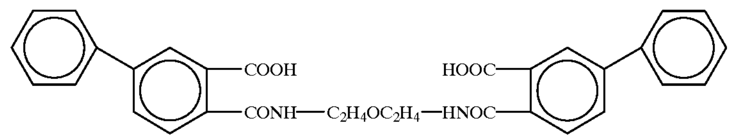 |
| 466 | 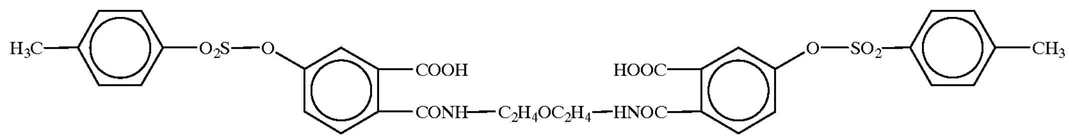 |
| 467 | 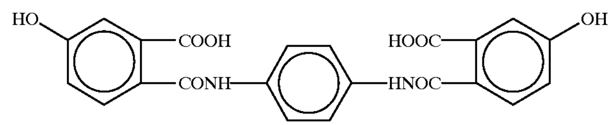 |
| 468 | 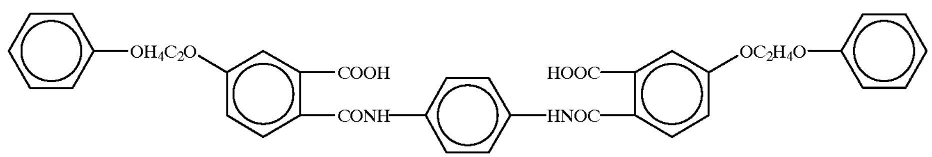 |
| 469 | 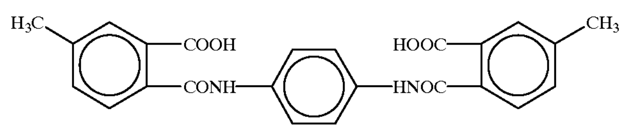 |

TABLE 1-continued

| Compound No. | Structure |
|---|---|
| 470 | 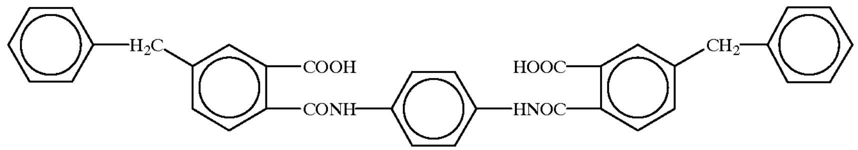 |
| 471 | 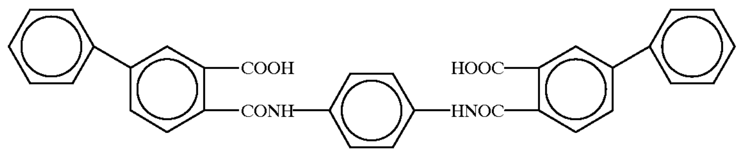 |
| 472 | 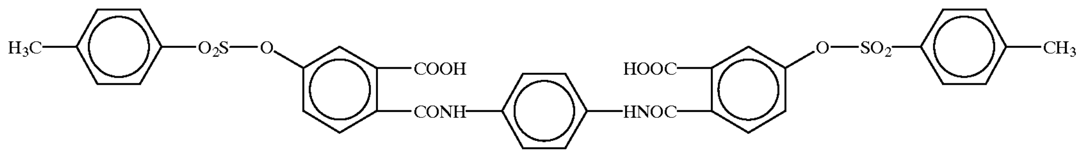 |
| 473 | 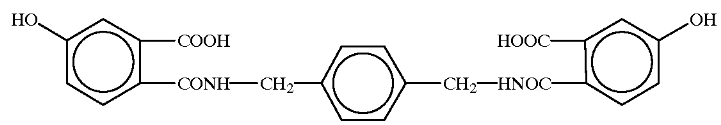 |
| 474 | 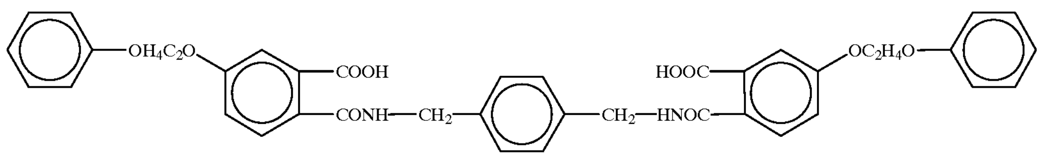 |
| 475 | 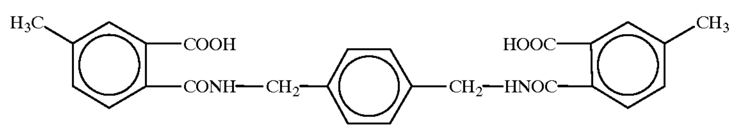 |

TABLE 1-continued

| Compound No. | Structure |
|---|---|
| 476 | 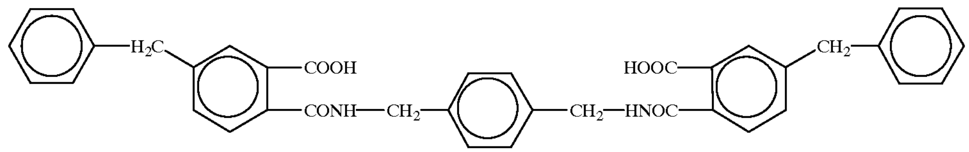 |
| 477 | 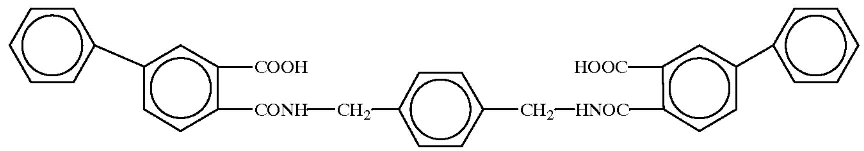 |
| 478 | 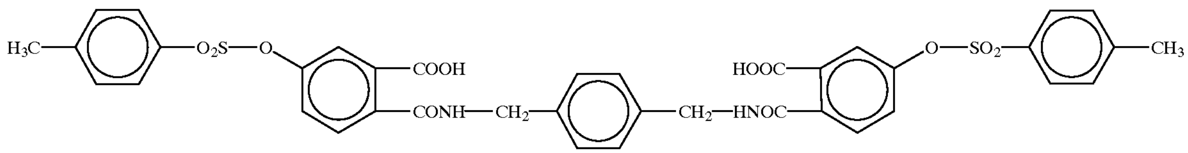 |
| 479 | 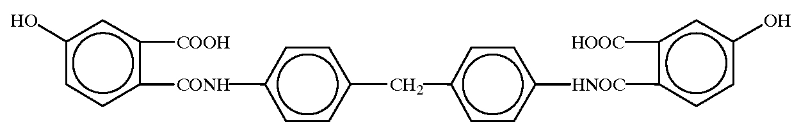 |
| 480 | 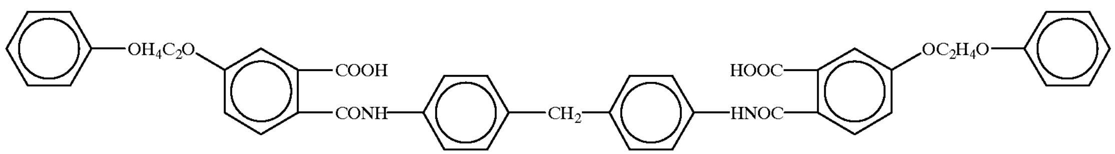 |
| 481 | 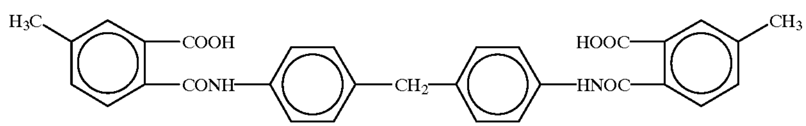 |

TABLE 1-continued
| Compound No. | Structure |
|---|---|
| 482 | 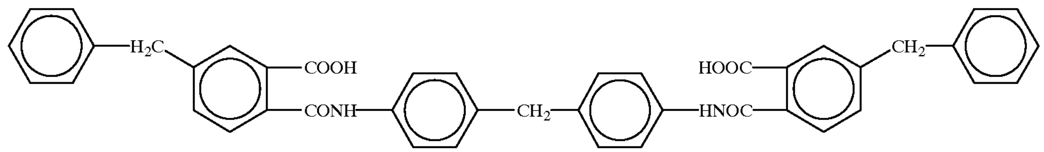 |
| 483 | 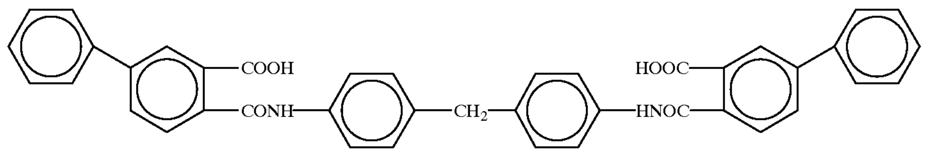 |
| 484 | 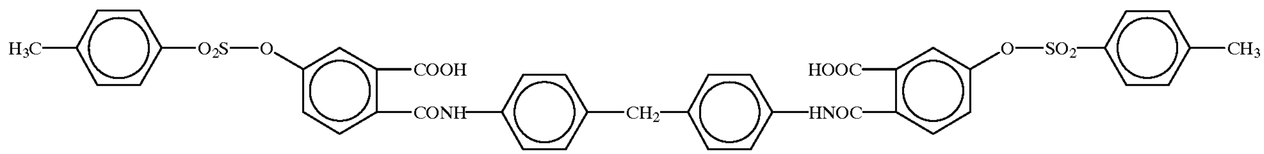 |
| 485 | 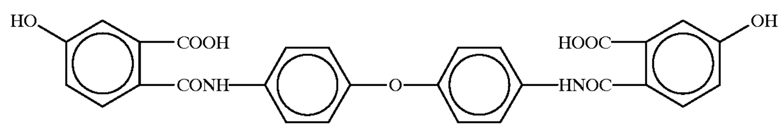 |
| 486 | 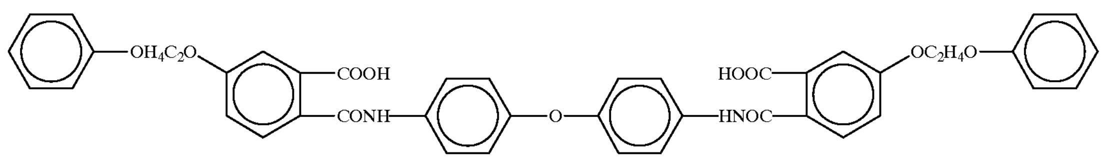 |
| 487 | 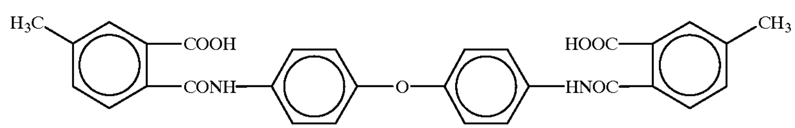 |

TABLE 1-continued

| Compound No. | Structure |
|---|---|
| 488 | (structure) |
| 489 | (structure) |
| 490 | (structure) |
| 491 | (structure) |
| 492 | (structure) |
| 493 | (structure) |

TABLE 1-continued

| Compound No. | Structure |
|---|---|
| 494 | 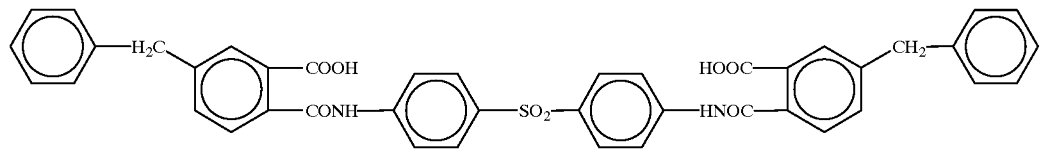 |
| 495 | 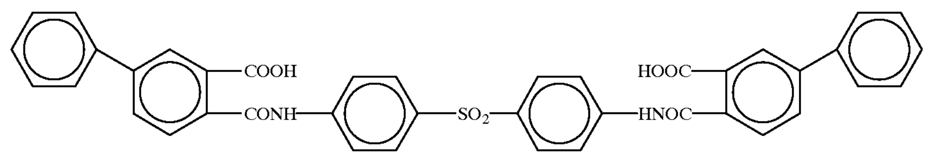 |
| 496 | 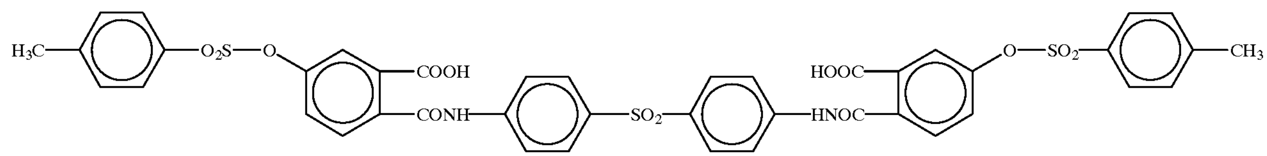 |
| 497 | 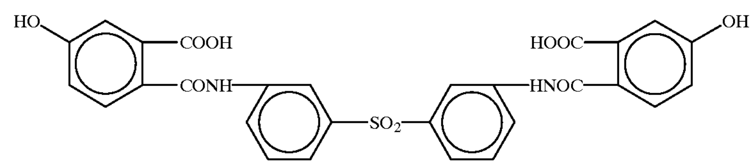 |
| 498 | 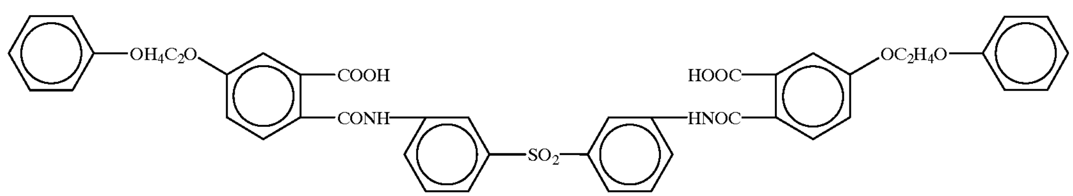 |

TABLE 1-continued

| Compound No. | Structure |
|---|---|
| 499 | 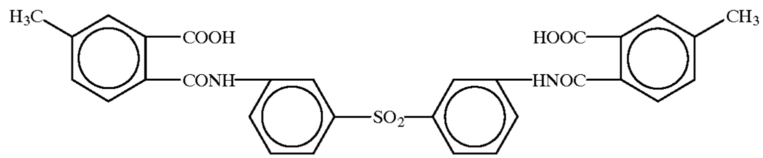 |
| 500 | 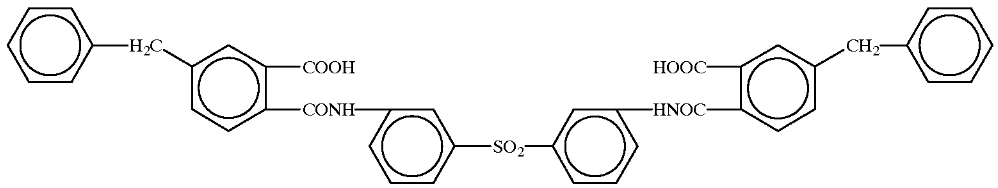 |
| 501 | 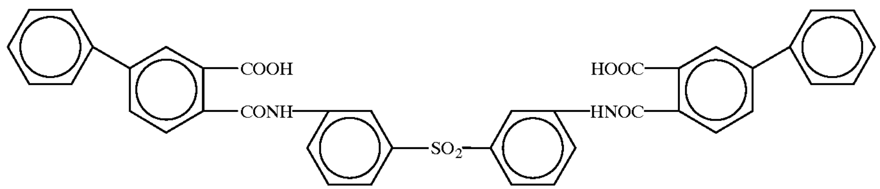 |
| 502 | 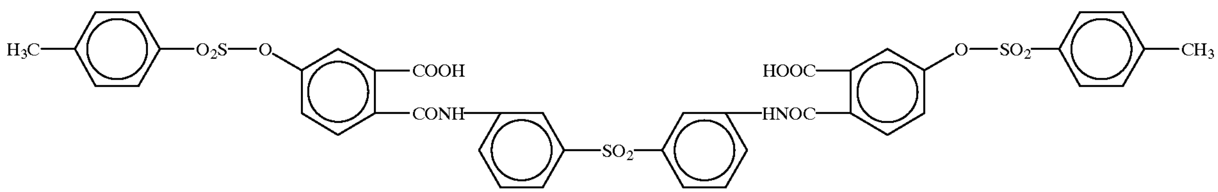 |
| 503 | 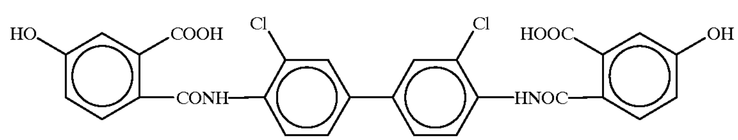 |

TABLE 1-continued

| Compound No. | Structure |
|---|---|
| 504 | 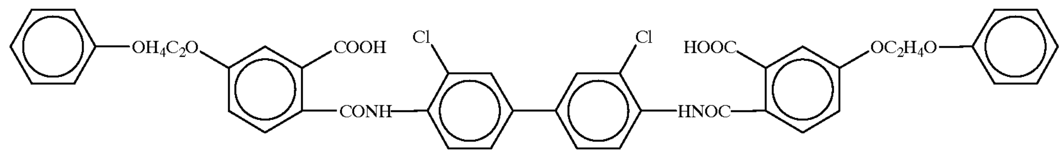 |
| 505 | 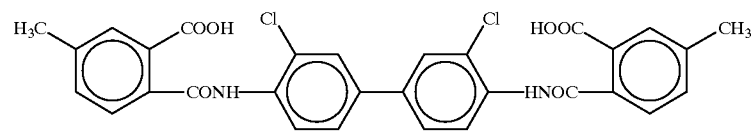 |
| 506 | 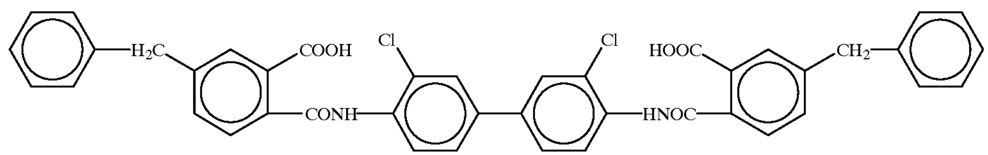 |
| 507 | 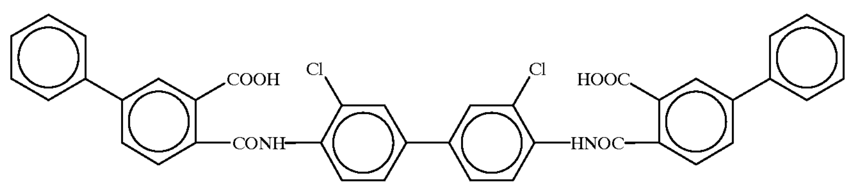 |
| 508 | 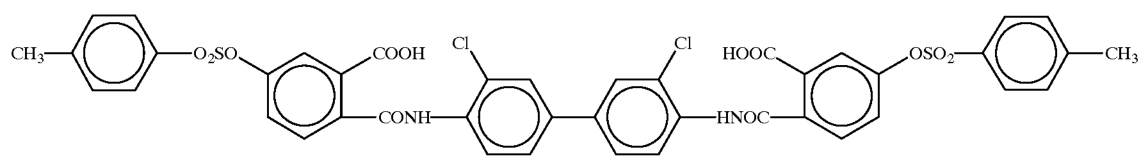 |
| 509 | 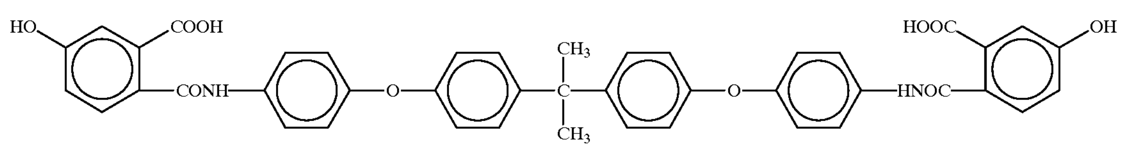 |

TABLE 1-continued

| Compound No. | Structure |
|---|---|
| 510 | (structure) |
| 511 | (structure) |
| 512 | (structure) |
| 513 | (structure) |
| 514 | (structure) |

TABLE 1-continued

| Compound No. | Structure |
|---|---|
| 515 | (structure) |
| 516 | (structure) |
| 517 | (structure) |
| 518 | (structure) |
| 519 | (structure) |

TABLE 1-continued

| Compound No. | Structure |
|---|---|
| 520 | (structure) |
| 521 | (structure) |
| 522 | (structure) |
| 523 | (structure) |
| 524 | (structure) |
| 525 | (structure) |
| 526 | (structure) |

TABLE 1-continued

| Compound No. | Structure |
|---|---|
| 527 | 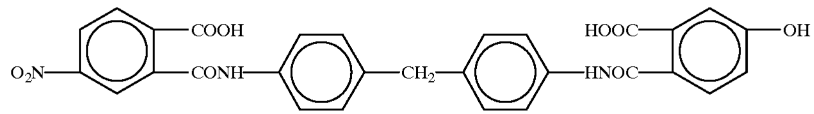 |
| 528 | 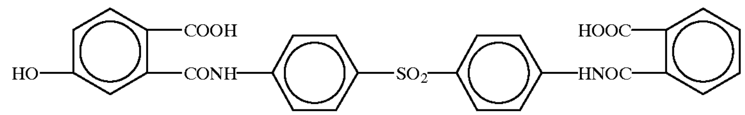 |
| 529 | 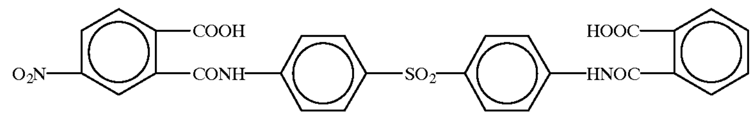 |
| 530 | 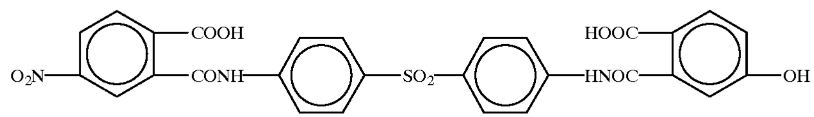 |
| 531 | 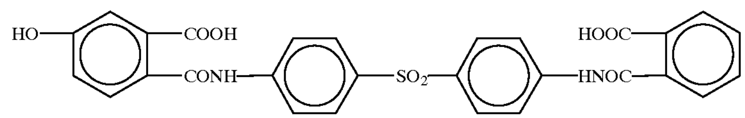 |
| 532 | 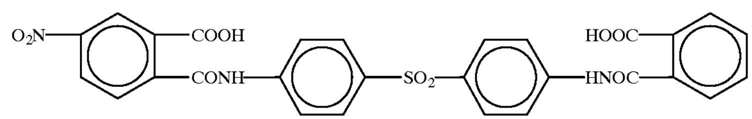 |
| 533 | 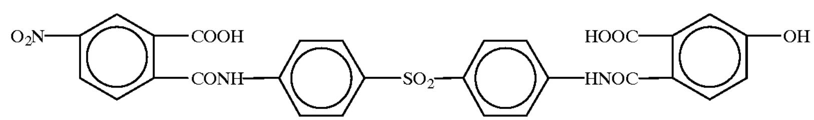 |

TABLE 1-continued

| Compound No. | Structure |
|---|---|
| 534 | (structure) |
| 535 | (structure) |
| 536 | (structure) |
| 537 | (structure) |
| 538 | (structure) |
| 539 | (structure) |
| 540 | (structure) |

TABLE 1-continued

| Compound No. | Structure |
|---|---|
| 541 | 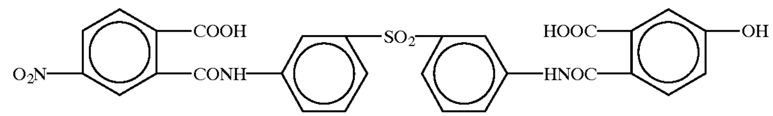 |
| 542 | 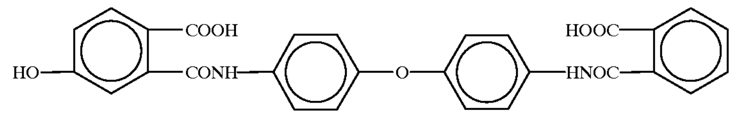 |
| 543 | 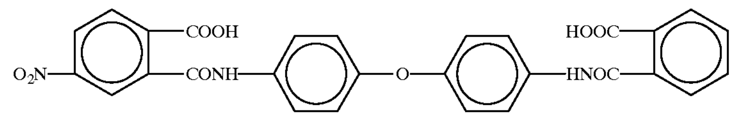 |
| 544 | 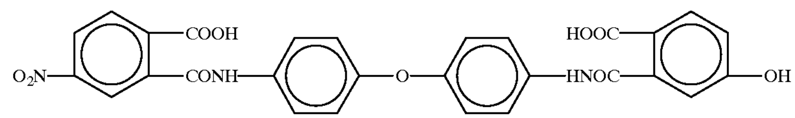 |
| 545 | 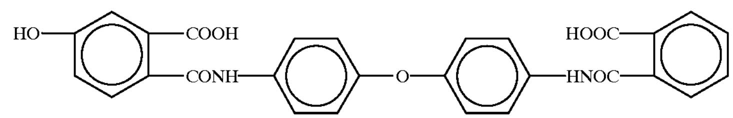 |
| 546 | 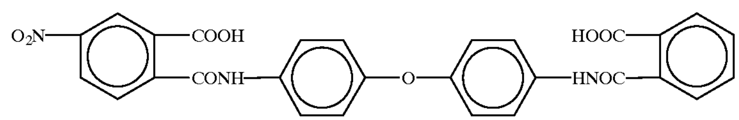 |
| 547 | 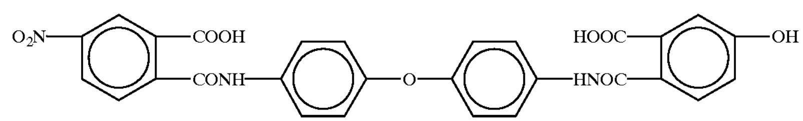 |

TABLE 1-continued

| Compound No. | Structure |
|---|---|
| 548 | (structure) |
| 549 | (structure) |
| 550 | (structure) |
| 551 | (structure) |
| 552 | (structure) |
| 553 | (structure) |
| 554 | (structure) |
| 555 | (structure) |

TABLE 1-continued

| Compound No. | Structure |
|---|---|
| 556 | HO–C6H4–COOH / CONH–C3H6–HNOC–C6H5 (HOOC) |
| 557 | O2N–C6H4–COOH / CONH–C3H6–HNOC–C6H5 (HOOC) |
| 558 | O2N–C6H4–COOH / CONH–C3H6–HNOC–C6H4–OH (HOOC) |
| 559 | HO–C6H4–COOH / CONH–C3H6–HNOC–C6H5 (HOOC) |
| 560 | O2N–C6H4–COOH / CONH–C3H6–HNOC–C6H5 (HOOC) |
| 561 | O2N–C6H4–COOH / CONH–C3H6–HNOC–C6H4–OH (HOOC) |
| 562 | O2N–C6H4–COOH / CONH–C3H6–HNOC–C6H4–OH (HOOC) |
| 563 | HO–C6H4–COOH / CONH–C4H8–HNOC–C6H5 (HOOC) |

TABLE 1-continued
| Compound No. | Structure |
|---|---|
| 564 | 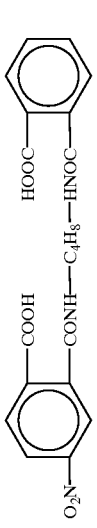 |
| 565 | 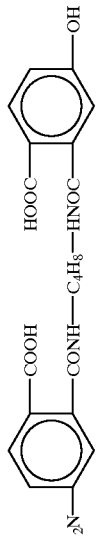 |
| 566 | 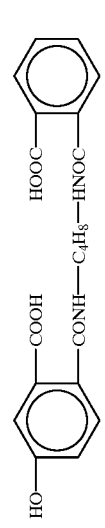 |
| 567 | 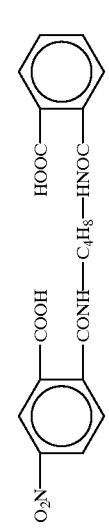 |
| 568 | 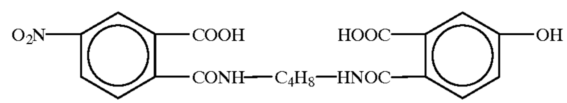 |
| 569 | 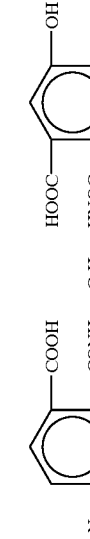 |
| 570 | 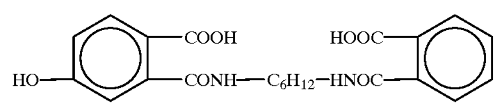 |
| 571 | 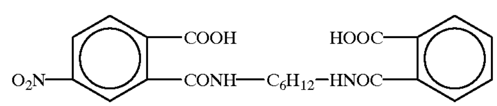 |

TABLE 1-continued

| Compound No. | Structure |
|---|---|
| 572 | (4-O₂N-C₆H₄)-COOH, CONH-C₆H₁₂-HNOC-(2-HOOC-C₆H₃-4-OH) |
| 573 | (4-HO-C₆H₄)-COOH, CONH-C₆H₁₂-HNOC-C₆H₄ |
| 574 | (4-O₂N-C₆H₄)-COOH, CONH-C₆H₁₂-HNOC-C₆H₄ |
| 575 | (4-O₂N-C₆H₄)-COOH, CONH-C₆H₁₂-HNOC-(2-HOOC-C₆H₃-4-OH) |
| 576 | (4-O₂N-C₆H₄)-COOH, CONH-C₆H₁₂-HNOC-(2-HOOC-C₆H₃-4-OH) |
| 577 | (4-HO-C₆H₃-2-COOH)-CONH-C₆H₄-OCH₂C(CH₃)₂CH₂O-C₆H₄-CONH-(2-HOOC-C₆H₄) |
| 578 | (4-O₂N-C₆H₃-2-COOH)-CONH-C₆H₄-OCH₂C(CH₃)₂CH₂O-C₆H₄-CONH-(2-HOOC-C₆H₄) |

TABLE 1-continued

| Compound No. | Structure |
|---|---|
| 579 | (structure) |
| 580 | (structure) |
| 581 | (structure) |
| 582 | (structure) |
| 583 | (structure) |
| 584 | (structure) |

TABLE 1-continued

| Compound No. | Structure |
|---|---|
| 585 | (structure) |
| 586 | (structure) |
| 587 | (structure) |
| 588 | (structure) |
| 589 | (structure) |
| 590 | (structure) |
| 591 | (structure) |

TABLE 1-continued

| Compound No. | Structure |
|---|---|
| 592 | (structure) |
| 593 | (structure) |
| 594 | (structure) |
| 595 | (structure) |
| 596 | (structure) |
| 597 | (structure) |
| 598 | (structure) |

TABLE 1-continued

| Compound No. | Structure |
|---|---|
| 599 | (structure) |
| 600 | (structure) |
| 601 | (structure) |
| 602 | (structure) |
| 603 | (structure) |
| 604 | (structure) |
| 605 | (structure) |

TABLE 1-continued

| Compound No. | Structure |
|---|---|
| 606 | 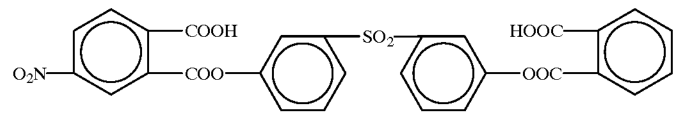 |
| 607 | 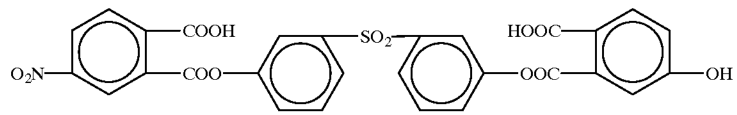 |
| 608 | 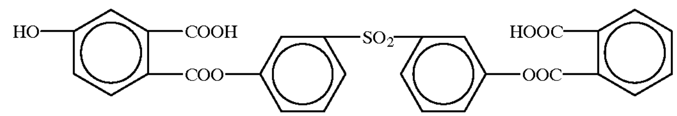 |
| 609 | 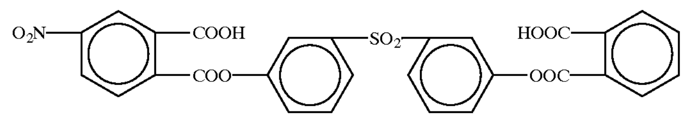 |
| 610 | 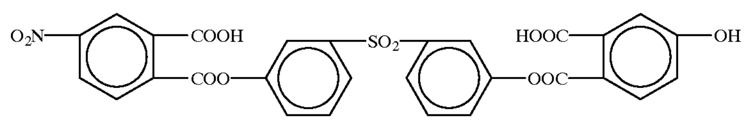 |
| 611 | 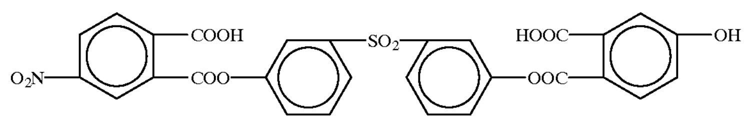 |
| 612 | 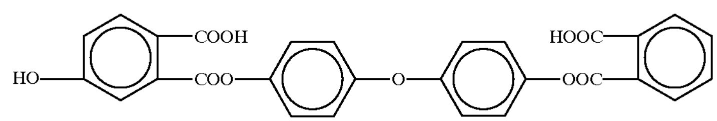 |

TABLE 1-continued

| Compound No. | Structure |
|---|---|
| 613 | 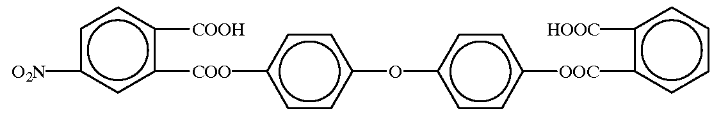 |
| 614 | 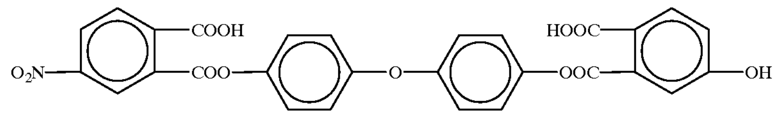 |
| 615 | 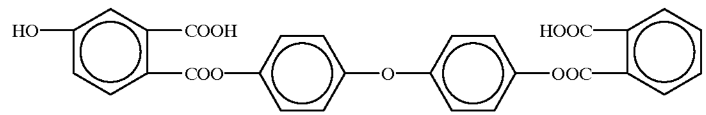 |
| 616 | 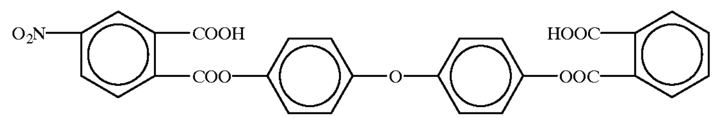 |
| 617 | 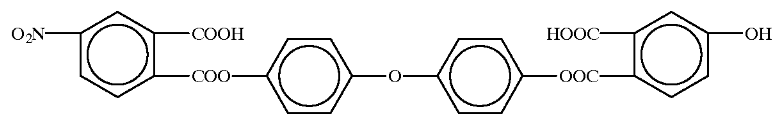 |
| 618 | 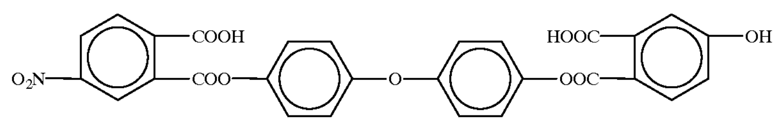 |
| 619 | 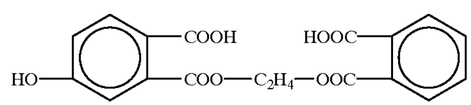 |

TABLE 1-continued

| Compound No. | Structure |
|---|---|
| 620 | (O2N-phenyl)-COOH, COO-C2H4-OOC-(phenyl)-COOH |
| 621 | (O2N-phenyl)-COOH, COO-C2H4-OOC-(phenyl)-OH |
| 622 | (HO-phenyl)-COOH, COO-C2H4-OOC-(phenyl)-COOH |
| 623 | (O2N-phenyl)-COOH, COO-C2H4-OOC-(phenyl)-COOH |
| 624 | (O2N-phenyl)-COOH, COO-C2H4-OOC-(phenyl)-OH |
| 625 | (O2N-phenyl)-COOH, COO-C2H4-OOC-(phenyl)-OH |
| 626 | (HO-phenyl)-COOH, COO-C3H6-OOC-(phenyl)-COOH |
| 627 | (O2N-phenyl)-COOH, COO-C3H6-OOC-(phenyl)-COOH |

TABLE 1-continued
| Compound No. | Structure |
|---|---|
| 628 | 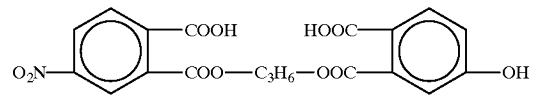 |
| 629 | 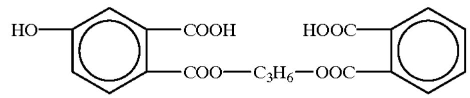 |
| 630 | 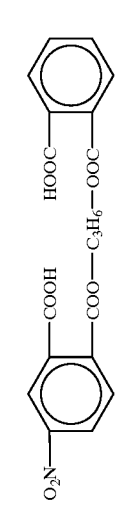 |
| 631 | 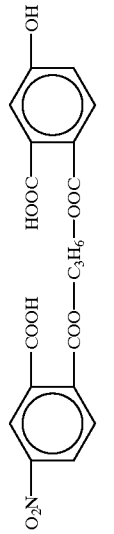 |
| 632 | 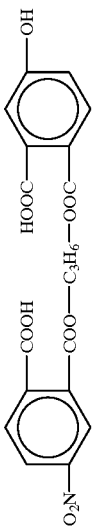 |
| 633 | 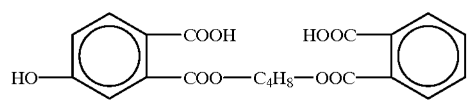 |
| 634 | 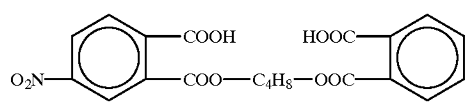 |
| 635 | 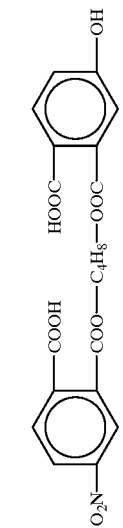 |

TABLE 1-continued

| Compound No. | Structure |
|---|---|
| 636 | HO–⟨C6H4⟩(COOH)–COO–C4H8–OOC–⟨C6H4⟩(COOH) |
| 637 | O2N–⟨C6H4⟩(COOH)–COO–C4H8–OOC–⟨C6H4⟩(COOH) |
| 638 | O2N–⟨C6H4⟩(COOH)–COO–C4H8–OOC–⟨C6H4⟩(OH) |
| 639 | O2N–⟨C6H4⟩(COOH)–COO–C4H8–OOC–⟨C6H4⟩(OH) |
| 640 | HO–⟨C6H4⟩(COOH)–COO–C6H12–OOC–⟨C6H4⟩(COOH) |
| 641 | O2N–⟨C6H4⟩(COOH)–COO–C6H12–OOC–⟨C6H4⟩(COOH) |
| 642 | O2N–⟨C6H4⟩(COOH)–COO–C6H12–OOC–⟨C6H4⟩(OH) |
| 643 | HO–⟨C6H4⟩(COOH)–COO–C6H12–OOC–⟨C6H4⟩(OH) |

TABLE 1-continued

| Compound No. | Structure |
|---|---|
| 644 | [structure] |
| 645 | [structure] |
| 646 | [structure] |
| 647 | [structure] |
| 648 | [structure] |
| 649 | [structure] |
| 650 | [structure] |

TABLE 1-continued

| Compound No. | Structure |
|---|---|
| 651 | 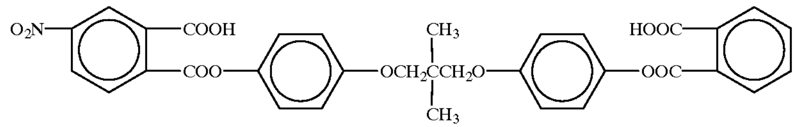 |
| 652 | 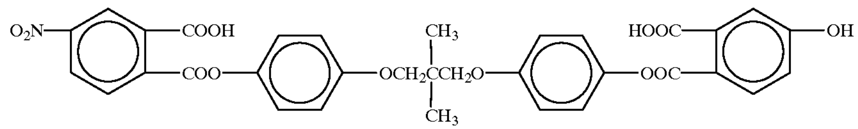 |
| 653 | 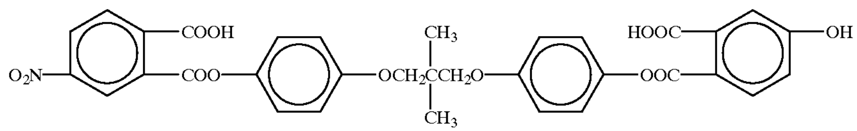 |
| 654 | 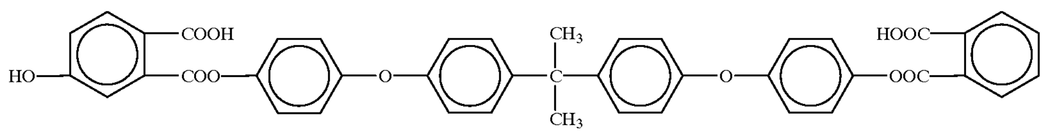 |
| 655 | 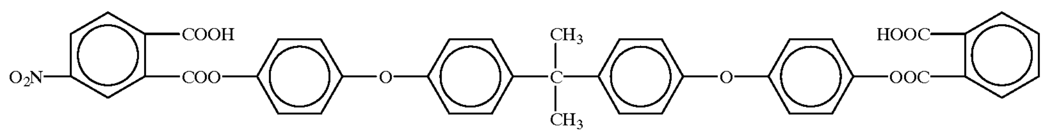 |
| 656 | 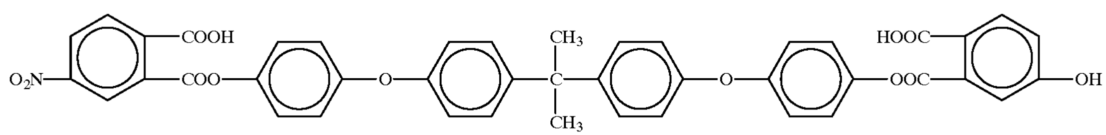 |

TABLE 1-continued

| Compound No. | Structure |
|---|---|
| 657 | (structure) |
| 658 | (structure) |
| 659 | (structure) |
| 660 | (structure) |
| 661 | (structure) |
| 662 | (structure) |

TABLE 1-continued

| Compound No. | Structure |
|---|---|
| 663 | (structure) |
| 664 | (structure) |
| 665 | (structure) |
| 666 | (structure) |
| 667 | (structure) |
| 668 | (structure) |

TABLE 1-continued

| Compound No. | Structure |
|---|---|
| 669 | (structure) |
| 670 | (structure) |
| 671 | (structure) |
| 672 | (structure) |
| 673 | (structure) |
| 674 | (structure) |

TABLE 1-continued

| Compound No. | Structure |
|---|---|
| 675 | (structure) |
| 676 | (structure) |
| 677 | (structure) |
| 678 | (structure) |
| 679 | (structure) |
| 680 | (structure) |
| 681 | (structure) |
| 682 | (structure) |

TABLE 1-continued

| Compound No. | Structure |
|---|---|
| 683 | 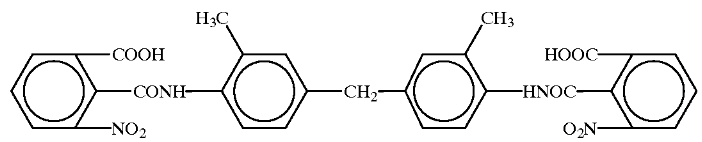 |
| 684 | 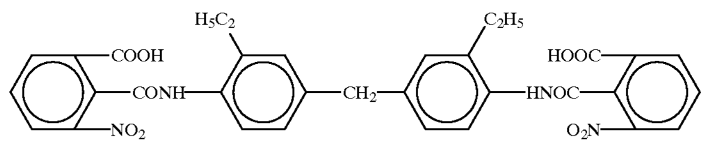 |
| 685 | 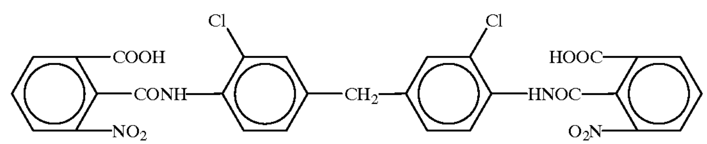 |
| 686 | 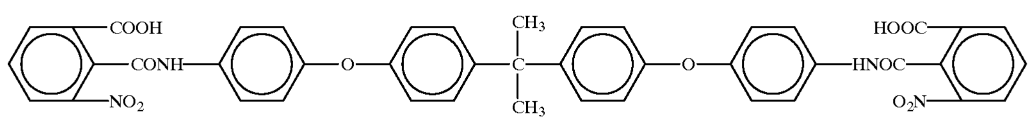 |
| 687 | 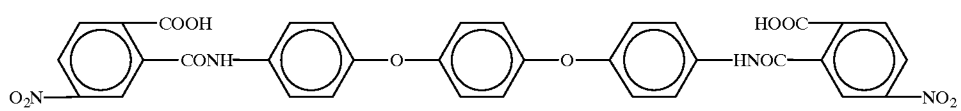 |
| 688 | 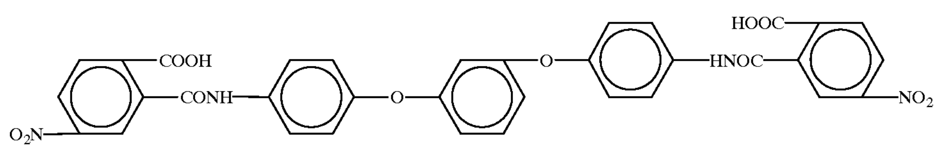 |
| 689 | 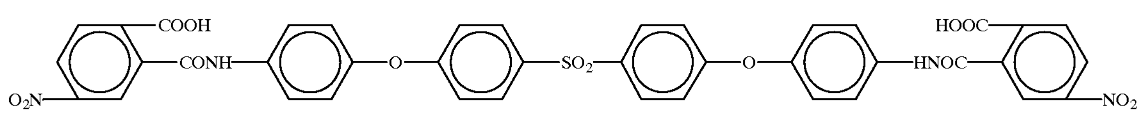 |

TABLE 1-continued

| Compound No. | Structure |
|---|---|
| 690 | (structure) |
| 691 | (structure) |
| 692 | (structure) |
| 693 | (structure) |
| 694 | (structure) |
| 695 | (structure) |
| 696 | (structure) |

TABLE 1-continued

| Compound No. | Structure |
|---|---|
| 697 | 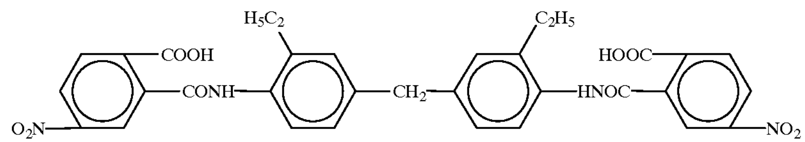 |
| 698 | 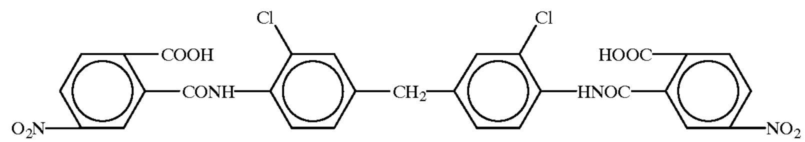 |
| 699 | 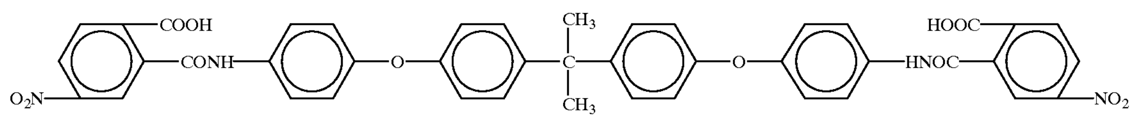 |
| 700 | 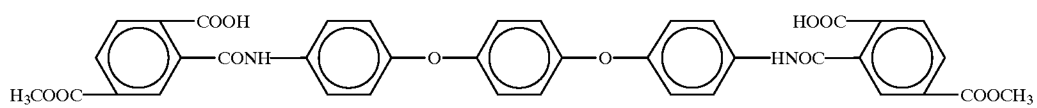 |
| 701 | 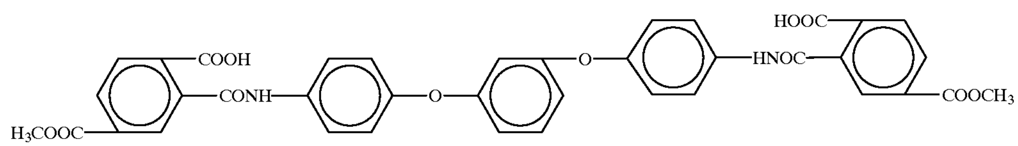 |
| 702 | 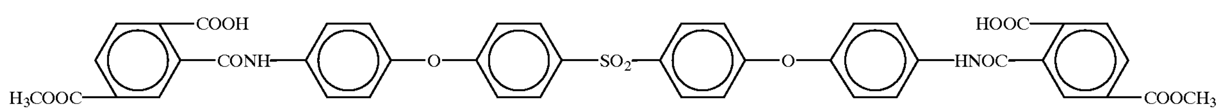 |
| 703 | 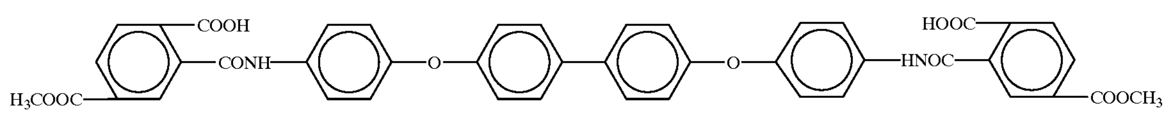 |

TABLE 1-continued

| Compound No. | Structure |
|---|---|
| 704 | (structure) |
| 705 | (structure) |
| 706 | (structure) |
| 707 | (structure) |
| 708 | (structure) |
| 709 | (structure) |
| 710 | (structure) |
| 711 | (structure) |

TABLE 1-continued

| Compound No. | Structure |
|---|---|
| 712 | (structure) |
| 713 | (structure) |
| 714 | (structure) |
| 715 | (structure) |
| 716 | (structure) |
| 717 | (not used) |
| 718 | (structure) |

TABLE 1-continued

| Compound No. | Structure |
|---|---|
| 719 | 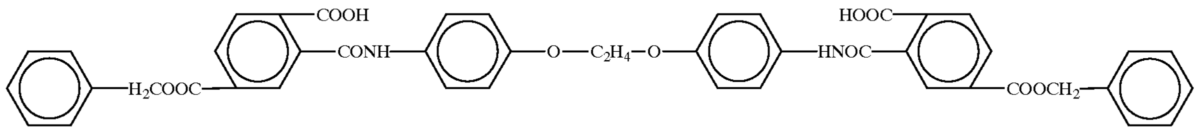 |
| 720 | 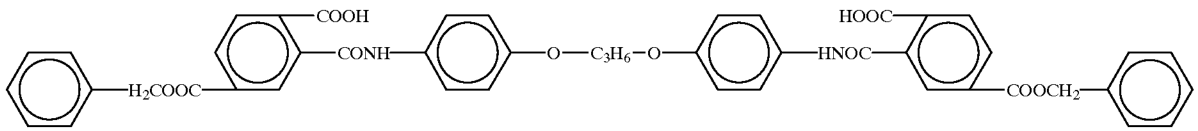 |
| 721 | 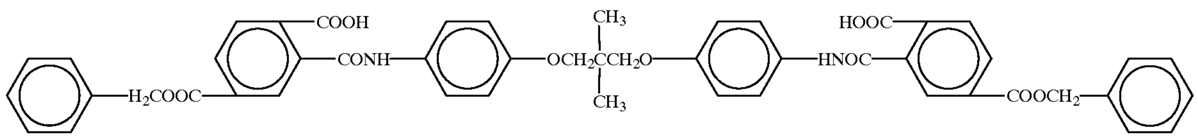 |
| 722 | 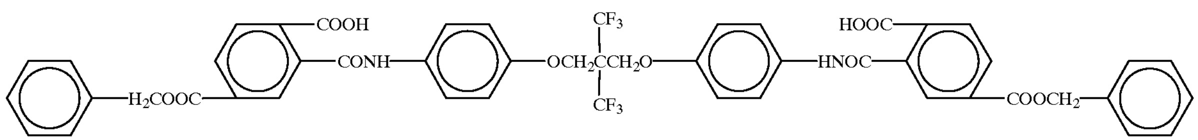 |
| 723 | 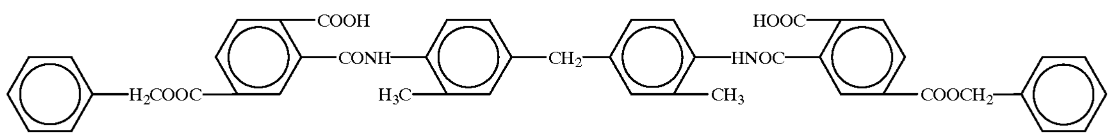 |
| 724 | 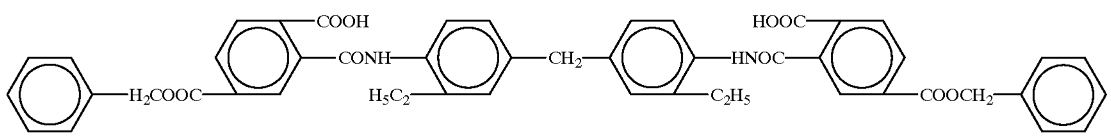 |
| 725 | 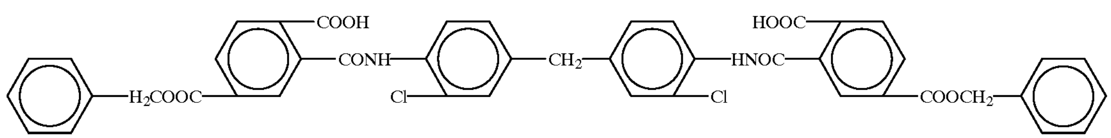 |

TABLE 1-continued

| Compound No. | Structure |
|---|---|
| 726 | (structure) |
| 727 | (structure) |
| 728 | (structure) |
| 729 | (structure) |
| 730 | (structure) |
| 731 | (structure) |
| 732 | (structure) |
| 733 | (structure) |

TABLE 1-continued

| Compound No. | Structure |
|---|---|
| 734 | (chemical structure) |
| 735 | (chemical structure) |
| 736 | (chemical structure) |
| 737 | (chemical structure) |
| 738 | (chemical structure) |
| 739 | (chemical structure) |
| 740 | (chemical structure) |

TABLE 1-continued

| Compound No. | Structure |
|---|---|
| 741 | (structure) |
| 742 | (structure) |
| 743 | (structure) |
| 744 | (structure) |
| 745 | (structure) |
| 746 | (structure) |
| 747 | (structure) |
| 748 | (structure) |

TABLE 1-continued

| Compound No. | Structure |
|---|---|
| 749 | 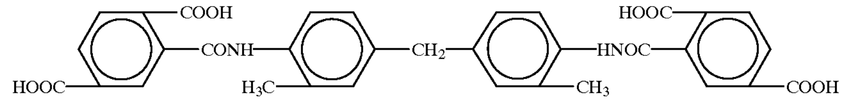 |
| 750 | 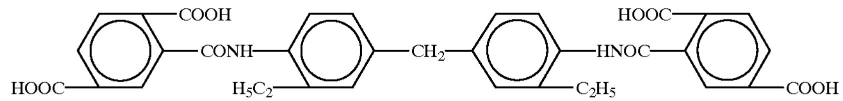 |
| 751 | 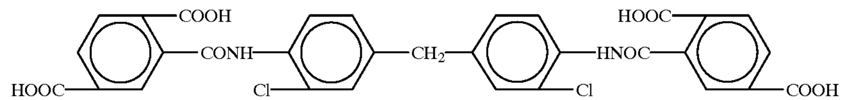 |
| 752 | 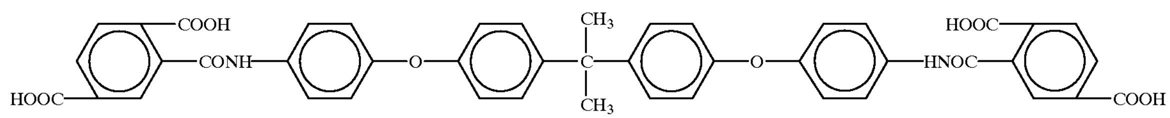 |
| 753 | 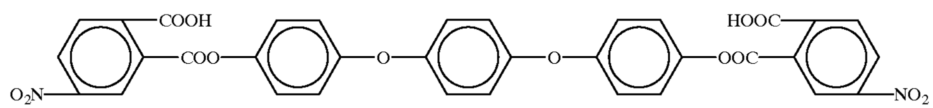 |
| 754 | 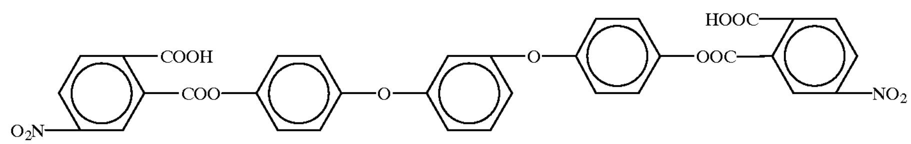 |
| 755 | 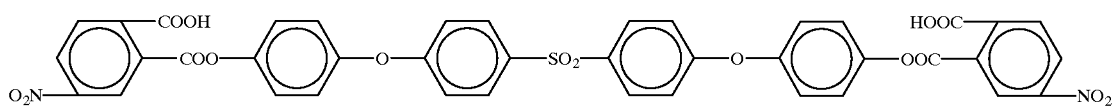 |
| 756 | 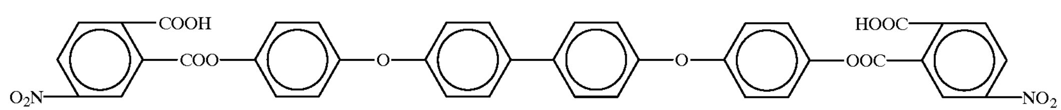 |

TABLE 1-continued

| Compound No. | Structure |
|---|---|
| 757 | 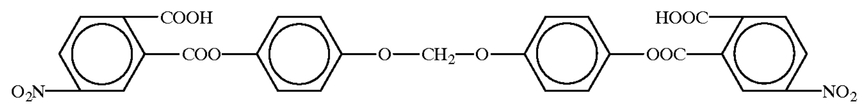 |
| 758 | 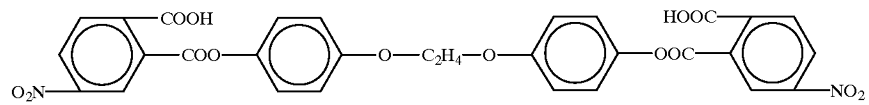 |
| 759 | 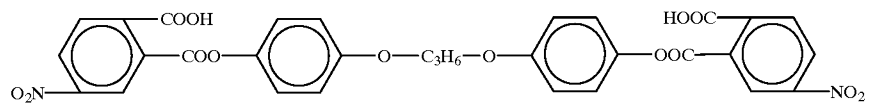 |
| 760 | 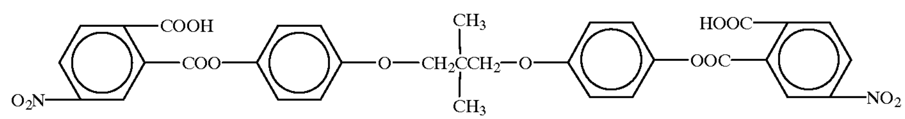 |
| 761 | 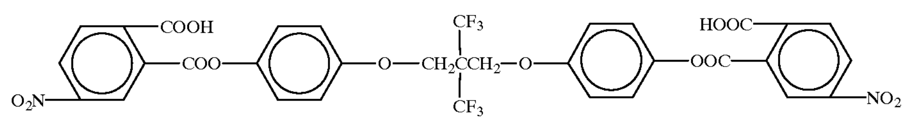 |
| 762 | 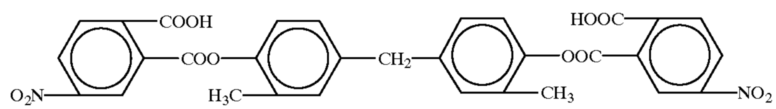 |
| 763 | 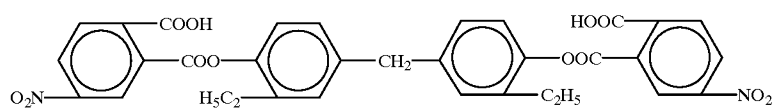 |
| 764 | 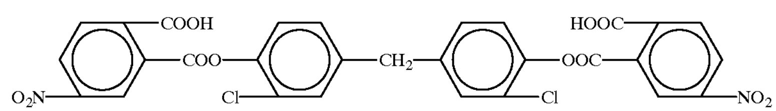 |

TABLE 1-continued

| Compound No. | Structure |
|---|---|
| 765 | (structure) |
| 766 | (structure) |
| 767 | (structure) |
| 768 | (structure) |
| 769 | (structure) |
| 770 | (structure) |
| 771 | (structure) |
| 772 | (structure) |

TABLE 1-continued

| Compound No. | Structure |
|---|---|
| 773 | (structure) |
| 774 | (structure) |
| 775 | (structure) |
| 776 | (structure) |
| 777 | (structure) |
| 778 | (structure) |

The aromatic carboxylic acid compounds represented by formula (I) according to the present invention are novel compounds. When the compounds of formula (I) are used as the color developers in the thermosensitive recording material, the oil resistance, the plasticizer resistance and the heat resistance of an image area formed in the recording material are improved. The reason for this improvement has not been clarified, but it is considered that the following factors (1) to (4) contribute to the improvement of the preservation stability of the recorded image area:

(1) The affinity of the color developer for a leuco dye is increased when an electron-donating group is present in the above-mentioned compound of formula (I).

(2) When the compound of formula (I) has a substituent such as an electron-attracting group, the compound becomes a strong acid, and the color development performance of the compound is improved.

(3) Since two or more aromatic carboxylic acid moieties are contained in one molecule of the color developer compound, the molecular weight is increased, and therefore, the solubility of the color developer in plasticizers is decreased.

(4) Since two or more aromatic carboxylic acid moieties are contained in one molecule of the color developer compound, the molecule of the color developer becomes so bulky as to surround a molecule of a leuco dye compound.

The aromatic carboxylic acid compound of formula (I) can be produced in accordance with the following reaction scheme:

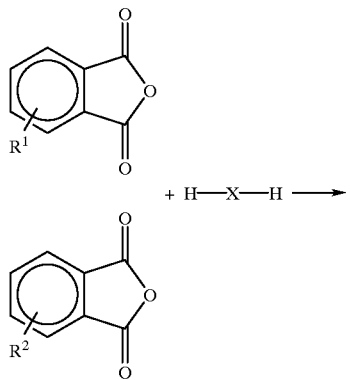

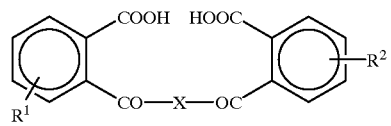

wherein $R^1$, $R^2$ and X are the same as those previously defined.

In the present invention, an aromatic carboxylic acid compound of formula (I') can be produced by allowing a nitrophthalic anhydride of formula (II) to react with a compound of formula (III):

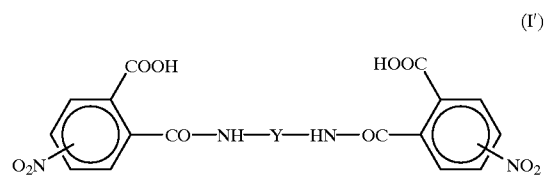

(I')

wherein Y is an alkylene group having 2 to 12 carbon atoms, a xylylene group,

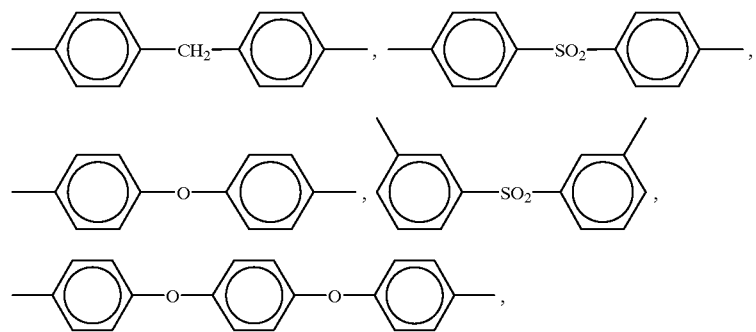

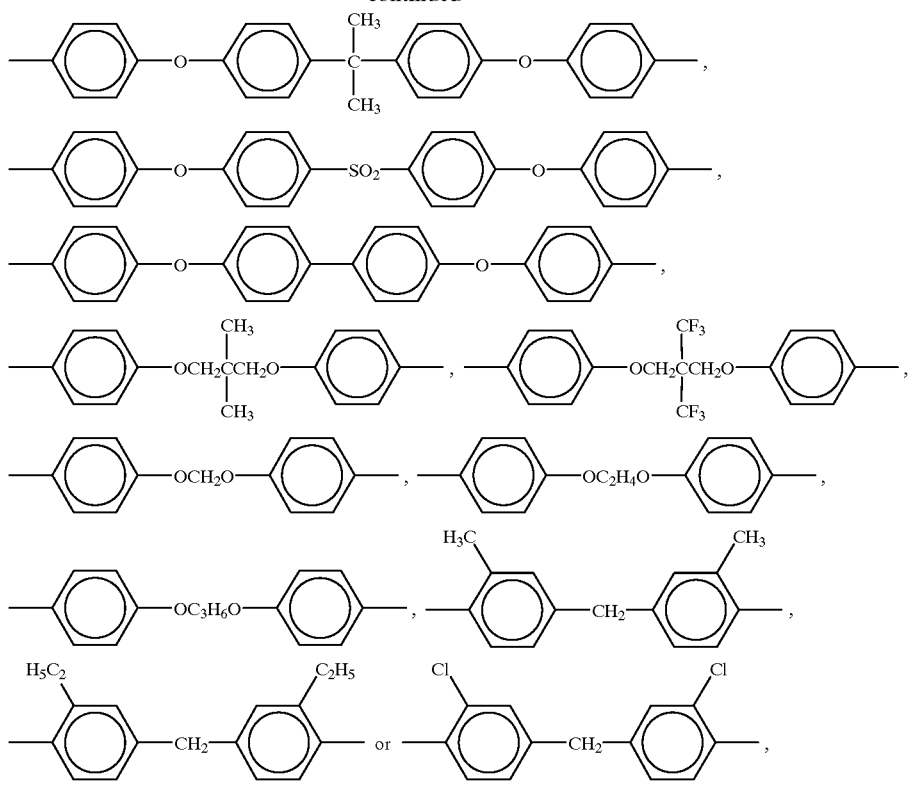

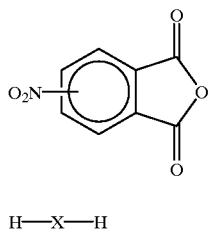

H—X—H (III)

wherein X is —NHYHN— group in which Y is the same as that previously defined.

Further, there is provided a method of producing an aromatic carboxylic acid compound of formula (V):

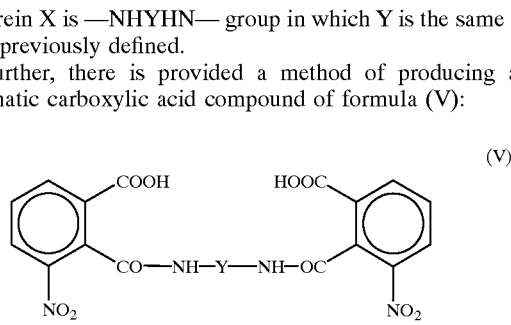

wherein Y is the same as that previously defined, comprising the step of allowing 3-nitrophthalic anhydride to react with a diamine compound of formula (IV) using a reaction solvent selected from the group consisting of acetic acid, tetrahydrofuran and nitrobenzene:

H₂N—Y—NH₂   (IV)

wherein Y is the same as that previously defined.

By the above-mentioned synthesis method, the aromatic carboxylic acid compound of formula (V), that is, a 3-nitrophthalamide dimer, can be efficiently produced as a pure product.

In addition, there is also provided a method of producing an aromatic carboxylic acid compound of formula (VI), which method comprises the steps of dissolving 3-nitrophthalic anhydride in acetic anhydride to prepare an acetic anhydride solution of 3-nitrophthalic anhydride, and adding a diamine compound (H₂N—Y—NH₂) in small portions to the acetic anhydride solution so as to dissolve the diamine compound therein:

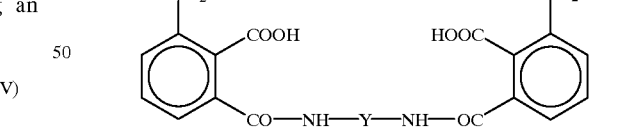

wherein Y is the same as that previously defined.

In this case, although the aromatic carboxylic acid compound of formula (VI) can be efficiently produced in relatively high yields, a trace amount of the compound represented by formula (V) is simultaneously generated as the by-product.

To obtain the compound of formula (VI) in a pure product, the following separating and purification step is effective. Namely, the compound of formula (VI) can be preferentially extracted from a mixture of the reaction products, namely, the aromatic carboxylic acid compounds of formulas (V) and (VI) with a mixed solvent of water and an alcohol. In the present invention, ethyl alcohol is preferably used for the preparation of the mixed solvent. In such a case, it is preferable that the ratio by volume of water to ethyl alcohol for use in the mixed solvent be in the range of 60:40 to 70:30.

Thus, the aromatic carboxylic acid compounds of formulas (V) and (VI) can be selectively and efficiently synthesized from the reaction between 3-nitrophthalic anhydride and a diamine compound.

As the leuco dye for use in the present invention, which may be employed alone or in combination, any conventional dyes for use in the conventional leuco-dye-containing recording materials can be employed. For example, triphenylmethanephthalide leuco compounds, triallylmethane leuco compounds, fluoran leuco compounds, phenothiazine leuco compounds, thiofluoran leuco compounds, xanthene leuco compounds, indophthalyl leuco compounds, spiropyran leuco compounds, azaphthalide leuco compounds, couromeno-pyrazole leuco compounds, methine leuco compounds, rhodamineanilino-lactam leuco compounds, rhodaminelactam leuco compounds, quinazoline leuco compounds, diazaxanthene leuco compounds and bislactone leuco compounds are preferably employed.

Specific examples of those leuco dyes are as follows:

3,3-bis(p-dimethylanilino)phthalide,
3,3-bis(p-dimethylanilino)-6-dimethylaminophthalide (or Crystal Violet Lactone),
3,3-bis(p-dimethylanilino)-6-diethylaminophthalide,
3,3-bis(p-dimethylanilino)-6-chlorophthalide,
3,3-bis(p-dibutylanilino)phthalide,
3-cyclohexylamino-6-chlorofluoran,
3-dimethylamino-5,7-dimethylfluoran,
3-diethylamino-7-chlorofluoran,
3-diethylamino-7-methylfluoran,
3-diethylamino-7,8-benzfluoran,
3-diethylamino-6-methyl-7-chlorofluoran,
3-(N-p-tolyl-N-ethylamino)-6-methyl-7-anilinofluoran,
3-pyrrolidino-6-methyl-7-anilinofluoran,
2-(m-trifluoromethylanilino)-6-diethylaminofluoran,
2-[3,6-bis(diethylamino)-9-(o-chloroanilino)xanthylbenzoic acid lactam],
3-diethylamino-6-methyl-7-(m-trichloromethylanilino)fluoran,
3-diethylamino-7-(o-chloroanilino)fluoran,
3-dibutylamino-7-(o-chloroanilino)fluoran,
3-diamylamino-6-methyl-7-anilinofluoran,
3-(N-methyl-N-amylamino)-6-methyl-7-anilinofluoran,
3-(N-methyl-N-isopropylamino)-6-methyl-7-anilinofluoran,
3-(N-methyl-N-cyclohexylamino)-6-methyl-7-anilinofluoran,
3-(N-ethyl-N-isopropylamino)-6-methyl-7-anilinofluoran,
3-(N-methyl-N-isoamylamino)-6-methyl-7-anilinofluoran,
3-(N-methyl-N-isobutylamino)-6-methyl-7-anilinofluoran,
3-diethylamino-6-chloro-7-anilinofluoran,
3-(N-ethyl-N-2-ethoxypropylamino)-6-methyl-7-anilinofluoran,
3-(N-ethyl-N-tetrafurfurylamino)-6-methyl-7-anilinofluoran,
3-(N-ethyl-N-tetrahydrofurfurylamino)-6-methyl-7-anilinofluoran,
3-diethylamino-6-methyl-7-anilinofluoran,
3-dibutylamino-6-methyl-7-anilinofluoran,
3-diethylamino-5-methyl-7-(N,N-dibenzylamino)fluoran,
benzoyl leuco methylene blue,
6'-chloro-8'-methoxy-benzoindolino-spiropyran,
6'-bromo-8'-methoxy-benzoindolino-spiropyran,
3-(2'-hydroxy-4'-dimethylanilino)-3-(2'-methoxy-5'-chlorophenyl)phthalide,
3-(2'-hydroxy-4'-dimethylanilino)-3-(2'-methoxy-5'-nitrophenyl)phthalide,
3-(2'-hydroxy-4'-diethylanilino)-3-(2'-methoxy-5'-tolyl)phthalide,
3-diethylamino-6-methyl-7-(2',4'-dimethylanilino)fluoran,
3-(2'-methoxy-4'-dimethylanilino)-3-(2'-hydroxy-4'-chloro-5'-tolyl)phthalide,
3-morphorino-7-(N-propyl-trifluoromethylanilino)fluoran,
3-pyrrolidino-7-trifluoromethylanilinofluoran,
3-diethylamino-5-chloro-7-(N-benzyl-trifluoromethylanilino)fluoran,
3-pyrrolidino-7-(di-p-chlorophenyl)methylaminofluoran,
3-diethylamino-5-chloro-7-(α-phenylethylamino)fluoran,
3-(N-ethyl-p-toluidino)-7-(α-phenylethylamino)fluoran,
3-diethylamino-7-(o-methoxycarbonylphenylamino)fluoran,
3-diethylamino-5-methyl-7-(α-phenylethylamino)fluoran,
3-diethylamino-7-piperidinofluoran,
2-chloro-3-(N-methyltoluidino)-7-(p-N-butylanilino)fluoran,
3-(N-ethyl-N-cyclohexylamino)-5,6-benzo-7-α-naphthylamino-4'-bromofluoran,
3-(N-benzyl-N-cyclohexylamino)-5,6-benzo-7-α-naphthylamino-4'-bromofluoran,
3-diethylamino-6-methyl-7-mesidino-4',5'-benzofluoran,
3-(p-dimethylanilino)-3-[1,1-bis(p-dimethylanilino)ethylene-2-yl]phthalide,
3-(p-dimethylanilino)-3-[1,1-bis(p-dimethylanilino)ethylene-2-yl]-6-dimethylaminophthalide,
3-(p-dimethylanilino)-3-(1-p-dimethylanilino-1-phenylethylene-2-yl)phthalide,
3-(p-dimethylanilino)-3-(1-p-dimethylanilino-1-p-chlorophenylethylene-2-yl)-6-dimethylaminophthalide,
3-(4'-dimethylamino-2'-methoxy)-3-(1"-p-dimethylanilino-1"-p-chlorophenyl-1",3"-butadiene-4"-yl)benzophthalide,
3-(4'-dimethylamino-2'-benzyloxy)-3-(1"-p-dimethylanilino-1"-phenyl-1",3"-butadiene-4"-yl)benzophthalide,
3,6-bis(dimethylamino)fluorenespiro(9,3')-6"-dimethylaminophthalide,
3-dimethylamino-6-dimethylamino-fluorene-9-spiro-3'-(6'-dimethylamino)phthalide,
3,3-bis[2-(p-dimethylanilino)-2-(p-methoxyphenyl)ethenyl]-4,5,6,7-tetrachlorophthalide,
3-bis[1,1-bis(4-pyrrolidinophenyl)ethylene-2-yl]-5,6-dichloro-4,7-dibromophthalide,
bis(p-dimethylaminostyryl)-1-naphthalenesulfonylmethane, and bis(p-dimethylaminostyryl)-1-p-tolylsulfonylmethane.

The thermosensitive coloring layer comprises the above-mentioned leuco dye serving as the coloring agent, and the previously mentioned compound (A), preferably the aromatic carboxylic acid compound of formula (I), serving as the color developer. When necessary, various electron-acceptor compounds, for example, phenol compounds, thiophenol compounds, thiourea derivatives, organic acids and metallic salts thereof may be used in combination with the aforementioned compound (A).

Specific examples of the color developer for use in the present invention are as follows:

4,4'-isopropylidenebisphenol,
4,4'-isopropylidenebis(o-cresol),
4,4'-sec-butylidenebisphenol,
4,4'-isopropylidenebis(o-tert-butylphenol),
4,4'-cyclohexylidenebisphenol,
4,4'-isopropylidenebis(2-chlorophenol),
2,2'-methylenebis(4-methyl-6-tert-butylphenol),
2,2'-methylenebis(4-ethyl-6-tert-butylphenol),
4,4'-sec-butylidenebis(6-tert-butyl-2-cresol),
1,1,3-tris(2-methyl-4-hydroxy-5-cyclohexylphenyl)butane,
4,4'-thiobis(6-tert-butyl-2-cresol),
2,4'-diphenolsulfone,
2,2'-diallyl-4,4'-dihydroxydiphenylsulfone,
3,4'-dihydroxy-4'-methyldiphenylsulfone,
4-isopropoxy-4'-hydroxydiphenylsulfone,
4-benzyloxy-4'-hydroxydiphenylsulfone,
4,4'-diphenolsulfoxide,
isopropyl p-hydroxybenzoate,
benzyl p-hydroxybenzoate,
benzyl protocatechuate,
stearyl gallate,
lauryl gallate,
octyl gallate,
1,7-bis(4-hydroxyphenylthio)-3,5-dioxaheptane,
1,5-bis(4-hydroxyphenylthio)-3-oxapentane,
1,3-bis(4-hydroxyphenylthio)-propane,
monocalcium salt of monobenzyl phthalate,
N,N'-diphenylthiourea,
N,N'-di(m-chlorophenyl)thiourea,
salicylanilide,
antipyrine complex of zinc thiocyanate,
zinc salt of 1-acetyloxy-2-naphthoic acid,
zinc salt of 2-acetyloxy-3-naphthoic acid,
zinc salt of 2-acetyloxy-1-naphthoic acid,
bis(4-hydroxyphenyl)methyl acetate,
bis(4-hydroxyphenyl)benzyl acetate,
4-[β-(p-methoxyphenoxy)ethoxy]salicylic acid,
1,3-bis(4-hydroxyphenyl)benzene,
1,4-bis(4-hydroxyphenyl)benzene,
4,4'-diphenolsulfone,
3,3'-diallyl-4,4'-diphenolsulfone,
α,α-bis(4-hydroxyphenyl)-α-methyltoluene,
tetrabromobisphenol A,
tetrabromobisphenol S,
4,4'-thiobis(2-methylphenol),
4,4'-thiobis(2-chlorophenol),
zinc p-nitrobenzoate,
1,3,5-tris(4-tert-butyl-3-hydroxy-2,6-dimethylbenzyl)isocyanuric acid,
2,2-bis(3,4'-dihydroxyphenyl)propane, and
bis(4-hydroxy-3-methylphenyl)sulfide.

To obtain a thermosensitive recording material according to the present invention, the thermosensitive coloring layer comprising the above-mentioned leuco dyes and color developers, and auxiliary components to be described later may be provided on the support.

The thermosensitive coloring layer may further comprise a binder agent. As the binder agent for use in the present invention, any conventional binder agents used in the conventional thermosensitive recording materials can appropriately be employed.

Examples of the binder agent for use in the thermosensitive coloring layer include water-soluble polymers such as polyvinyl alcohol, starch and starch derivatives, cellulose derivatives such as methoxy cellulose, hydroxyethyl cellulose, carboxymethyl cellulose, methyl cellulose and ethyl cellulose, sodium polyacrylate, polyvinyl pyrrolidone, acrylamide-acrylic ester copolymer, acrylamide-acrylic ester-methacrylic acid terpolymer, alkali salts of styrene-maleic anhydride copolymer, alkali salts of isobutylene-maleic anhydride copolymer, polyacrylamide, sodium alginate, gelatin, and casein; emulsions such as polyvinyl acetate, polyurethane, polyacrylate, polymethacrylate, vinyl chloride-vinyl acetate copolymer, ethylene-vinyl acetate copolymer, vinyl acetate-acryl copolymer and styrene-acrylic ester copolymer; and latexes such as styrene-butadiene copolymer and styrene-butadiene-acryl copolymer.

According to the present invention, the thermosensitive coloring layer may further comprise a thermofusible material as the thermosensitivity-improving agent.

Specific examples of the thermofusible material are as follows: fatty acids such as stearic acid and behenic acid; fatty amides such as stearamide and palmitamide; fatty acid metallic salts such as zinc stearate, aluminum stearate, calcium stearate, zinc palmitate, and zinc behenate; and diphenyl sulfone, diphenyl methane, p-benzylbiphenyl, terphenyl, triphenylmethane, benzyl p-benzyloxybenzoate, β-benzyloxy naphthalene, phenyl β-naphthoate, phenyl 1-hydroxy-2-naphthoate, methyl 1-hydroxy-2-naphthoate, diphenyl carbonate, guaiacol carbonate, dibenzyl terephthalate, dimethyl terephthalate, 1,4-dimethoxynaphthalene, 1,4-diethoxynaphthalene, 1,4-dibenzyloxynaphthalene, 1,2-bis(phenoxy)ethane, 1,2-bis(3-methylphenoxy)ethane, 1,2-bis(4-methylphenoxy)ethane, 1,4-bis(phenoxy)butane, 1,4-bis(phenoxy)-2-butene, 1,2-bis(4-(methoxyphenylthio)ethane, dibenzoylmnethane, 1,4-bis(phenylthio)butane, 1,4-bis(phenylthio)-2-butene, 1,2-bis(4-methoxyphenylthio)ethane, 1,3-bis(2-vinyloxyethoxy)benzene, 1,4-bis(2-vinyloxyethoxy)benzene, p-(2-vinyloxyethoxy)biphenyl, p-aryloxybiphenyl, p-propargyloxybiphenyl, dibenzoyloxymethane, 1,3-dibenzoyloxypropane, dibenzyl disulfide, 1,1-diphenylethanol, 1,1-diphenylpropanol, p-(benzyloxy) benzyl alcohol, 1,3-diphenoxy-2-propanol, N-octadecylcarbamoyl-p-methoxycarbonylbenzene, N-octadecylcarbamoylbenzene, dibenzyl oxalate, bis(4-methylbenzyl)oxalate, bis(4-chlorobenzyl)oxalate, 1,5-bis(p-methoxyphenyloxy)-3-oxapentane, and 1,2-bis(4-methoxyphenoxy)propane.

When necessary, the thermosensitive coloring layer may further comprise auxiliary additive components such as a filler, a surface active agent, a lubricant and an agent for preventing color formation by pressure application, which are used in the conventional thermosensitive recording materials.

Examples of the filler for use in the present invention are finely-divided particles of inorganic fillers such as calcium carbonate, silica, zinc oxide, titanium oxide, aluminum hydroxide, zinc hydroxide, barium sulfate, clay, kaolin, talc, surface-treated calcium and surface-treated silica; and finely-divided particles of organic fillers such as urea-formaldehyde resin, styrene-methacrylic acid copolymer, polystyrene resin and vinylidene chloride resin.

Examples of the lubricant for use in the present invention include higher fatty acids and amides, esters and metallic salts thereof; and a variety of waxes such as an animal wax, a vegetable wax, a mineral wax, and a petroleum wax.

When the thermosensitive coloring layer coating liquid comprising the compound (A) is coated and dried to provide the thermosensitive coloring layer, it is proper that the content of compound (A) serving as the color developer, for example, the aromatic carboxylic acid compound of formula (I), be in the range of 1 to 5 g/m$^2$, preferably 1 to 2 g/m$^2$ on a dry basis.

It is preferable that the thermosensitive recording material of the present invention further comprise an intermediate layer comprising as the main component plastic void particles in the form of sphere, which is provided between the support and the thermosensitive coloring layer. This intermediate layer serves as a heat-insulating layer. Owing to the intermediate layer, therefore, thermal energy supplied by a thermal head can efficiently be utilized, thereby improving the thermosensitivity of the recording material.

In particular, when the average particle diameter of the plastic void particles for use in the intermediate layer is in the range of 0.2 to 20 μm and the voidage thereof is 40% or more, the flexibility of the intermediate layer is increased. As a result, the adhesion between the thermosensitive recording material and the thermal head is improved, and therefore, dot reproduction performance becomes excellent.

The void particles for use in the intermediate layer comprise a thermoplastic resin for forming a shell of each void particle. Air or other gasses are contained in the void particles in the expanded state.

It is preferable that the average particle diameter of the void particles be in the range of about 0.2 to 20 μm, as mentioned above. When the particle size of the void particles is within the above range, there is no problem in the production of the intermediate layer because the voidage of the void particles can freely be determined. In addition, the surface smoothness of the intermediate layer is not decreased after coating and drying the liquid comprising the void particles, so that the adhesion of the thermosensitive coloring layer to the thermal head does not lower, and consequently, deterioration of the thermosensitivity of the recording material can be avoided. Further, it is preferable that the void particles classified in a narrow distribution be employed in the intermediate layer.

It is preferable that the voidage of the void particles for use in the intermediate layer be 40% or more, and more preferably 90% or more, from the viewpoint of the heat insulating effect. In the present invention, the voidage of the void particles for use in the intermediate layer is expressed by the following formula:

$$\text{Voidage (\%)} = \frac{\text{(Inner diameter of void particle)}}{\text{(Outer diameter of void particle)}} \times 100$$

When the voidage is within the above range, sufficient heat insulating effect of the intermediate layer can be obtained, so that the thermal energy supplied by the thermal head can be inhibited from escaping through the support of the thermosensitive recording material. As a result, the thermosensitivity-improving effect can be increased.

Specific examples of the thermoplastic resin for forming a shell of the void particle are polystyrene, polyvinyl chloride, polyvinylidene chloride, polyvinyl acetate, polyacrylate, polyacrylonitrile, polybutadiene, and copolymer resin thereof. Of those thermoplastic resins, a copolymer resin comprising as the main component vinylidene chloride or acrylonitrile is preferably employed in the present invention.

A binder resin for the formation of the above-mentioned intermediate layer may be appropriately selected from the conventional water-soluble polymers and aqueous polymeric emulsions.

Specific examples of the binder agent for use in the intermediate layer include water-soluble polymers such as polyvinyl alcohol, starch and starch derivatives, cellulose derivatives such as methoxy cellulose, hydroxyethyl cellulose, carboxymethyl cellulose, methyl cellulose and ethyl cellulose, sodium polyacrylate, polyvinyl pyrrolidone, acrylamide-acrylic ester copolymer, acrylamide-acrylic ester-methacrylic acid terpolymer, alkali salts of styrene-maleic anhydride copolymer, alkali salts of isobutylene-maleic anhydride copolymer, polyacrylamide, sodium alginate, gelatin, and casein; and aqueous polymeric emulsions, for example, latexes such as styrene-butadiene copolymer and styrene-butadiene-acryl copolymer and emulsions such as vinyl acetate resin, vinyl acetate-acrylic acid copolymer, styrene-acrylic ester copolymer, acrylate resin, and polyurethane resin.

In the intermediate layer for use in the present invention, the previously mentioned minute void particles and binder resin may be used in combination with auxiliary additive components such as a filler, a thermofusible material and a surface active agent, which are used in the conventional thermosensitive recording materials. Specific examples of the filler and the thermofusible material are the same as those mentioned in the description of the thermosensitive coloring layer.

Furthermore, in the present invention, an additional layer comprising a pigment, a binder agent and a thermofusible material may be interposed between the intermediate layer and the thermosensitive coloring layer when necessary.

In addition, the thermosensitive recording material may further comprise a protective layer which is formed on the thermosensitive coloring layer in order to improve the head-matching properties of the thermosensitive recording material with the thermal head, improve the preservation stability of the recorded images and improve the writing and printing quality of the recording material. In this case, the protective layer comprises the previously mentioned filler, binder resin and thermofusible material.

The thermosensitive recording material of the present invention is usable in any fields that employ the conventional thermosensitive recording materials. For instance, the thermosensitive recording material can be used as a paper for facsimile apparatus, a point-of-sales (POS) label for food, a bar code label for industrial applications, a thermosensitive recording adhesive label of liner-less type, a ticket paper, a magnetic ticket paper, a paper for CAD, and a transparent thermosensitive film.

Other features of this invention will become apparent in the course of the following description of exemplary embodiments, which are given for illustration of the invention and are not intended to be limiting thereof.

EXAMPLE 1

A mixture of the following components was separately dispersed and pulverized in a porcelain ball mill, so that a Liquid A, a Liquid B, a Liquid C and a Liquid D were prepared:

|  | Parts by Weight |
|---|---|
| [Liquid A] | |
| 3-N,N-dibutylamino-6-methyl-7-anilinofluoran | 10 |
| 10% aqueous solution of polyvinyl alcohol | 10 |
| Water | 30 |
| [Liquid B] | |
| Compound No. 4 (shown in TABLE 1) | 10 |
| 10% aqueous solution of polyvinyl alcohol | 10 |
| Water | 30 |
| [Liquid C] | |
| Silica gel (Trademark "P527" made by Mizusawa Industrial Chemicals, Ltd.) | 10 |
| 10% aqueous solution of polyvinyl alcohol | 10 |
| Water | 30 |
| [Liquid D] | |
| Zinc stearate | 10 |
| 10% aqueous solution of polyvinyl alcohol | 10 |
| Water | 30 |

A mixture of the following components was stirred and dispersed in a dispersion mixer, so that a Liquid E was prepared:

| [Liquid E] | Parts by Weight |
|---|---|
| Unexpanded minute void plastic particles (solid content: 24 wt. %, average particle diameter: 3 µm, and voidage: 95%) | 40 |
| Styrene - butadiene copolymer latex | 10 |
| Water | 50 |

[Formation of intermediate layer]

The Liquid E and the Liquid C were mixed at a ratio by weight of 2:1, so that a coating liquid for an intermediate layer was prepared. The thus prepared intermediate layer coating liquid was coated on a sheet of commercially available high quality paper with a basis weight of 60 g/m$^2$, serving as a support, and then dried so as to have a deposition amount of 3 g/m$^2$ on a dry basis, whereby an intermediate layer was formed on the support.

[Formation of thermosensitive coloring layer]

The Liquid A, the Liquid B, the Liquid C, and the Liquid D were mixed at a ratio by weight of 1:2:1:1 to prepare a thermosensitive coloring layer coating liquid. The thus prepared thermosensitive coloring layer coating liquid was coated on the above prepared intermediate layer and then dried so as to have a deposition amount of 2.5 g/m$^2$ on a dry basis, whereby a thermosensitive coloring layer was formed on the intermediate layer.

The surface of the thermosensitive coloring layer thus obtained was subjected to calendering with the application of a pressure of 10 kg/cm$^2$.

Thus, a thermosensitive recording material No. 1 according to the present invention was obtained.

EXAMPLE 2

The procedure for preparation of the thermosensitive recording material No. 1 in Example 1 was repeated except that the Compound No. 4 in the Liquid B for the thermosensitive coloring layer coating liquid in Example 1 was replaced by Compound No. 5 shown in TABLE 1.

Thus, a thermosensitive recording material No. 2 according to the present invention was obtained.

EXAMPLE 3

The procedure for preparation of the thermosensitive recording material No. 1 in Example 1 was repeated except that the Compound No. 4 in the Liquid B for the thermosensitive coloring layer coating liquid in Example 1 was replaced by Compound No. 6 shown in TABLE 1.

Thus, a thermosensitive recording material No. 3 according to the present invention was obtained.

EXAMPLE 4

The procedure for preparation of the thermosensitive recording material No. 1 in Example 1 was repeated except that the Compound No. 4 in the Liquid B for the thermosensitive coloring layer coating liquid in Example 1 was replaced by Compound No. 15 shown in TABLE 1.

Thus, a thermosensitive recording material No. 4 according to the present invention was obtained.

EXAMPLE 5

The procedure for preparation of the thermosensitive recording material No. 1 in Example 1 was repeated except that the Compound No. 4 in the Liquid B for the thermosensitive coloring layer coating liquid in Example 1 was replaced by Compound No. 27 shown in TABLE 1.

Thus, a thermosensitive recording material No. 5 according to the present invention was obtained.

EXAMPLE 6

The procedure for preparation of the thermosensitive recording material No. 1 in Example 1 was repeated except that the Compound No. 4 in the Liquid B for the thermosensitive coloring layer coating liquid in Example 1 was replaced by Compound No. 55 shown in TABLE 1.

Thus, a thermosensitive recording material No. 6 according to the present invention was obtained.

EXAMPLE 7

The procedure for preparation of the thermosensitive recording material No. 1 in Example 1 was repeated except that the Compound No. 4 in the Liquid B for the thermosensitive coloring layer coating liquid in Example 1 was replaced by Compound No. 11 shown in TABLE 1.

Thus, a thermosensitive recording material No. 7 according to the present invention was obtained.

EXAMPLE 8

The procedure for preparation of the thermosensitive recording material No. 1 in Example 1 was repeated except that the Compound No. 4 in the Liquid B for the thermosensitive coloring layer coating liquid in Example 1 was replaced by Compound No. 12 shown in TABLE 1.

Thus, a thermosensitive recording material No. 8 according to the present invention was obtained.

EXAMPLE 9

The procedure for preparation of the thermosensitive recording material No. 1 in Example 1 was repeated except that the Compound No. 4 in the Liquid B for the thermosensitive coloring layer coating liquid in Example 1 was replaced by Compound No. 13 shown in TABLE 1.

Thus, a thermosensitive recording material No. 9 according to the present invention was obtained.

EXAMPLE 10

The procedure for preparation of the thermosensitive recording material No. 1 in Example 1 was repeated except that the Compound No. 4 in the Liquid B for the thermosensitive coloring layer coating liquid in Example 1 was replaced by Compound No. 14 shown in TABLE 1.

Thus, a thermosensitive recording material No. 10 according to the present invention was obtained.

EXAMPLE 11

The procedure for preparation of the thermosensitive recording material No. 1 in Example 1 was repeated except that the Compound No. 4 in the Liquid B for the thermosensitive coloring layer coating liquid in Example 1 was replaced by Compound No. 22 shown in TABLE 1.

Thus, a thermosensitive recording material No. 11 according to the present invention was obtained.

EXAMPLE 12

The procedure for preparation of the thermosensitive recording material No. 1 in Example 1 was repeated except that the Compound No. 4 in the Liquid B for the thermosensitive coloring layer coating liquid in Example 1 was replaced by Compound No. 23 shown in TABLE 1.

Thus, a thermosensitive recording material No. 12 according to the present invention was obtained.

EXAMPLE 13

The procedure for preparation of the thermosensitive recording material No. 1 in Example 1 was repeated except that the Compound No. 4 in the Liquid B for the thermosensitive coloring layer coating liquid in Example 1 was replaced by Compound No. 24 shown in TABLE 1.

Thus, a thermosensitive recording material No. 13 according to the present invention was obtained.

EXAMPLE 14

The procedure for preparation of the thermosensitive recording material No. 1 in Example 1 was repeated except that the Compound No. 4 in the Liquid B for the thermosensitive coloring layer coating liquid in Example 1 was replaced by Compound No. 26 shown in TABLE 1.

Thus, a thermosensitive recording material No. 14 according to the present invention was obtained.

EXAMPLE 15

The procedure for preparation of the thermosensitive recording material No. 1 in Example 1 was repeated except that the Compound No. 4 in the Liquid B for the thermosensitive coloring layer coating liquid in Example 1 was replaced by Compound No. 50 shown in TABLE 1.

Thus, a thermosensitive recording material No. 15 according to the present invention was obtained.

EXAMPLE 16

The procedure for preparation of the thermosensitive recording material No. 1 in Example 1 was repeated except that the Compound No. 4 in the Liquid B for the thermosensitive coloring layer coating liquid in Example 1 was replaced by Compound No. 51 shown in TABLE 1.

Thus, a thermosensitive recording material No. 16 according to the present invention was obtained.

EXAMPLE 17

The procedure for preparation of the thermosensitive recording material No. 1 in Example 1 was repeated except that the Compound No. 4 in the Liquid B for the thermosensitive coloring layer coating liquid in Example 1 was replaced by Compound No. 54 shown in TABLE 1.

Thus, a thermosensitive recording material No. 17 according to the present invention was obtained.

EXAMPLE 18

The procedure for preparation of the thermosensitive recording material No. 1 in Example 1 was repeated except that the Compound No. 4 in the Liquid B for the thermosensitive coloring layer coating liquid in Example 1 was replaced by Compound No. 56 shown in TABLE 1.

Thus, a thermosensitive recording material No. 18 according to the present invention was obtained.

EXAMPLE 19

The procedure for preparation of the thermosensitive recording material No. 1 in Example 1 was repeated except that the intermediate layer employed in Example 1 was not interposed between the support and the thermosensitive coloring layer.

Thus, a thermosensitive recording material No. 19 according to the present invention was obtained.

EXAMPLE 20

The procedure for preparation of the thermosensitive recording material No. 5 in Example 5 was repeated except that the intermediate layer employed in Example 5 was not interposed between the support and the thermosensitive coloring layer.

Thus, a thermosensitive recording material No. 20 according to the present invention was obtained.

Comparative Example 1

The procedure for preparation of the thermosensitive recording material No. 1 in Example 1 was repeated except that the Compound No. 4 in the Liquid B for the thermosensitive coloring layer coating liquid in Example 1 was replaced by mono-α-methyl 3-nitrophthalate.

Thus, a comparative thermosensitive recording material No. 1 was obtained.

Comparative Example 2

The procedure for preparation of the thermosensitive recording material No. 1 in Example 1 was repeated except that the Compound No. 4 in the Liquid B for the thermosensitive coloring layer coating liquid in Example 1 was replaced by mono-β-methyl 3-nitrophthalate.

Thus, a comparative thermosensitive recording material No. 2 was obtained.

Comparative Example 3

The procedure for preparation of the thermosensitive recording material No. 1 in Example 1 was repeated except that the Compound No. 4 in the Liquid B for the thermosensitive coloring layer coating liquid in Example 1 was replaced by mono-β-benzyl 3-nitrophthalate.

Thus, a comparative thermosensitive recording material No. 3 was obtained.

Comparative Example 4

The procedure for preparation of the thermosensitive recording material No. 1 in Example 1 was repeated except that the Compound No. 4 in the Liquid B for the thermosensitive coloring layer coating liquid in Example 1 was replaced by 2,4-hydroxyphenylsulfone.

Thus, a comparative thermosensitive recording material No. 4 was obtained.

(Measurement of Coloring Density of Image)

Each of the thermosensitive recording materials Nos. 1 to 20 according to the present invention obtained in Examples 1 to 20 and the comparative thermosensitive recording materials Nos. 1 to 4 obtained in Comparative Examples 1 to 4 was loaded in a printing test apparatus equipped with a commercially available thin film head (made by Matsushita Electronic Components Co., Ltd.), and images were formed on each recording material under the conditions that the applied electric power was 0.68 W/dot, the period for one line was 10 ms/line and the scanning line density was 8×3.85 dot/mm, with the pulse width changed to 0.8 msec, 1.0 msec and 1.2 msec.

The coloring density of the recorded image was measured by a McBeth densitometer.

The results are given in TABLE 2.

(Evaluation of Preservation Stability of Recorded Image)

1. Plasticizer Resistance Test

Images were thermally printed on each of the thermosensitive recording materials in such a manner that a heating block of 180° C. was brought into contact with each recording material for one second with the application of a pressure of 2 kg/cm$^2$ thereto, using a heat gradient tester made by TOYO SEIKI SEISAKU-SHO, Ltd.

The initial coloring density of each image area was measured using the McBeth densitometer.

A sheet of commercially available polyvinyl chloride wrap, made by Shin-Etsu Polymer Co., Ltd., was overlaid on the image area of each image-bearing sample. Each sample was allowed to stand at 40° C. with the application of a load of 5 kg thereto for 16 hours.

After 16 hours, the density of the image area was measured using the McBeth densitometer.

The results are shown in TABLE 2.

TABLE 2

| | Coloring Density | | | Preservation Stability of Recorded Image (Coloring Density) | |
|---|---|---|---|---|---|
| | 0.8 ms | 1.0 ms | 1.2 ms | At initial stage | Plasticizer resistance test |
| Ex. 1 | 1.30 | 1.30 | 1.31 | 1.45 | 0.80 |
| Ex. 2 | 1.25 | 1.33 | 1.33 | 1.46 | 0.70 |
| Ex. 3 | 1.28 | 1.29 | 1.32 | 1.45 | 0.72 |
| Ex. 4 | 1.18 | 1.30 | 1.32 | 1.23 | 0.69 |
| Ex. 5 | 0.96 | 1.07 | 1.08 | 1.18 | 1.13 |
| Ex. 6 | 0.85 | 1.03 | 1.00 | 1.15 | 1.02 |
| Ex. 7 | 1.28 | 1.30 | 1.32 | 1.40 | 0.82 |
| Ex. 8 | 1.30 | 1.31 | 1.30 | 1.42 | 0.85 |
| Ex. 9 | 1.31 | 1.31 | 1.31 | 1.45 | 0.81 |
| Ex. 10 | 1.30 | 1.31 | 1.31 | 1.40 | 0.90 |
| Ex. 11 | 1.25 | 1.30 | 1.31 | 1.35 | 1.00 |
| Ex. 12 | 1.28 | 1.31 | 1.33 | 1.40 | 0.99 |
| Ex. 13 | 1.00 | 1.10 | 1.11 | 1.25 | 1.20 |
| Ex. 14 | 1.01 | 1.08 | 1.12 | 1.15 | 1.10 |
| Ex. 15 | 1.20 | 1.25 | 1.28 | 1.35 | 1.10 |
| Ex. 16 | 1.15 | 1.20 | 1.22 | 1.33 | 1.08 |
| Ex. 17 | 0.90 | 1.10 | 1.12 | 1.20 | 1.13 |
| Ex. 18 | 0.80 | 0.99 | 1.08 | 1.18 | 1.15 |
| Ex. 19 | 0.59 | 0.99 | 1.21 | 1.48 | 0.75 |
| Ex. 20 | 0.51 | 0.83 | 0.95 | 1.17 | 1.07 |
| Comp. Ex. 1 | 1.20 | 1.31 | 1.33 | 1.41 | 0.46 |
| Comp. Ex. 2 | 1.29 | 1.35 | 1.36 | 1.44 | 0.50 |
| Comp. Ex. 3 | 1.10 | 1.21 | 1.30 | 1.35 | 0.55 |
| Comp. Ex. 4 | 1.24 | 1.36 | 1.35 | 1.60 | 0.35 |

As can be seen from the results shown in TABLE 2, the plasticizer resistance of images formed in the thermosensitive recording material of the present invention is excellent. In addition, when the intermediate layer comprising minute void particles is interposed between the support and the thermosensitive coloring layer, the coloring sensitivity is improved and the plasticizer resistance is excellent.

EXAMPLE 21

The procedure for preparation of the thermosensitive recording material No. 1 in Example 1 was repeated except that the Compound No. 4 in the Liquid B for the thermosensitive coloring layer coating liquid in Example 1 was replaced by Compound No. 123 shown in TABLE 1.

Thus, a thermosensitive recording material No. 21 according to the present invention was obtained.

EXAMPLE 22

The procedure for preparation of the thermosensitive recording material No. 1 in Example 1 was repeated except that the Compound No. 4 in the Liquid B for the thermosensitive coloring layer coating liquid in Example 1 was replaced by Compound No. 131 shown in TABLE 1.

Thus, a thermosensitive recording material No. 22 according to the present invention was obtained.

EXAMPLE 23

The procedure for preparation of the thermosensitive recording material No. 21 in Example 21 was repeated except that the intermediate layer employed in Example 21 was not interposed between the support and the thermosensitive coloring layer.

Thus, a thermosensitive recording material No. 23 according to the present invention was obtained.

EXAMPLE 24

The procedure for preparation of the thermosensitive recording material No. 22 in Example 22 was repeated except that the intermediate layer employed in Example 22 was not interposed between the support and the thermosensitive coloring layer.

Thus, a thermosensitive recording material No. 24 according to the present invention was obtained.

Comparative Example 5

The procedure for preparation of the thermosensitive recording material No. 1 in Example 1 was repeated except that the Compound No. 4 in the Liquid B for the thermosensitive coloring layer coating liquid in Example 1 was replaced by 2,4'-dihydroxydiphenylsulfone.

Thus, a comparative thermosensitive recording material No. 5 was obtained.

Comparative Example 6

The procedure for preparation of the thermosensitive recording material No. 1 in Example 1 was repeated except that the Compound No. 4 in the Liquid B for the thermosensitive coloring layer coating liquid in Example 1 was replaced by the following compound:

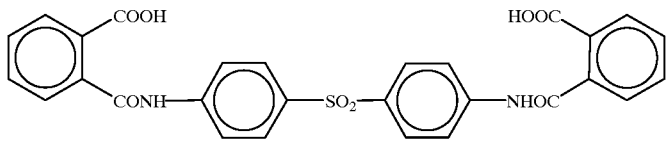

Thus, a comparative thermosensitive recording material No. 6 was obtained.

Comparative Example 7

The procedure for preparation of the comparative thermosensitive recording material No. 6 in Comparative Example 6 was repeated except that the intermediate layer employed in Comparative Example 6 was not interposed between the support and the thermosensitive coloring layer.

Thus, a comparative thermosensitive recording material No. 7 was obtained.

(Measurement of Coloring Density of Image)

Each of the thermosensitive recording materials Nos. 21 to 24 according to the present invention obtained in Examples 21 to 24 and the comparative thermosensitive recording materials Nos. 5 to 7 obtained in Comparative Examples 5 to 7 was loaded in a printing test apparatus equipped with a commercially available thin film head (made by Matsushita Electronic Components Co., Ltd.), and images were formed on each recording material under the conditions that the applied electric power was 0.68 W/dot, the period for one line was 10 ms/line and the scanning line density was 8×3.85 dot/mm, with the pulse width changed to 0.8 msec, 1.0 msec and 1.2 msec.

The coloring density of the recorded image was measured by a McBeth densitometer.

The results are given in TABLE 3.

(Evaluation of Preservation Stability of Recorded Image)

1. Oil Resistance Test

Images were thermally printed on each of the thermosensitive recording materials in such a manner that a heating block of which temperature was set to a temperature where the image recorded in the recording material showed a saturation coloring density was brought into contact with each recording material for one second with the application of a pressure of 2 kg/cm$^2$ thereto, using a heat gradient tester made by TOYO SEIKI SEISAKU-SHO, Ltd.

The initial coloring density of each image area was measured using the McBeth densitometer.

A cotton seed oil was applied to the image area of each image-bearing sample. Each sample was allowed to stand at 40° C. for 16 hours.

After 16 hours, the density of the image area was measured to evaluate the oil resistance.

The results are also shown in TABLE 3.

2. Heat Resistance Test

Images were thermally printed on each of the thermosensitive recording materials in such a manner that a heating block of which temperature was set to a temperature where the image recorded in the recording material showed a saturation coloring density was brought into contact with each recording material for one second with the application of a pressure of 2 kg/cm$^2$ thereto, using a heat gradient tester made by TOYO SEIKI SEISAKU-SHO, Ltd.

Each image-bearing sample was allowed to stand at 100° C. for 15 hours. After 15 hours, the density of the image area was measured to evaluate the heat resistance.

The results are also shown in TABLE 3.

TABLE 3

|  | Coloring Density | | | Preservation Stability of Recorded Image (Coloring Density) | | |
|---|---|---|---|---|---|---|
|  | 0.8 ms | 1.0 ms | 1.2 ms | At initial stage | Oil resistance test | Heat resistance test |
| Ex. 21 | 1.11 | 1.10 | 1.01 | 1.25 | 1.16 | 0.92 |
| Ex. 22 | 1.10 | 1.13 | 1.09 | 1.24 | 1.21 | 0.92 |
| Ex. 23 | 0.62 | 0.77 | 0.83 | 1.01 | 0.82 | 0.82 |
| Ex. 24 | 0.67 | 0.82 | 0.93 | 1.06 | 0.92 | 0.80 |
| Comp. Ex. 5 | 1.36 | 1.39 | 1.38 | 1.55 | 0.80 | 0.88 |
| Comp. Ex. 6 | 0.91 | 1.10 | 1.08 | 1.22 | 1.04 | 0.65 |
| Comp. Ex. 7 | 0.65 | 0.75 | 0.82 | 1.07 | 0.89 | 0.40 |

As can be seen from the results shown in TABLE 3, the oil resistance and the heat resistance of images formed in the thermosensitive recording material of the present invention are excellent.

EXAMPLE 25

The procedure for preparation of the thermosensitive recording material No. 1 in Example 1 was repeated except that the Compound No. 4 in the Liquid B for the thermosensitive coloring layer coating liquid in Example 1 was replaced by Compound No. 175 shown in TABLE 1.

Thus, a thermosensitive recording material No. 25 according to the present invention was obtained.

EXAMPLE 26

The procedure for preparation of the thermosensitive recording material No. 1 in Example 1 was repeated except that the Compound No. 4 in the Liquid B for the thermosensitive coloring layer coating liquid in Example 1 was replaced by Compound No. 187 shown in TABLE 1.

Thus, a thermosensitive recording material No. 26 according to the present invention was obtained.

EXAMPLE 27

The procedure for preparation of the thermosensitive recording material No. 1 in Example 1 was repeated except that the Compound No. 4 in the Liquid B for the thermosensitive coloring layer coating liquid in Example 1 was replaced by Compound No. 193 shown in TABLE 1.

Thus, a thermosensitive recording material No. 27 according to the present invention was obtained.

EXAMPLE 28

The procedure for preparation of the thermosensitive recording material No. 1 in Example 1 was repeated except that the Compound No. 4 in the Liquid B for the thermosensitive coloring layer coating liquid in Example 1 was replaced by Compound No. 180 shown in TABLE 1.

Thus, a thermosensitive recording material No. 28 according to the present invention was obtained.

EXAMPLE 29

The procedure for preparation of the thermosensitive recording material No. 25 in Example 25 was repeated except that the intermediate layer employed in Example 25 was not interposed between the support and the thermosensitive coloring layer.

Thus, a thermosensitive recording material No. 29 according to the present invention was obtained.

EXAMPLE 30

The procedure for preparation of the thermosensitive recording material No. 1 in Example 1 was repeated except that the Compound No. 4 in the Liquid B for the thermosensitive coloring layer coating liquid in Example 1 was replaced by Compound No. 199 shown in TABLE 1.

Thus, a thermosensitive recording material No. 30 according to the present invention was obtained.

EXAMPLE 31

The procedure for preparation of the thermosensitive recording material No. 1 in Example 1 was repeated except that the Compound No. 4 in the Liquid B for the thermosensitive coloring layer coating liquid in Example 1 was replaced by Compound No. 205 shown in TABLE 1.

Thus, a thermosensitive recording material No. 31 according to the present invention was obtained.

EXAMPLE 32

The procedure for preparation of the thermosensitive recording material No. 1 in Example 1 was repeated except that the Compound No. 4 in the Liquid B for the thermosensitive coloring layer coating liquid in Example 1 was replaced by Compound No. 211 shown in TABLE 1.

Thus, a thermosensitive recording material No. 32 according to the present invention was obtained.

EXAMPLE 33

The procedure for preparation of the thermosensitive recording material No. 1 in Example 1 was repeated except that the Compound No. 4 in the Liquid B for the thermosensitive coloring layer coating liquid in Example 1 was replaced by Compound No. 529 shown in TABLE 1.

Thus, a thermosensitive recording material No. 33 according to the present invention was obtained.

EXAMPLE 34

The procedure for preparation of the thermosensitive recording material No. 1 in Example 1 was repeated except that the Compound No. 4 in the Liquid B for the thermosensitive coloring layer coating liquid in Example 1 was replaced by Compound No. 523 shown in TABLE 1.

Thus, a thermosensitive recording material No. 34 according to the present invention was obtained.

EXAMPLE 35

The procedure for preparation of the thermosensitive recording material No. 1 in Example 1 was repeated except that the Compound No. 4 in the Liquid B for the thermosensitive coloring layer coating liquid in Example 1 was replaced by Compound No. 522 shown in TABLE 1.

Thus, a thermosensitive recording material No. 35 according to the present invention was obtained.

EXAMPLE 36

The procedure for preparation of the thermosensitive recording material No. 33 in Example 33 was repeated except that the intermediate layer employed in Example 33 was not interposed between the support and the thermosensitive coloring layer.

Thus, a thermosensitive recording material No. 36 according to the present invention was obtained.

EXAMPLE 37

The procedure for preparation of the thermosensitive recording material No. 1 in Example 1 was repeated except that the Compound No. 4 in the Liquid B for the thermosensitive coloring layer coating liquid in Example 1 was replaced by Compound No. 521 shown in TABLE 1.

Thus, a thermosensitive recording material No. 37 according to the present invention was obtained.

EXAMPLE 38

The procedure for preparation of the thermosensitive recording material No. 1 in Example 1 was repeated except that the Compound No. 4 in the Liquid B for the thermosensitive coloring layer coating liquid in Example 1 was replaced by Compound No. 528 shown in TABLE 1.

Thus, a thermosensitive recording material No. 38 according to the present invention was obtained.

EXAMPLE 39

The procedure for preparation of the thermosensitive recording material No. 1 in Example 1 was repeated except that the Compound No. 4 in the Liquid B for the thermosensitive coloring layer coating liquid in Example 1 was replaced by Compound No. 676 shown in TABLE 1.

Thus, a thermosensitive recording material No. 39 according to the present invention was obtained.

EXAMPLE 40

The procedure for preparation of the thermosensitive recording material No. 1 in Example 1 was repeated except that the Compound No. 4 in the Liquid B for the thermosensitive coloring layer coating liquid in Example 1 was replaced by Compound No. 689 shown in TABLE 1.

Thus, a thermosensitive recording material No. 40 according to the present invention was obtained.

EXAMPLE 41

The procedure for preparation of the thermosensitive recording material No. 1 in Example 1 was repeated except that the Compound No. 4 in the Liquid B for the thermosensitive coloring layer coating liquid in Example 1 was replaced by Compound No. 681 shown in TABLE 1.

Thus, a thermosensitive recording material No. 41 according to the present invention was obtained.

EXAMPLE 42

The procedure for preparation of the thermosensitive recording material No. 1 in Example 1 was repeated except that the Compound No. 4 in the Liquid B for the thermosensitive coloring layer coating liquid in Example 1 was replaced by Compound No. 694 shown in TABLE 1.

Thus, a thermosensitive recording material No. 42 according to the present invention was obtained.

EXAMPLE 43

The procedure for preparation of the thermosensitive recording material No. 1 in Example 1 was repeated except that the Compound No. 4 in the Liquid B for the thermosensitive coloring layer coating liquid in Example 1 was replaced by Compound No. 686 shown in TABLE 1.

Thus, a thermosensitive recording material No. 43 according to the present invention was obtained.

EXAMPLE 44

The procedure for preparation of the thermosensitive recording material No. 1 in Example 1 was repeated except that the Compound No. 4 in the Liquid B for the thermosensitive coloring layer coating liquid in Example 1 was replaced by Compound No. 699 shown in TABLE 1.

Thus, a thermosensitive recording material No. 44 according to the present invention was obtained.

EXAMPLE 45

The procedure for preparation of the thermosensitive recording material No. 1 in Example 1 was repeated except that the Compound No. 4 in the Liquid B for the thermosensitive coloring layer coating liquid in Example 1 was replaced by Compound No. 702 shown in TABLE 1.

Thus, a thermosensitive recording material No. 45 according to the present invention was obtained.

EXAMPLE 46

The procedure for preparation of the thermosensitive recording material No. 1 in Example 1 was repeated except that the Compound No. 4 in the Liquid B for the thermosensitive coloring layer coating liquid in Example 1 was replaced by Compound No. 715 shown in TABLE 1.

Thus, a thermosensitive recording material No. 46 according to the present invention was obtained.

EXAMPLE 47

The procedure for preparation of the thermosensitive recording material No. 1 in Example 1 was repeated except that the Compound No. 4 in the Liquid B for the thermosensitive coloring layer coating liquid in Example 1 was replaced by Compound No. 707 shown in TABLE 1.

Thus, a thermosensitive recording material No. 47 according to the present invention was obtained.

EXAMPLE 48

The procedure for preparation of the thermosensitive recording material No. 1 in Example 1 was repeated except that the Compound No. 4 in the Liquid B for the thermosensitive coloring layer coating liquid in Example 1 was replaced by Compound No. 721 shown in TABLE 1.

Thus, a thermosensitive recording material No. 48 according to the present invention was obtained.

EXAMPLE 49

The procedure for preparation of the thermosensitive recording material No. 1 in Example 1 was repeated except that the Compound No. 4 in the Liquid B for the thermosensitive coloring layer coating liquid in Example 1 was replaced by Compound No. 712 shown in TABLE 1.

Thus, a thermosensitive recording material No. 49 according to the present invention was obtained.

EXAMPLE 50

The procedure for preparation of the thermosensitive recording material No. 1 in Example 1 was repeated except that the Compound No. 4 in the Liquid B for the thermosensitive coloring layer coating liquid in Example 1 was replaced by Compound No. 726 shown in TABLE 1.

Thus, a thermosensitive recording material No. 50 according to the present invention was obtained.

EXAMPLE 51

The procedure for preparation of the thermosensitive recording material No. 39 in Example 39 was repeated except that the intermediate layer employed in Example 39 was not interposed between the support and the thermosensitive coloring layer.

Thus, a thermosensitive recording material No. 51 according to the present invention was obtained.

Comparative Example 8

The procedure for preparation of the thermosensitive recording material No. 1 in Example 1 was repeated except that the Compound No. 4 in the Liquid B for the thermosensitive coloring layer coating liquid in Example 1 was replaced by 2,4'-dihydroxydiphenylsulfone.

Thus, a comparative thermosensitive recording material No. 8 was obtained.

Comparative Example 9

The procedure for preparation of the thermosensitive recording material No. 1 in Example 1 was repeated except that the Compound No. 4 in the Liquid B for the thermosensitive coloring layer coating liquid in Example 1 was replaced by the following compound:

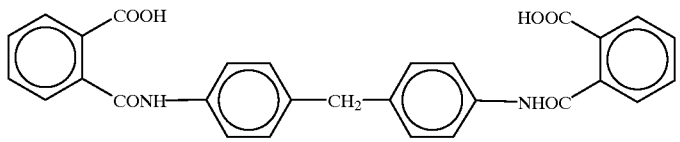

Thus, a comparative thermosensitive recording material No. 9 was obtained.

Comparative Example 10

The procedure for preparation of the thermosensitive recording material No. 1 in Example 1 was repeated except that the Compound No. 4 in the Liquid B for the thermosensitive coloring layer coating liquid in Example 1 was replaced by the following compound:

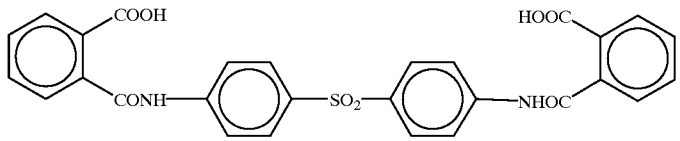

Thus, a comparative thermosensitive recording material No. 10 was obtained.

Comparative Example 11

The procedure for preparation of the thermosensitive recording material No. 1 in Example 1 was repeated except that the Compound No. 4 in the Liquid B for the thermosensitive coloring layer coating liquid in Example 1 was replaced by the following compound:

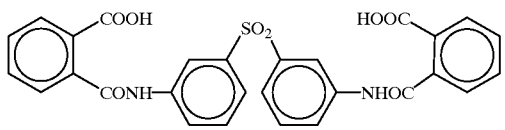

Thus, a comparative thermosensitive recording material No. 11 was obtained.

(Measurement of Coloring Density of Image)

Each of the thermosensitive recording materials Nos. 25 to 51 according to the present invention obtained in Examples 25 to 51 and the comparative thermosensitive recording materials Nos. 8 to 11 obtained in Comparative Examples 8 to 11 was loaded in a printing test apparatus equipped with a commercially available thin film head (made by Matsushita Electronic Components Co., Ltd.), and images were formed on each recording material under the conditions that the applied electric power was 0.68 W/dot, the period for one line was 10 ms/line and the scanning line density was 8×3.85 dot/mm, with the pulse width changed to 0.4 msec, 0.8 msec and 1.2 msec.

The coloring density of the recorded image was measured by a McBeth densitometer.

The results are given in TABLE 4.

(Evaluation of Preservation Stability of Recorded Image)

Images were thermally printed on each of the thermosensitive recording materials in such a manner that a heating block of which temperature was set to a temperature where the image recorded in the recording material showed a saturation coloring density was brought into contact with each recording material for one second with the application of a pressure of 2 kg/cm$^2$ thereto, using a heat gradient tester made by TOYO SEIKI SEISAKU-SHO, Ltd.

The initial coloring density of each image area was measured using the McBeth densitometer.

Then, the plasticizer resistance, the oil resistance and the heat resistance of the image area were evaluated by the following methods.

1. Plasticizer Resistance Test

Three sheets of commercially available polyvinyl chloride wrap, made by Shin-Etsu Polymer Co., Ltd., were overlaid on the image area of each image-bearing sample. Each sample was allowed to stand at 40° C. with the application of a load of 5 kg thereto for 15 hours.

After 15 hours, the density of the image area was measured using the McBeth densitometer.

The results are shown in TABLE 4.

2. Oil Resistance Test

A cotton seed oil was applied to the image area of each image-bearing sample. Each sample was allowed to stand at 40° C. for 15 hours.

After 15 hours, the density of the image area was measured to evaluate the oil resistance.

The results are also shown in TABLE 4.

3. Heat Resistance Test

Each image-bearing sample was allowed to stand at 100° C. for 15 hours. After 15 hours, the density of the image area was measured to evaluate the heat resistance.

The results are also shown in TABLE 4.

TABLE 4

| | Coloring Density | | | Preservation Stability of Recorded Image (Coloring Density) | | | |
|---|---|---|---|---|---|---|---|
| | 0.4 ms | 0.8 ms | 1.2 ms | At initial stage | Plasticizer resistance test | Oil resistance test | Heat resistance test |
| Ex. 25 | 0.15 | 0.95 | 1.16 | 1.11 | 1.03 | 1.13 | 1.11 |
| Ex. 26 | 0.11 | 0.56 | 1.20 | 1.44 | 1.09 | 1.33 | 1.46 |
| Ex. 27 | 0.15 | 0.57 | 1.16 | 1.44 | 1.06 | 1.24 | 1.43 |

TABLE 4-continued

| | Coloring Density | | | At initial stage | Preservation Stability of Recorded Image (Coloring Density) | | |
|---|---|---|---|---|---|---|---|
| | 0.4 ms | 0.8 ms | 1.2 ms | | Plasticizer resistance test | Oil resistance test | Heat resistance test |
| Ex. 28 | 0.14 | 0.87 | 1.09 | 1.06 | 0.91 | 1.04 | 1.06 |
| Ex. 29 | 0.10 | 0.68 | 1.02 | 1.03 | 0.82 | 0.93 | 1.00 |
| Ex. 30 | 0.16 | 0.62 | 1.05 | 1.07 | 0.90 | 0.93 | 0.95 |
| Ex. 31 | 0.18 | 0.78 | 1.15 | 1.10 | 0.98 | 1.00 | 1.01 |
| Ex. 32 | 0.23 | 0.52 | 1.13 | 1.09 | 0.93 | 0.97 | 0.95 |
| Ex. 33 | 0.28 | 1.11 | 1.00 | 1.29 | 1.19 | 1.16 | 1.01 |
| Ex. 34 | 0.26 | 1.15 | 1.11 | 1.33 | 1.04 | 1.07 | 1.23 |
| Ex. 35 | 0.29 | 1.13 | 0.90 | 1.29 | 0.97 | 1.03 | 0.82 |
| Ex. 36 | 0.19 | 0.82 | 1.03 | 1.20 | 0.84 | 1.15 | 1.10 |
| Ex. 37 | 0.19 | 1.00 | 1.08 | 1.13 | 1.08 | 1.10 | 1.23 |
| Ex. 38 | 0.13 | 0.82 | 1.22 | 1.27 | 1.09 | 1.18 | 1.31 |
| Ex. 39 | 0.15 | 0.90 | 1.06 | 1.11 | 1.03 | 1.13 | 1.11 |
| Ex. 40 | 0.17 | 0.86 | 1.02 | 1.02 | 1.04 | 1.03 | 0.98 |
| Ex. 41 | 0.22 | 0.92 | 1.06 | 1.15 | 0.99 | 1.14 | 1.02 |
| Ex. 42 | 0.25 | 0.95 | 1.05 | 1.20 | 0.93 | 1.10 | 0.84 |
| Ex. 43 | 0.10 | 0.68 | 1.02 | 1.03 | 0.82 | 0.93 | 1.00 |
| Ex. 44 | 0.18 | 0.87 | 1.01 | 1.02 | 0.95 | 0.99 | 0.83 |
| Ex. 45 | 0.31 | 1.00 | 1.12 | 1.24 | 1.16 | 1.21 | 0.92 |
| Ex. 46 | 0.29 | 1.01 | 1.10 | 1.20 | 1.13 | 1.16 | 0.99 |
| Ex. 47 | 0.26 | 0.99 | 1.15 | 1.22 | 1.11 | 1.23 | 0.95 |
| Ex. 48 | 0.28 | 1.00 | 1.18 | 1.23 | 1.09 | 1.22 | 0.93 |
| Ex. 49 | 0.19 | 0.92 | 1.09 | 1.15 | 1.03 | 1.13 | 0.89 |
| Ex. 50 | 0.22 | 0.96 | 1.10 | 1.16 | 1.00 | 1.13 | 0.90 |
| Ex. 51 | 0.12 | 0.62 | 0.92 | 1.01 | 0.88 | 0.95 | 0.78 |
| Comp. Ex. 8 | 0.57 | 1.41 | 1.42 | 1.59 | 0.59 | 0.72 | 1.64 |
| Comp. Ex. 9 | 0.17 | 0.77 | 0.75 | 1.01 | 0.68 | 0.78 | 0.45 |
| Comp. Ex. 10 | 0.18 | 0.91 | 1.08 | 1.22 | 1.02 | 1.04 | 0.65 |
| Comp. Ex. 11 | 0.14 | 0.63 | 0.99 | 0.91 | 0.52 | 0.64 | 0.57 |

As can be seen from the results shown in TABLE 4, all the plasticizer resistance, the oil resistance and the heat resistance of the image area formed in the thermosensitive recording material of the present invention are excellent. In addition, when the intermediate layer comprising minute void particles is interposed between the support and the thermosensitive coloring layer, the coloring sensitivity is improved and the preservation stability of the recorded image is excellent.

EXAMPLE 52

The procedure for preparation of the thermosensitive recording material No. 1 in Example 1 was repeated except that the Compound No. 4 in the Liquid B for the thermosensitive coloring layer coating liquid in Example 1 was replaced by Compound No. 668 shown in TABLE 1.

Thus, a thermosensitive recording material No. 52 according to the present invention was obtained.

EXAMPLE 53

The procedure for preparation of the thermosensitive recording material No. 1 in Example 1 was repeated except that the Compound No. 4 in the Liquid B for the thermosensitive coloring layer coating liquid in Example 1 was replaced by Compound No. 663 shown in TABLE 1.

Thus, a thermosensitive recording material No. 53 according to the present invention was obtained.

EXAMPLE 54

The procedure for preparation of the thermosensitive recording material No. 1 in Example 1 was repeated except that the Compound No. 4 in the Liquid B for the thermosensitive coloring layer coating liquid in Example 1 was replaced by Compound No. 673 shown in TABLE 1.

Thus, a thermosensitive recording material No. 54 according to the present invention was obtained.

EXAMPLE 55

The procedure for preparation of the thermosensitive recording material No. 1 in Example 1 was repeated except that the Compound No. 4 in the Liquid B for the thermosensitive coloring layer coating liquid in Example 1 was replaced by Compound No. 671 shown in TABLE 1.

Thus, a thermosensitive recording material No. 55 according to the present invention was obtained.

EXAMPLE 56

The procedure for preparation of the thermosensitive recording material No. 52 in Example 52 was repeated except that the intermediate layer employed in Example 52 was not interposed between the support and the thermosensitive coloring layer.

Thus, a thermosensitive recording material No. 56 according to the present invention was obtained.

Comparative Example 12

The procedure for preparation of the thermosensitive recording material No. 1 in Example 1 was repeated except that the Compound No. 4 in the Liquid B for the thermosensitive coloring layer coating liquid in Example 1 was replaced by 2,4'-dihydroxydiphenylsulfone.

Thus, a comparative thermosensitive recording material No. 12 was obtained.

Comparative Example 13

The procedure for preparation of the thermosensitive recording material No. 1 in Example 1 was repeated except that the Compound No. 4 in the Liquid B for the thermosensitive coloring layer coating liquid in Example 1 was replaced by the following compound:

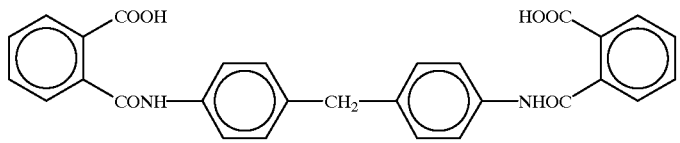

Thus, a comparative thermosensitive recording material No. 13 was obtained.

Comparative Example 14

The procedure for preparation of the thermosensitive recording material No. 1 in Example 1 was repeated except that the Compound No. 4 in the Liquid B for the thermosensitive coloring layer coating liquid in Example 1 was replaced by the following compound:

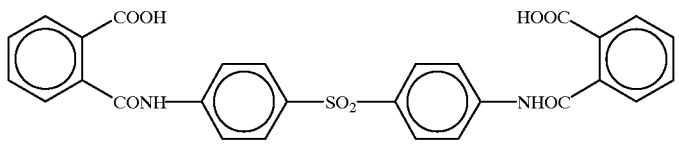

Thus, a comparative thermosensitive recording material No. 14 was obtained.

Comparative Example 15

The procedure for preparation of the thermosensitive recording material No. 1 in Example 1 was repeated except that the Compound No. 4 in the Liquid B for the thermosensitive coloring layer coating liquid in Example 1 was replaced by the following compound:

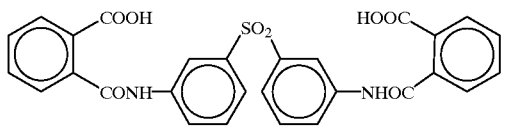

Thus, a comparative thermosensitive recording material No. 15 was obtained.

(Measurement of Coloring Density of Image)

Each of the thermosensitive recording materials Nos. 52 to 56 according to the present invention obtained in Examples 52 to 56 and the comparative thermosensitive recording materials Nos. 12 to 15 obtained in Comparative Examples 12 to 15 was loaded in a printing test apparatus equipped with a commercially available thin film head (made by Matsushita Electronic Components Co., Ltd.), and images were formed on each recording material under the conditions that the applied electric power was 0.68 W/dot, the period for one line was 10 ms/line and the scanning line density was 8×3.85 dot/mm, with the pulse width changed to 0.4 msec, 0.8 msec and 1.2 msec.

The coloring density of the recorded image was measured by a McBeth densitometer.

The results are given in TABLE 5.

(Evaluation of Preservation Stability of Recorded Image)

Images were thermally printed on each of the thermosensitive recording materials in such a manner that a heating block of which temperature was set to a temperature where the image recorded in the recording material showed a saturation coloring density was brought into contact with each recording material for one second with the application of a pressure of 2 kg/cm² thereto, using a heat gradient tester made by TOYO SEIKI SEISAKU-SHO, Ltd.

The initial coloring density of each image area was measured using the McBeth densitometer.

Then, the plasticizer resistance and the water resistance of the image area on each image-bearing sample were evaluated by the following methods.

1. Plasticizer Resistance Test

Three sheets of commercially available polyvinyl chloride wrap, made by Shin-Etsu Polymer Co., Ltd., were overlaid on the image area of each image-bearing sample. Each sample was allowed to stand at 40° C. with the application of a load of 5 kg thereto for 15 hours.

After 15 hours, the density of the image area was measured using the McBeth densitometer.

The results are shown in TABLE 5.

2. Water Resistance Test

Each image-bearing sample was immersed in water, and thereafter allowed to stand at room temperature for 15 hours.

After 15 hours, the density of the image area was measured to evaluate the water resistance.

The results are also shown in TABLE 5.

TABLE 5

| | Coloring Density | | | Preservation Stability of Recorded Image (Coloring Density) | | |
|---|---|---|---|---|---|---|
| | | | | At initial stage | Plasticizer resistance test | Water resistance test |
| | 0.4 ms | 0.8 ms | 1.2 ms | | | |
| Ex. 52 | 0.23 | 0.92 | 1.04 | 1.09 | 0.93 | 0.88 |
| Ex. 53 | 0.14 | 0.86 | 1.05 | 1.01 | 0.99 | 0.91 |
| Ex. 54 | 0.19 | 0.87 | 1.02 | 1.03 | 0.80 | 0.92 |
| Ex. 55 | 0.20 | 0.85 | 1.01 | 1.01 | 0.92 | 0.81 |
| Ex. 56 | 0.15 | 0.66 | 0.82 | 0.82 | 0.76 | 0.75 |
| Comp. Ex. 12 | 0.57 | 1.41 | 1.42 | 1.59 | 0.59 | 1.30 |
| Comp. Ex. 13 | 0.17 | 0.77 | 0.75 | 1.01 | 0.68 | 0.54 |
| Comp. Ex. 14 | 0.18 | 0.91 | 1.08 | 1.22 | 1.02 | 0.73 |
| Comp. Ex. 15 | 0.14 | 0.63 | 0.99 | 0.91 | 0.52 | 0.76 |

As can be seen from the results shown in TABLE 5, the plasticizer resistance and the water resistance of the image area formed in the thermosensitive recording material of the present invention are excellent. In addition, when the intermediate layer comprising minute void particles is interposed between the support and the thermosensitive coloring layer, the coloring sensitivity is improved and the preservation stability of the recorded image is excellent.

Preparation Example 1

[Synthesis of Compound No. 1 shown in TABLE 1]

19.3 g of 3-nitrophthalic anhydride and 3.1 g of ethylene glycol were dispersed in 100 ml of toluene. This reaction mixture was refluxed for 5 hours.

After the reaction mixture was cooled to room temperature, the toluene was distilled away from the reaction mixture under reduced pressure, thereby obtaining a white solid.

The white solid material thus obtained was dispersed in 600 ml of water and heated to 80° C. Then, the mixture was stirred for 2 hours, and cooled to room temperature.

Thereafter, the mixture was filtered, so that white crystals were obtained. The white crystals were recrystallized from a 50% aqueous solution of ethanol, thereby obtaining the Compound No. 1 as white crystals in a yield of 12.4 g.

The melting point of this compound was 240 to 243° C.

FIG. 1 is an infrared spectrum of the Compound No. 1.

Preparation Example 2
[Synthesis of Compound No. 3 shown in TABLE 1]
19.3 g of 3-nitrophthalic anhydride and 4.5 g of 1,4-butanediol were dispersed in 100 ml of toluene. This reaction mixture was refluxed for 5 hours.

After the reaction mixture was cooled to room temperature, the toluene was distilled away from the reaction mixture under reduced pressure, thereby obtaining a white solid.

The white solid material thus obtained was dispersed in 600 ml of water and heated to 80° C. Then, the mixture was stirred for 2 hours, and cooled to room temperature.

Thereafter, the mixture was filtered, so that white crystals were obtained. The white crystals were recrystallized from a 50% aqueous solution of ethanol, thereby obtaining the Compound No. 3 as white crystals in a yield of 12.6 g.

The melting point of this compound was 205 to 207° C.

Figure 2:
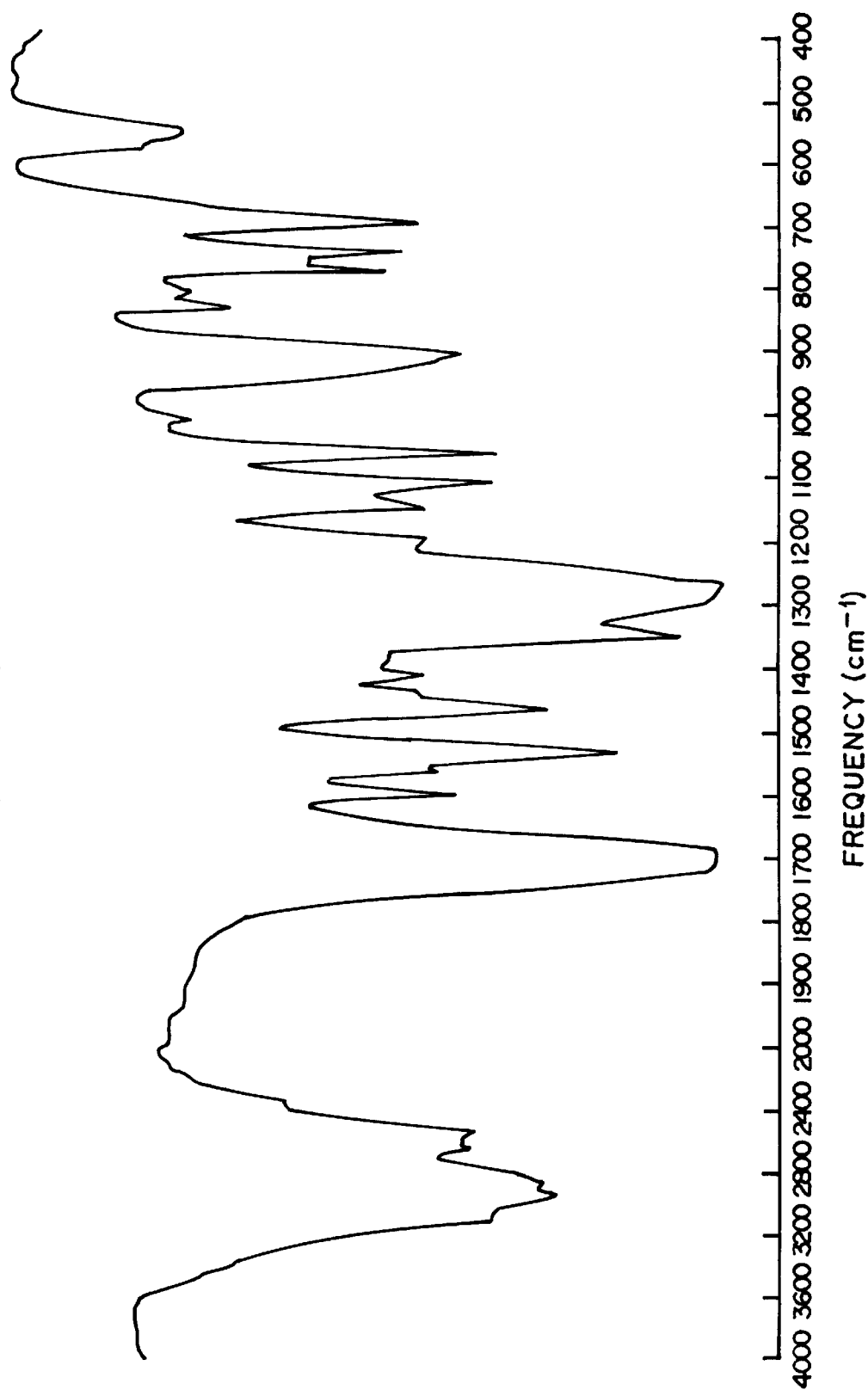
FIG. 2 is an IR spectrum of a compound No. 3 obtained in Preparation Example 2.

FIG. 2 is an infrared spectrum of the Compound No. 3.

Preparation Example 3
[Synthesis of Compound No. 4 shown in TABLE 1]
19.3 g of 3-nitrophthalic anhydride and 5.2 g of 1,5-pentanediol were dispersed in 100 ml of toluene. This reaction mixture was refluxed for 6 hours.

After the reaction mixture was cooled to room temperature, the toluene was distilled away from the reaction mixture under reduced pressure, thereby obtaining a white solid.

The white solid material thus obtained was dispersed in 500 ml of water and heated to 80° C. Then, the mixture was stirred for 2 hours, and cooled to room temperature.

Thereafter, the mixture was filtered, so that white crystals were obtained. The white crystals were recrystallized from a 50% aqueous solution of ethanol, thereby obtaining the Compound No. 4 as white crystals in a yield of 12.1 g.

The melting point of this compound was 213 to 217° C.

Figure 3:
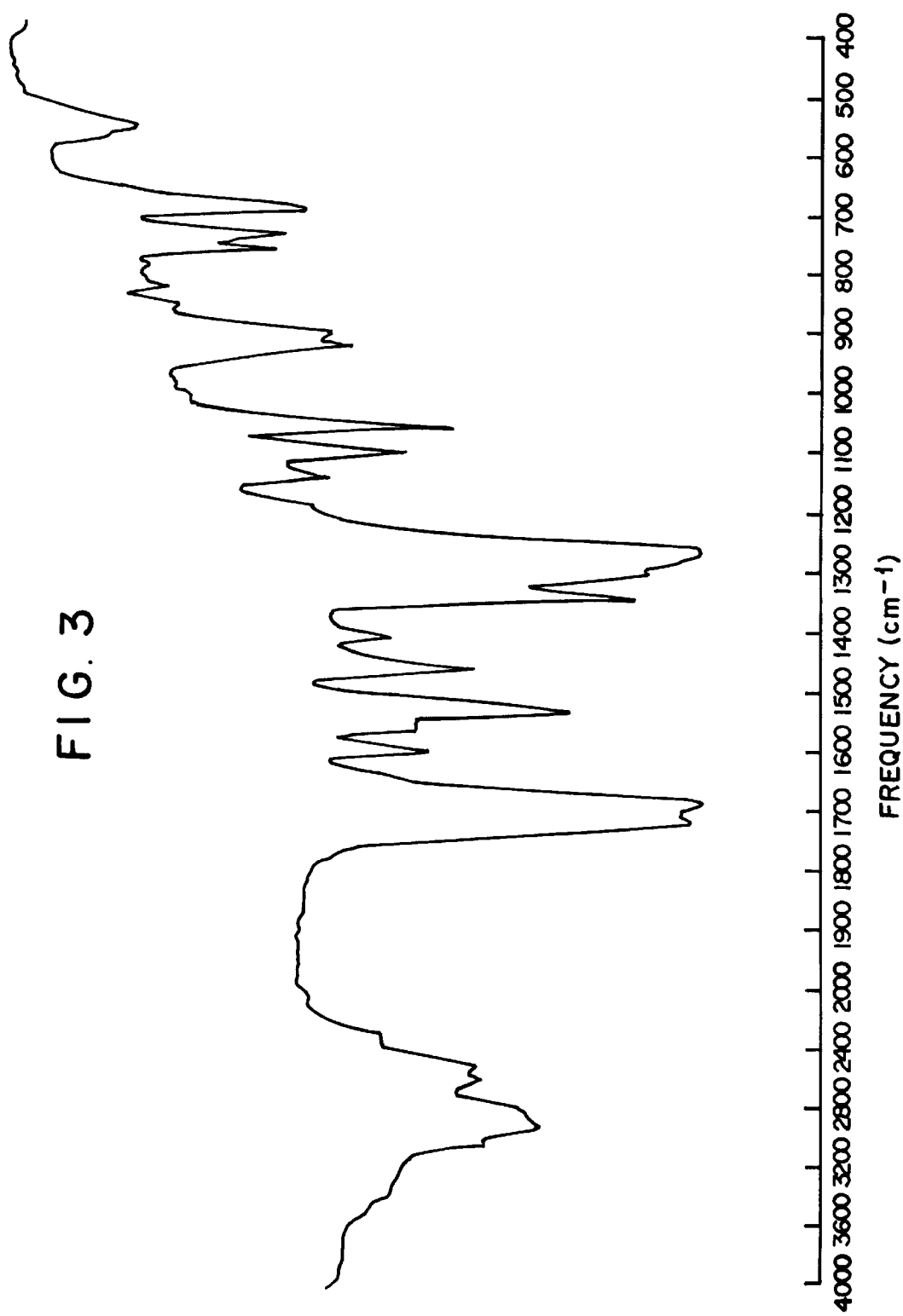
FIG. 3 is an IR spectrum of a compound No. 4 obtained in Preparation Example 3.

FIG. 3 is an infrared spectrum of the Compound No. 4.

Preparation Example 4
[Synthesis of Compound No. 5 shown in TABLE 1]
19.3 g of 3-nitrophthalic anhydride and 5.9 g of 1,6-hexanediol were dispersed in 150 ml of toluene. This reaction mixture was refluxed for 6 hours.

After the reaction mixture was cooled to room temperature, the toluene was distilled away from the reaction mixture under reduced pressure, thereby obtaining a white solid.

The white solid material thus obtained was dispersed in 500 ml of water and heated to 80° C. Then, the mixture was stirred for 2 hours, and cooled to room temperature.

Thereafter, the mixture was filtered, so that white crystals were obtained. The white crystals were recrystallized from a 50% aqueous solution of ethanol, thereby obtaining the Compound No. 5 as white crystals in a yield of 12.8 g.

The melting point of this compound was 211 to 214° C.

Figure 4:
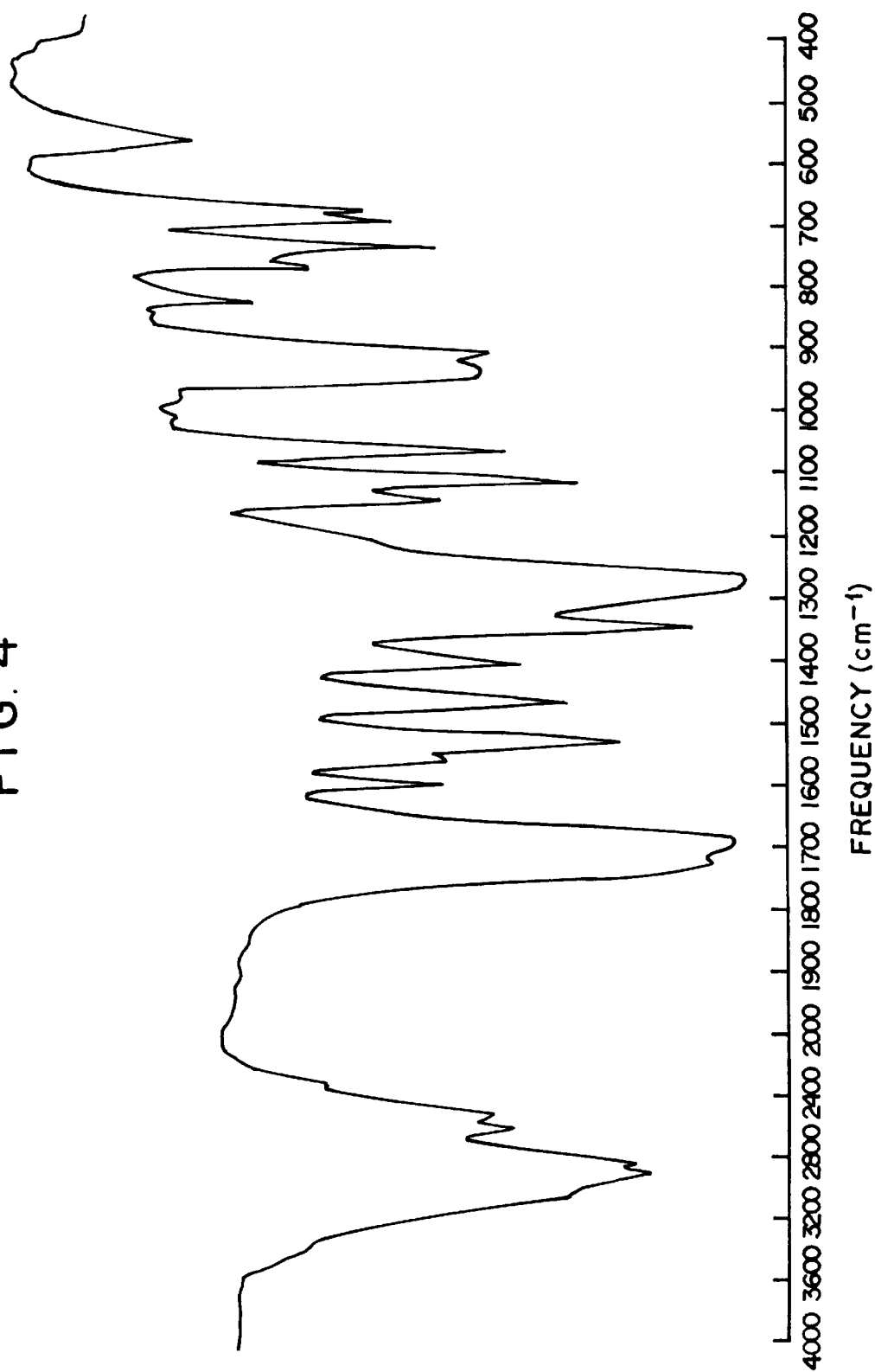
FIG. 4 is an IR spectrum of a compound No. 5 obtained in Preparation Example 4.

FIG. 4 is an infrared spectrum of the Compound No. 5.

Preparation Example 5
[Synthesis of Compound No. 6 shown in TABLE 1]
9.7 g of 3-nitrophthalic anhydride and 3.7 g of 1,8-octanediol were dispersed in 100 ml of toluene. This reaction mixture was refluxed for 13 hours.

After the reaction mixture was cooled to room temperature, the toluene was distilled away from the reaction mixture under reduced pressure, thereby obtaining a white solid.

The white solid material thus obtained was dispersed in 800 ml of water and heated to 80° C. Then, the mixture was stirred for 2 hours, and cooled to room temperature.

Thereafter, the mixture was filtered, so that white crystals were obtained. The white crystals were recrystallized from a 50% aqueous solution of ethanol, thereby obtaining the Compound No. 6 as white crystals in a yield of 5.2 g.

The melting point of this compound was 168 to 171° C.

Figure 5:
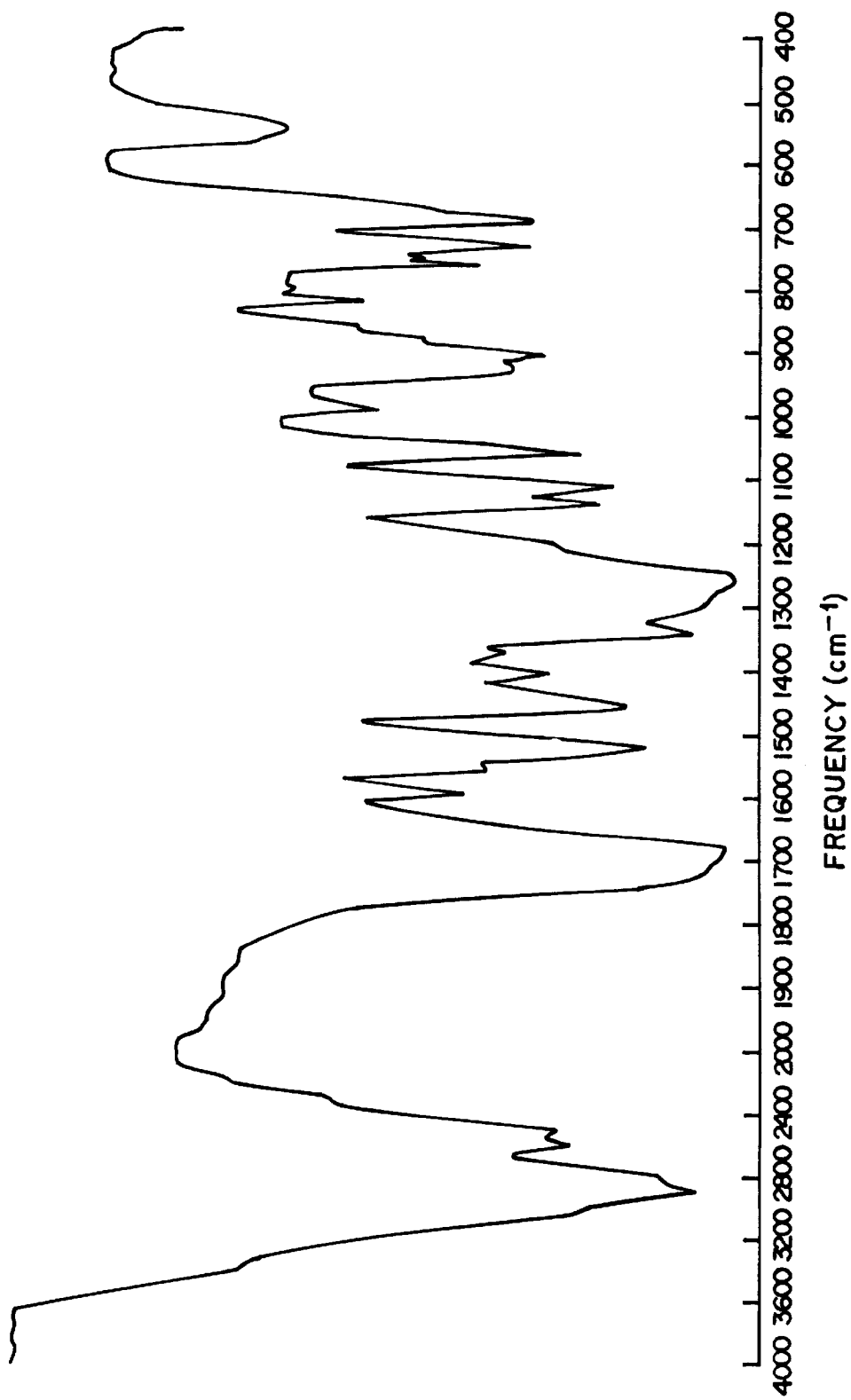
FIG. 5 is an IR spectrum of a compound No. 6 obtained in Preparation Example 5.

FIG. 5 is an infrared spectrum of the Compound No. 6.

Preparation Example 6
[Synthesis of Compound No. 10 shown in TABLE 1]
9.6 g of 3-nitrophthalic anhydride and 5.6 g of 1,12-dodecanediol were dispersed in 100 ml of toluene. This reaction mixture was refluxed for 13 hours.

After the reaction mixture was cooled to room temperature, the toluene was distilled away from the reaction mixture under reduced pressure, thereby obtaining a yellow viscous material.

The yellow viscous material thus obtained was dispersed in 600 ml of water and heated to 80° C. Then, the mixture was stirred for 2 hours, and cooled to room temperature.

Thereafter, the mixture was filtered, so that white crystals were obtained. The white crystals were recrystallized from a 50% aqueous solution of ethanol, thereby obtaining the Compound No. 10 as white crystals in a yield of 6.0 g.

The melting point of this compound was 105 to 110° C.

Figure 6:
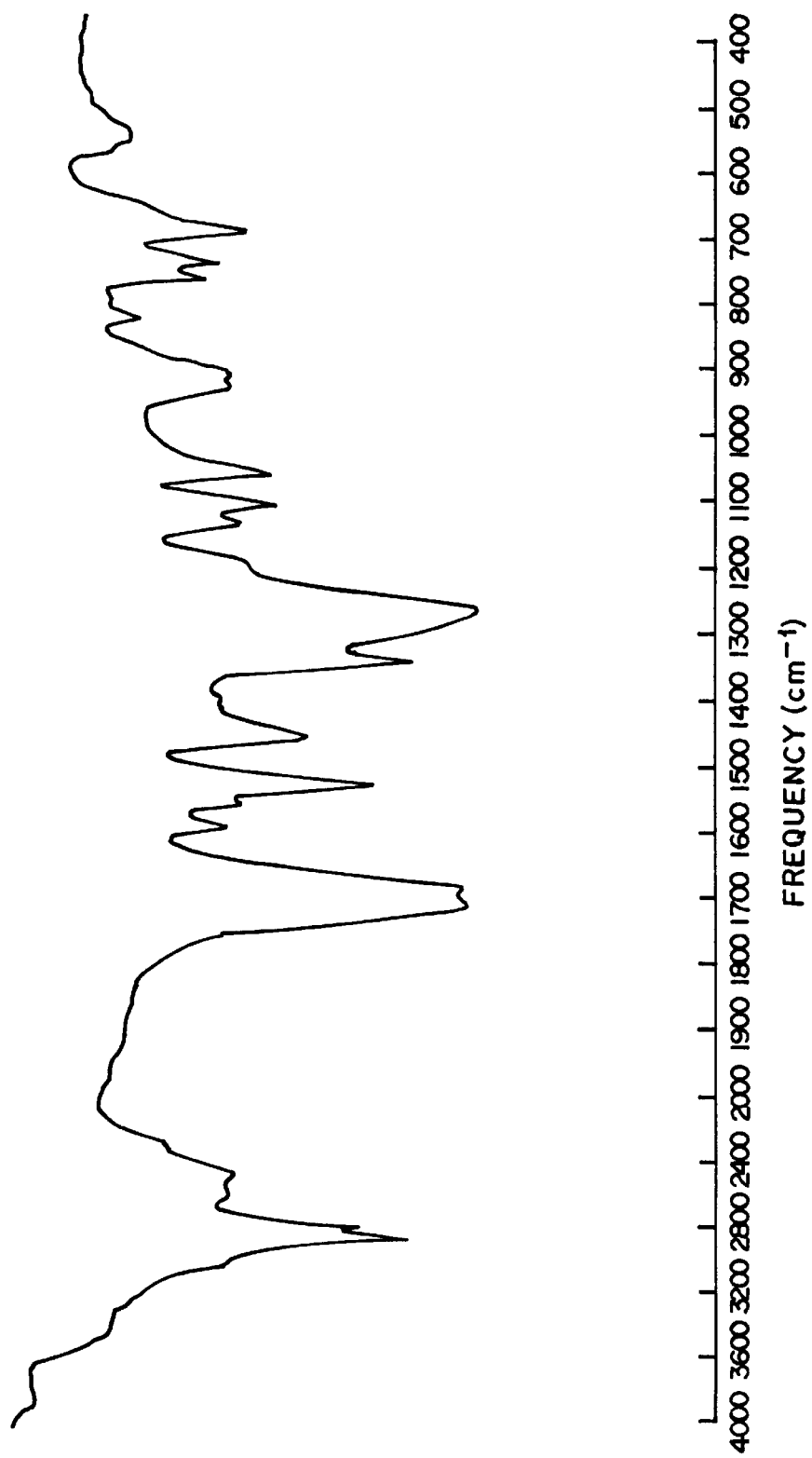
FIG. 6 is an IR spectrum of a compound No. 10 obtained in Preparation Example 6.

FIG. 6 is an infrared spectrum of the Compound No. 10.

Preparation Example 7
[Synthesis of Compound No. 11 shown in TABLE 1]
50.0 g of 3-nitrophthalic anhydride and 13.0 g of diethylene glycol were dispersed in 250 ml of toluene. This reaction mixture was refluxed for 5 hours.

After the reaction mixture was cooled to room temperature, the toluene was distilled away from the reaction mixture under reduced pressure, thereby obtaining a white solid.

The white solid material thus obtained was dispersed in 1,000 ml of water and heated to 80° C. Then, the mixture was stirred for 2 hours, and cooled to room temperature.

Thereafter, the mixture was filtered, so that white crystals were obtained. The white crystals were recrystallized from a 30% aqueous solution of ethanol, thereby obtaining the Compound No. 11 as white crystals in a yield of 41.0 g.

The melting point of this compound was 185 to 188° C.

Figure 7:
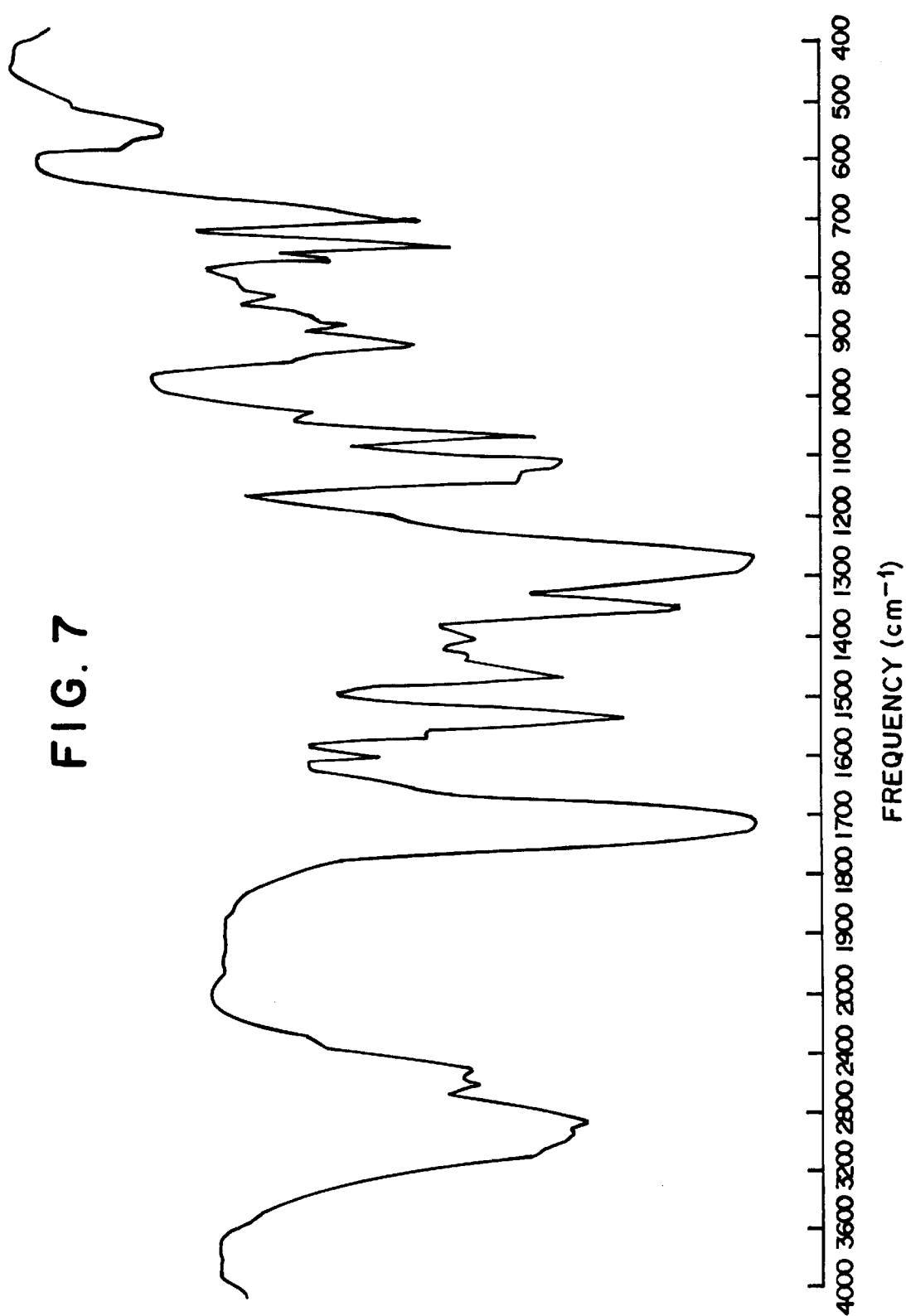
FIG. 7 is an IR spectrum of a compound No. 11 obtained in Preparation Example 7.

FIG. 7 is an infrared spectrum of the Compound No. 11.

Preparation Example 8
[Synthesis of Compound No. 12 shown in TABLE 1]
50.0 g of 3-nitrophthalic anhydride and 19.0 g of triethylene glycol were dispersed in 300 ml of toluene. This reaction mixture was refluxed for 7 hours.

After the reaction mixture was cooled to room temperature, the toluene was distilled away from the reaction mixture under reduced pressure, thereby obtaining a white solid.

The white solid material thus obtained was dispersed in 1,000 ml of water and heated to 80° C. Then, the mixture was stirred for 2 hours, and cooled to room temperature.

Thereafter, the mixture was filtered, so that white crystals were obtained. The white crystals were recrystallized from a 50% aqueous solution of ethanol, thereby obtaining the Compound No. 12 as white crystals in a yield of 35.7 g.

The melting point of this compound was 210 to 212° C.

Figure 8:
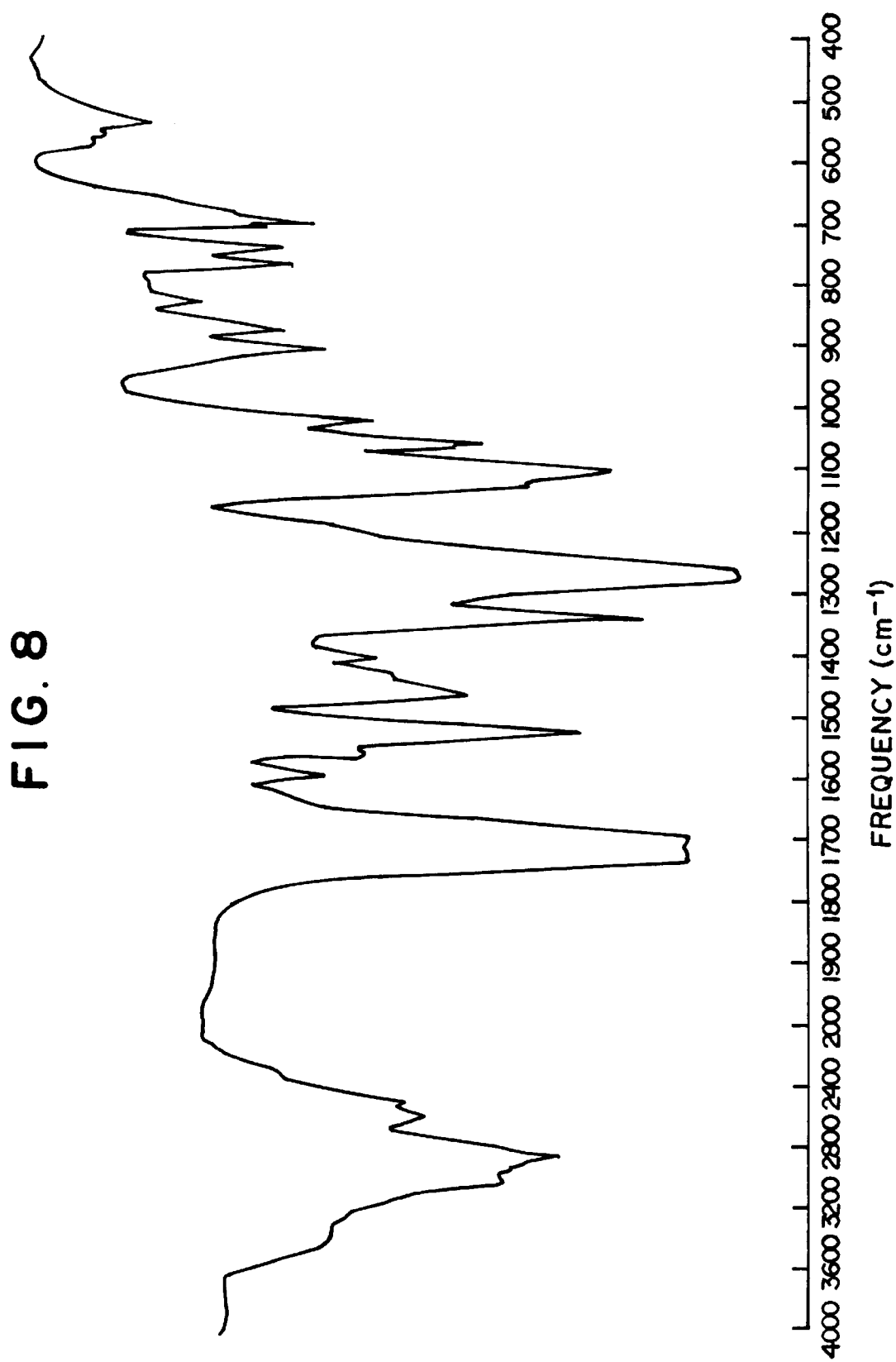
FIG. 8 is an IR spectrum of a compound No. 12 obtained in Preparation Example 8.

FIG. 8 is an infrared spectrum of the Compound No. 12.

Preparation Example 9
[Synthesis of Compound No. 15 shown in TABLE 1]
19.3 g of 3-nitrophthalic anhydride and 6.2 g of p-xylylene glycol were dispersed in 150 ml of toluene. This reaction mixture was refluxed for 6 hours.

After the reaction mixture was cooled to room temperature, the toluene was distilled away from the reaction mixture under reduced pressure, thereby obtaining a white solid.

The white solid material thus obtained was dispersed in 500 ml of water and heated to 80° C. Then, the mixture was stirred for 2 hours, and cooled to room temperature.

Thereafter, the mixture was filtered, so that white crystals were obtained. The white crystals were recrystallized from a 70% aqueous solution of ethanol, thereby obtaining the Compound No. 15 as white crystals in a yield of 3.1 g.

The melting point of this compound was 177 to 180° C.

Figure 9:
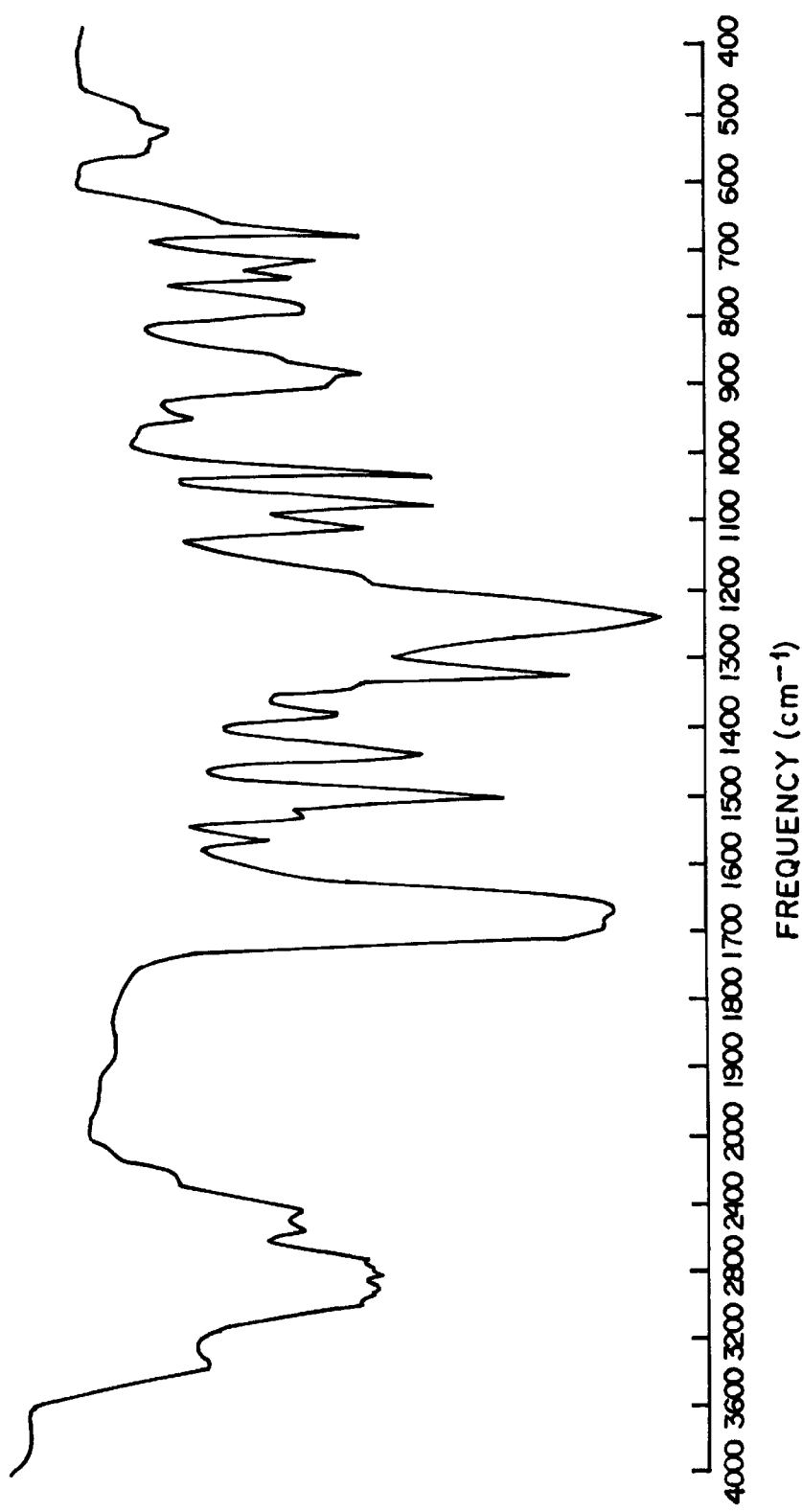
FIG. 9 is an IR spectrum of a compound No. 15 obtained in Preparation Example 9.

FIG. 9 is an infrared spectrum of the Compound No. 15.

Preparation Example 10

[Synthesis of Compound No. 22 shown in TABLE 1]

30 g of 3-nitrophthalic anhydride was dispersed in 200 ml of acetic acid to prepare a dispersion of 3-nitrophthalic anhydride. To this dispersion, 9 g of 1,6-diaminohexane was added in three portions. The resultant reaction mixture was stirred at room temperature for 3 hours.

After the reaction mixture was poured into 1,000 ml of water and stirred at room temperature, white crystals separated out. The white crystals were then collected by filtration and washed with water.

The white crystals thus obtained were dispersed in 1,000 ml of water again. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjusted the filtrate to pH2 to 3, whereby white crystals separated out. The white crystals thus obtained were washed with water and dried under reduced pressure, so that the Compound No. 22 was obtained as white crystals in a yield of 30.6 g.

The melting point of this compound was 179 to 181° C. According to the analysis by thin-layer chromatography (TLC), the $R_f$ value of this compound was 0.09.

Figure 10:
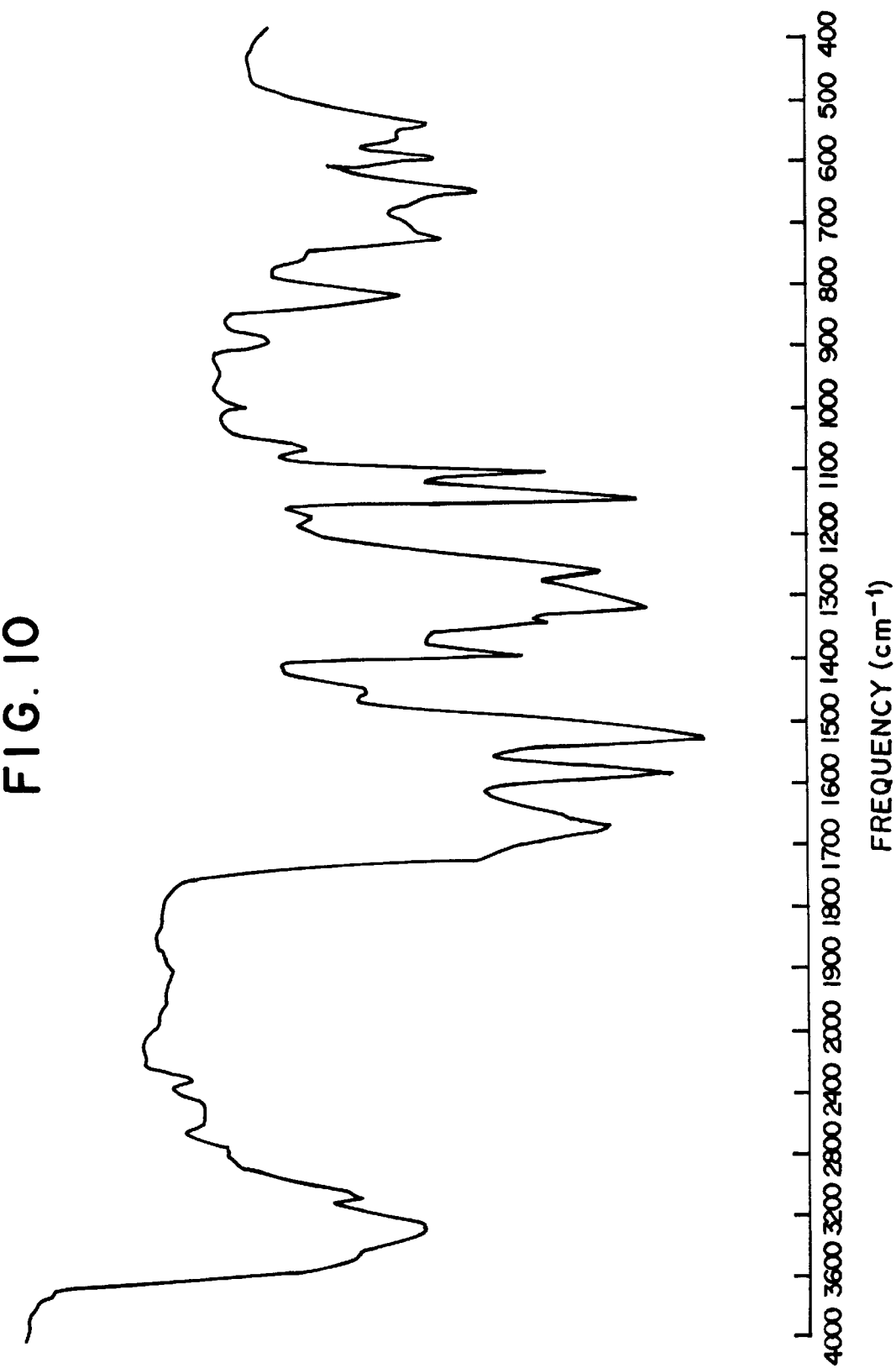
FIG. 10 is an IR spectrum of a compound No. 22 obtained in Preparation Example 10.

FIG. 10 is an infrared spectrum of the Compound No. 22.

Preparation Example 11

[Synthesis of Compound No. 26 shown in TABLE 1]

25 g of 3-nitrophthalic anhydride was dispersed in 200 ml of acetic acid to prepare a dispersion of 3-nitrophthalic anhydride. To this dispersion, 12.6 g of 4,4'-diaminodiphenylmethane was added in three portions. The resultant reaction mixture was stirred at room temperature for 3 hours.

After the reaction mixture was poured into 1,000 ml of water and stirred at room temperature, light yellow crystals separated out. The light yellow crystals were then collected by filtration and washed with water.

The light yellow crystals thus obtained were dispersed in 1,000 ml of water again. A 10% aqueous solution of sodium hydroxide was added dropwise to the thus obtained dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH2 to 3, whereby light yellow crystals separated out. The light yellow crystals thus obtained were washed with water and dried under reduced pressure, so that the Compound No. 26 was obtained as light yellow crystals in a yield of 29.7 g.

The melting point of this compound was 170 to 173° C. According to the analysis by thin-layer chromatography (TLC), the $R_f$ value of this compound was 0.12.

Figure 11:
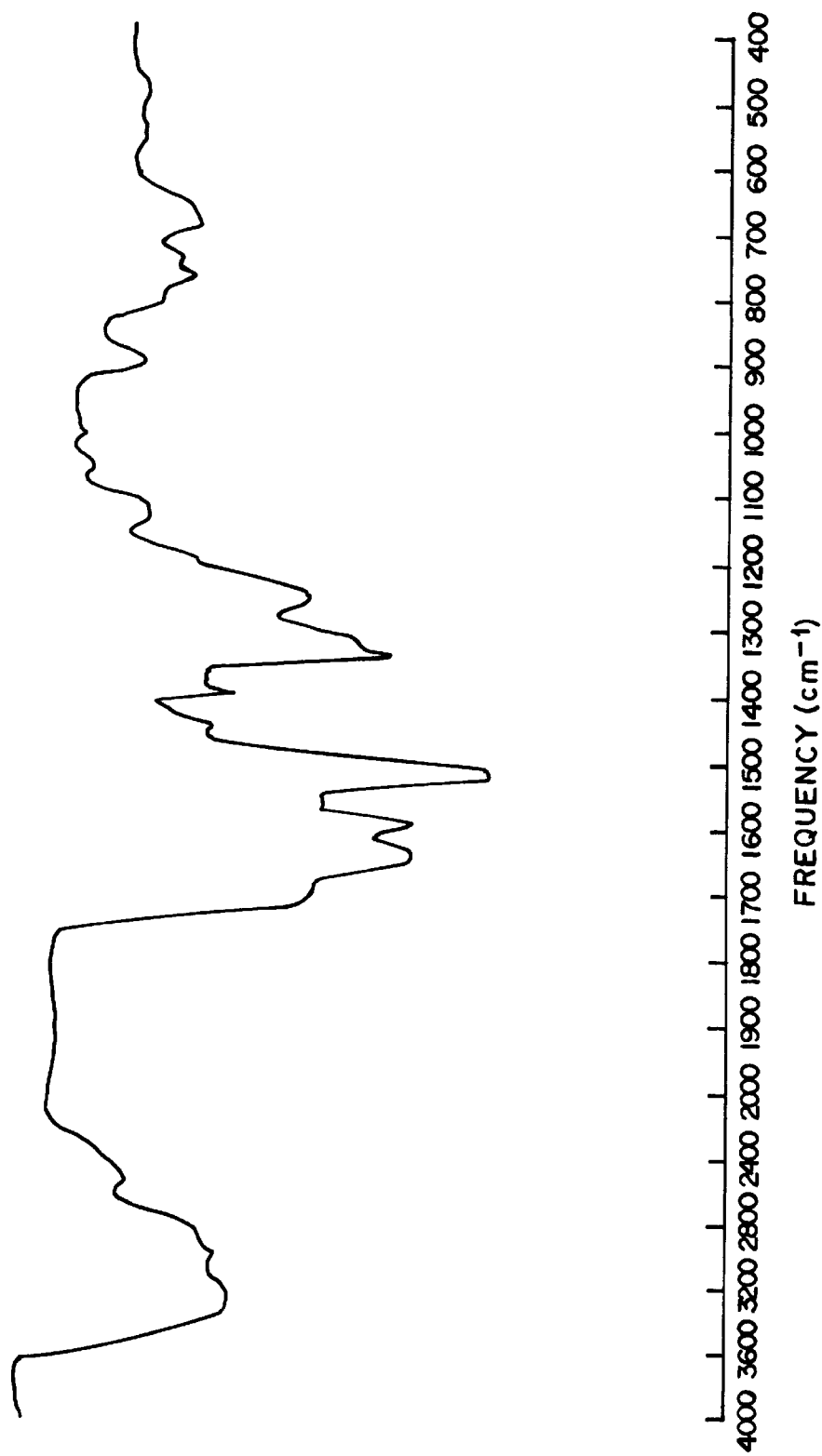
FIG. 11 is an IR spectrum of a compound No. 26 obtained in Preparation Example 11.

FIG. 11 is an infrared spectrum of the Compound No. 26.

Preparation Example 12

[Synthesis of Compound No. 27 shown in TABLE 1]

25 g of 3-nitrophthalic anhydride was dispersed in 200 ml of acetic acid to prepare a dispersion of 3-nitrophthalic anhydride. To this dispersion, 13.0 g of 4,4'-diaminodiphenylether was added in three portions. The resultant reaction mixture was stirred at room temperature for 3 hours.

After the reaction mixture was poured into 1,000 ml of water and stirred at room temperature, light yellow crystals separated out. The light yellow crystals were then collected by filtration and washed with water.

The light yellow crystals thus obtained were dispersed in 1,000 ml of water again. A 10% aqueous solution of sodium hydroxide was added dropwise to the thus obtained dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH2 to 3, whereby light yellow crystals separated out. The light yellow crystals thus obtained were washed with water and dried under reduced pressure, so that the Compound No. 27 was obtained as light yellow crystals in a yield of 31.0 g.

The melting point of this compound was 168 to 175° C. According to the analysis by thin-layer chromatography (TLC), the $R_f$ value of this compound was 0.12.

Figure 12:
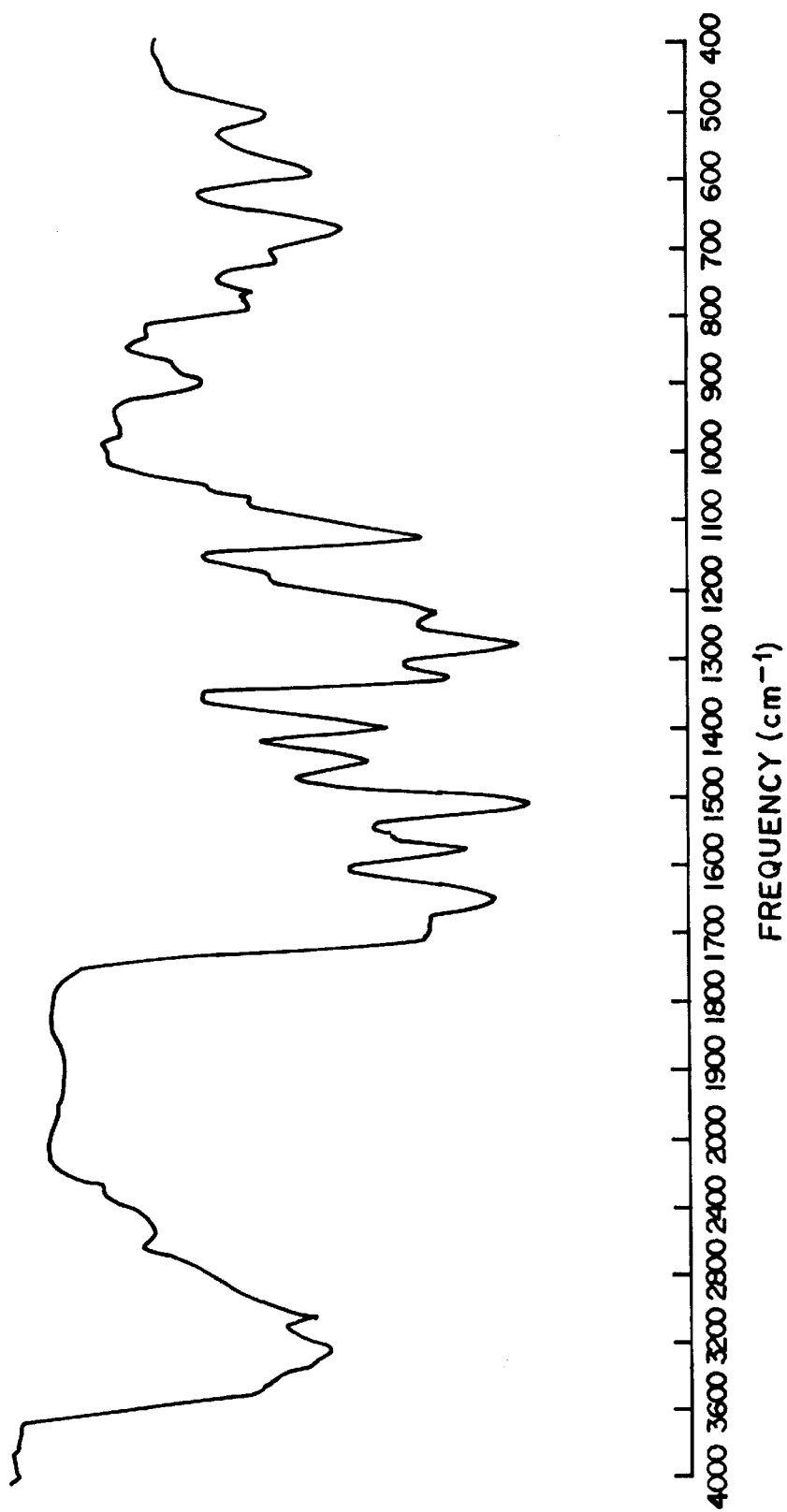
FIG. 12 is an IR spectrum of a compound No. 27 obtained in Preparation Example 12.

FIG. 12 is an infrared spectrum of the Compound No. 27.

Preparation Example 13

[Synthesis of Compound No. 28 shown in TABLE 1]

20 g of 3-nitrophthalic anhydride was dispersed in 200 ml of acetic acid to prepare a dispersion of 3-nitrophthalic anhydride. To this dispersion, 12.0 g of 4,4'-diaminodiphenylsulfone was added in three portions. The resultant reaction mixture was stirred at room temperature for 3 hours.

After the reaction mixture was poured into 1,000 ml of water and stirred at room temperature, white crystals separated out. The white crystals were then collected by filtration and washed with water.

The white crystals thus obtained were dispersed in 1,000 ml of water again. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that the Compound No. 28 was obtained as white crystals in a yield of 26.0 g.

The melting point of this compound was 200 to 202° C. According to the analysis by thin-layer chromatography (TLC), the $R_f$ value of this compound was 0.07.

Figure 13:
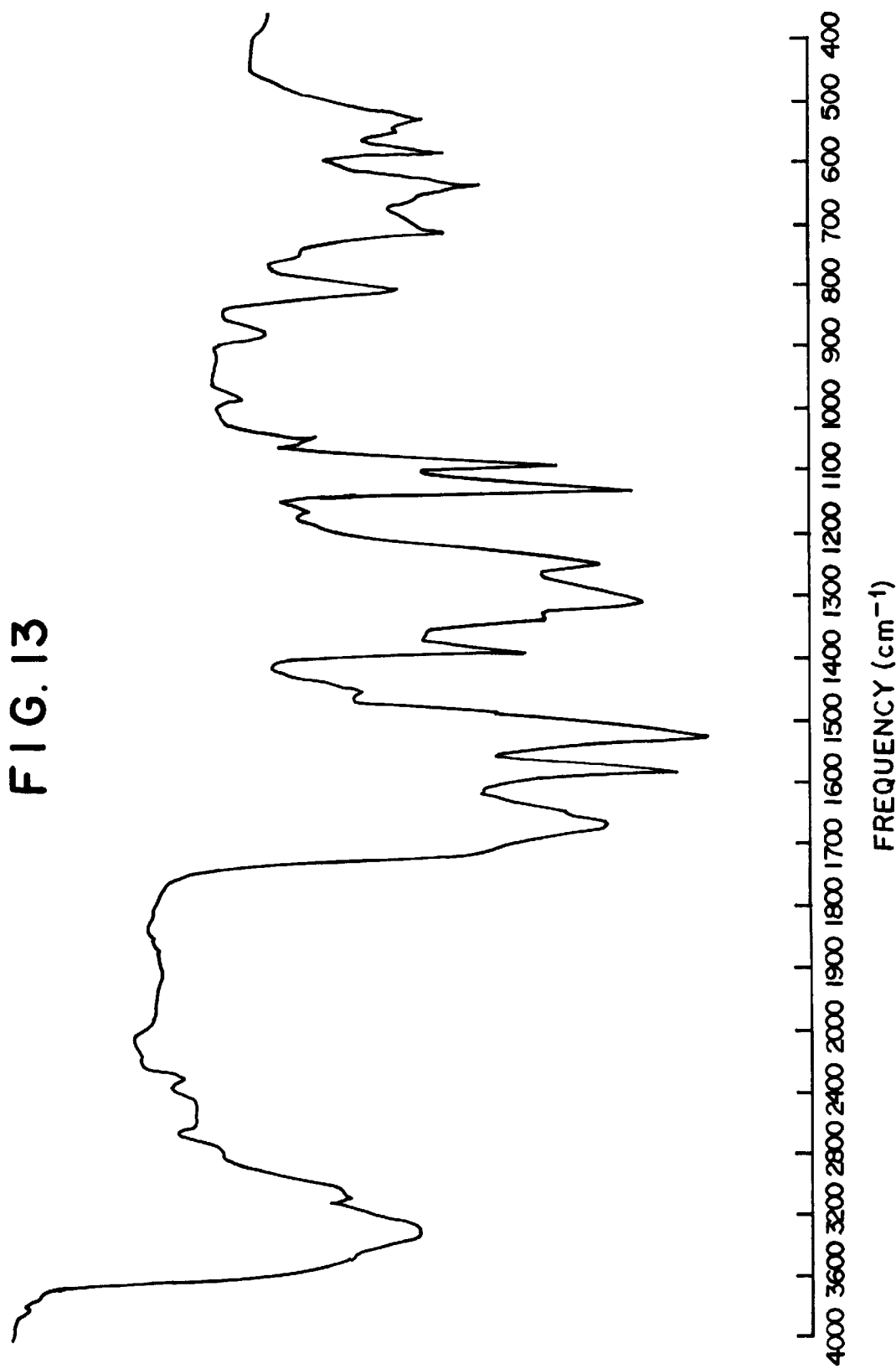
FIG. 13 is an IR spectrum of a compound No. 28 obtained in Preparation Example 13.

FIG. 13 is an infrared spectrum of the Compound No. 28.

Preparation Example 14

[Synthesis of Compound No. 23 shown in TABLE 1]

25 g of 3-nitrophthalic anhydride was dispersed in 200 ml of acetic acid to prepare a dispersion of 3-nitrophthalic anhydride. To this dispersion, 15.0 g of 3,3'-diaminodiphenylsulfone was added in three portions. The resultant reaction mixture was stirred at room temperature for 3 hours.

After the reaction mixture was poured into 1,000 ml of water and stirred at room temperature, white crystals separated out. The white crystals were then collected by filtration and washed with water.

The white crystals thus obtained were dispersed in 1,000 ml of water again. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that the Compound No. 23 was obtained as white crystals in a yield of 29.5 g.

The melting point of this compound was 188 to 190° C. According to the analysis by thin-layer chromatography (TLC), the $R_f$ value of this compound was 0.10.

Figure 14:
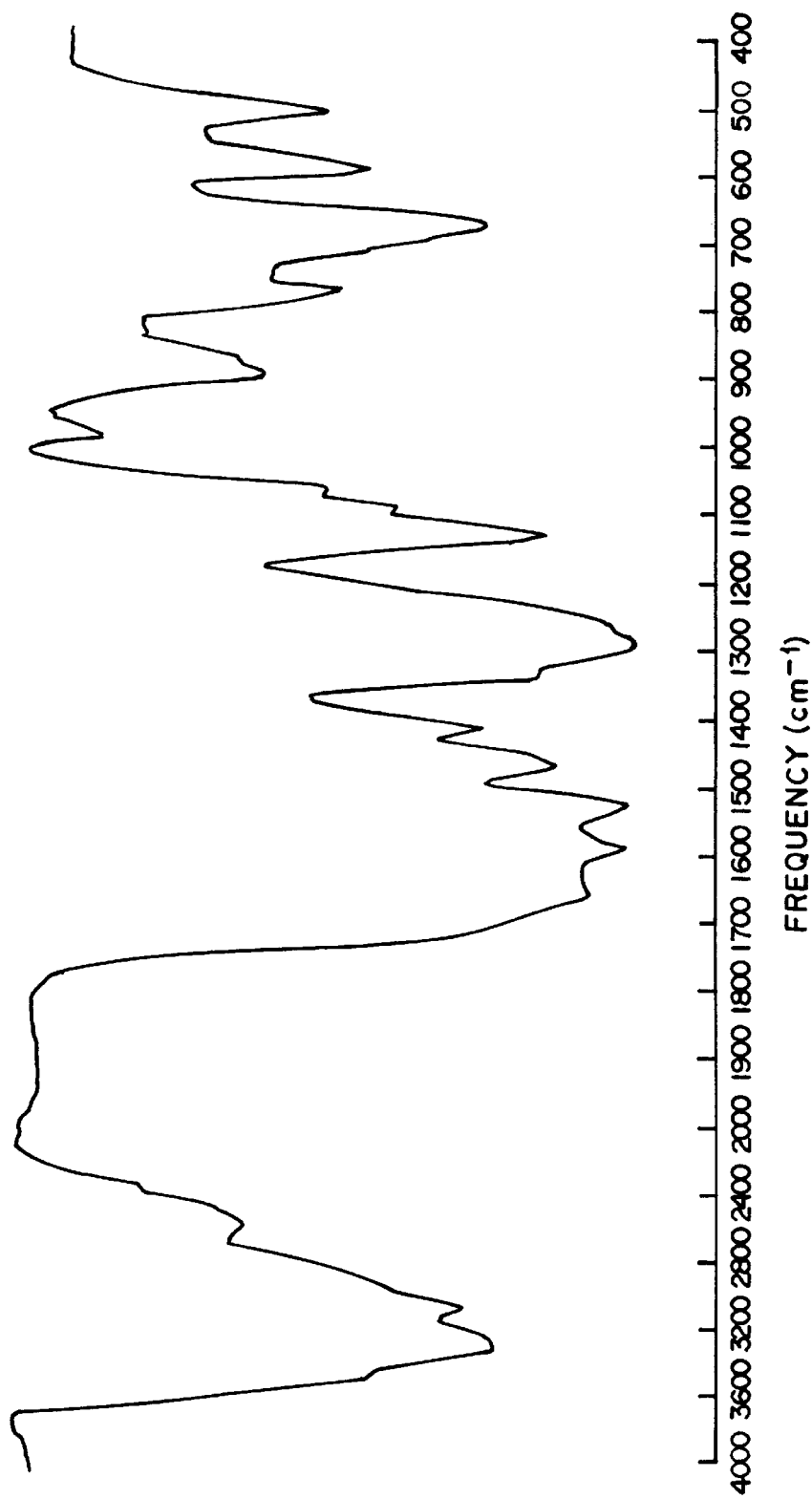
FIG. 14 is an IR spectrum of a compound No. 23 obtained in Preparation Example 14.

FIG. 14 is an infrared spectrum of the Compound No. 23.

Preparation Example 15
[Synthesis of Compound No. 28 shown in TABLE 1]

2.0 g of 3-nitrophthalic anhydride was dissolved in 30 ml of tetrahydrofuran to prepare a solution of 3-nitrophthalic anhydride. To this solution, 1.2 g of 4,4'-diaminodiphenylsulfone was added in three portions. The resultant reaction mixture was stirred at room temperature for 3 hours, whereby white crystals separated out. The white crystals were then collected by filtration and washed with water.

The white crystals thus obtained were dispersed in 100 ml of water. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that the Compound No. 28 was obtained as white crystals in a yield of 2.4 g.

The melting point, the infrared spectrum, and the $R_f$ value of this compound were the same as those previously explained in Preparation Example 13.

Preparation Example 16
[Synthesis of Compound No. 23 shown in TABLE 1]

2.0 g of 3-nitrophthalic anhydride was dispersed in 30 ml of nitrobenzene to prepare a dispersion of 3-nitrophthalic anhydride. To this dispersion, 1.2 g of 4,4'-diaminodiphenylsulfone was added in three portions. The resultant reaction mixture was stirred at room temperature for 3 hours, whereby white crystals separated out. The white crystals were then collected by filtration and washed with hexane.

The white crystals thus obtained were dispersed in 100 ml of water. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that the Compound No. 23 was obtained as white crystals in a yield of 2.2 g.

The melting point, the infrared spectrum, and the $R_f$ value of this compound were the same as those previously explained in Preparation Example 14.

Preparation Example 17
[Synthesis of Compound No. 50 shown in TABLE 1]

50 g of 3-nitrophthalic anhydride was dissolved in 200 ml of acetic anhydride. Part of 3nitrophthalic anhydride remained insoluble and dispersed in the liquid. To this liquid, 14 g of 1,6-diaminohexane was added in about 20 portions over a period of about one hour. The resultant reaction mixture was stirred for 3 hours.

When the reaction mixture was poured into 1,000 ml of water, white crystals separated out. The white crystals were then collected by filtration and washed with water.

The white crystals thus obtained were dispersed in 500 ml of water again. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that the Compound No. 50 was obtained as white crystals in a yield of 8.0 g.

The melting point of this compound was 173 to 176° C. According to the analysis by thin-layer chromatography (TLC), the $R_f$ value of this compound was 0.22.

Figure 15:
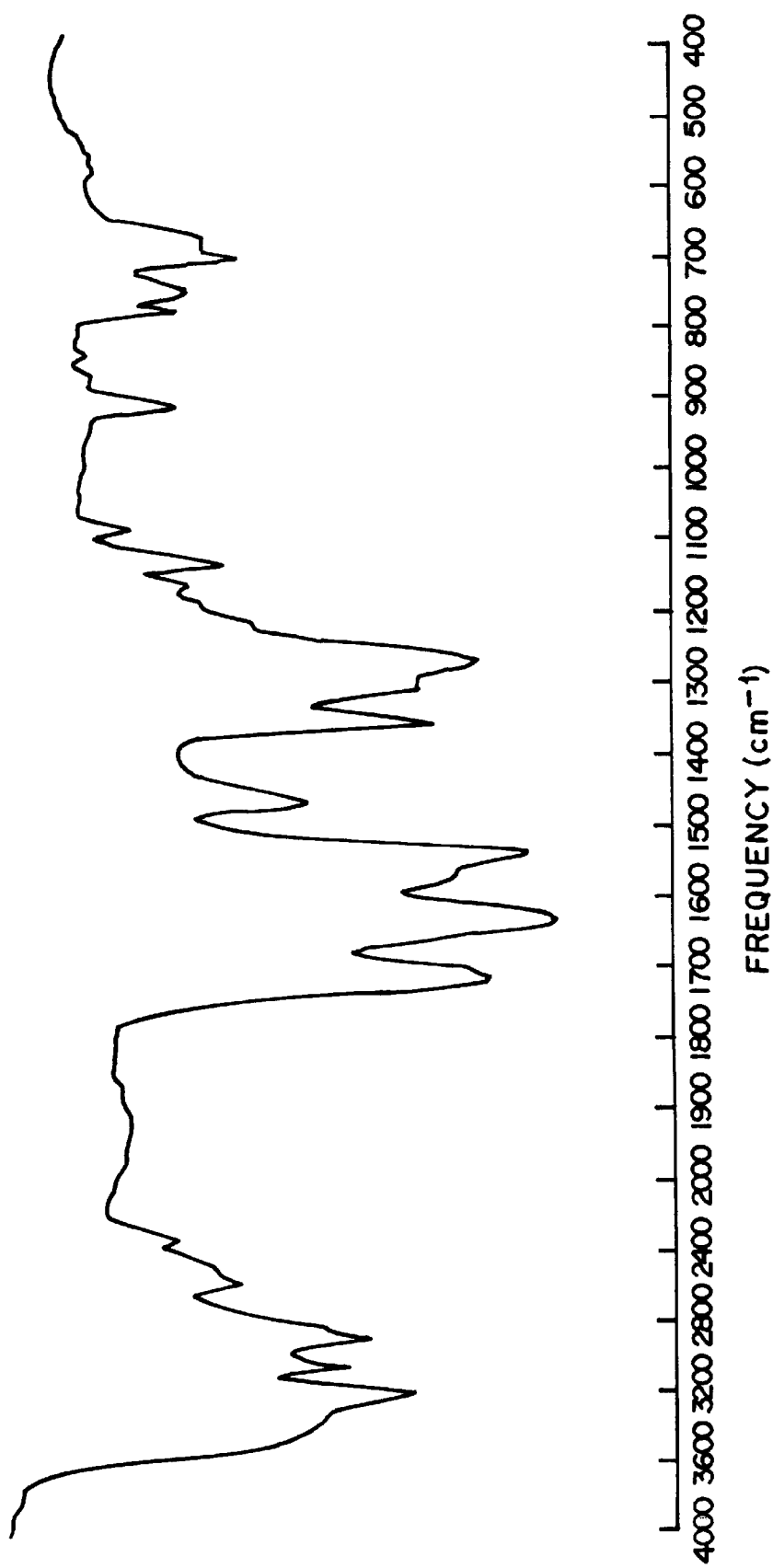
FIG. 15 is an IR spectrum of a compound No. 50 obtained in Preparation Example 17.

FIG. 15 is an infrared spectrum of the Compound No. 50.

Preparation Example 18
[Synthesis of Compound No. 54 shown in TABLE 1]

50 g of 3-nitrophthalic anhydride was dissolved in 100 ml of acetic anhydride. Part of 3-nitrophthalic anhydride remained insoluble and dispersed in the liquid. To this liquid, 24 g of 4,4'-diaminodiphenylmethane was added in about 20 portions over a period of about one hour. The resultant reaction mixture was stirred for 3 hours.

When the reaction mixture was poured into 1,000 ml of water, light yellow crystals separated out. The light yellow crystals were then collected by filtration and washed with water.

The light yellow crystals thus obtained were dispersed in 500 ml of water again. A 10% aqueous solution of sodium hydroxide was added dropwise to the thus obtained dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH2 to 3, whereby light yellow crystals separated out. The light yellow crystals thus obtained were washed with water and dried under reduced pressure, so that the Compound No. 54 was obtained as light yellow crystals in a yield of 12 g.

The melting point of this compound was 161 to 165° C. According to the analysis by thin-layer chromatography (TLC), the $R_f$ value of this compound was 0.33.

Figure 16:
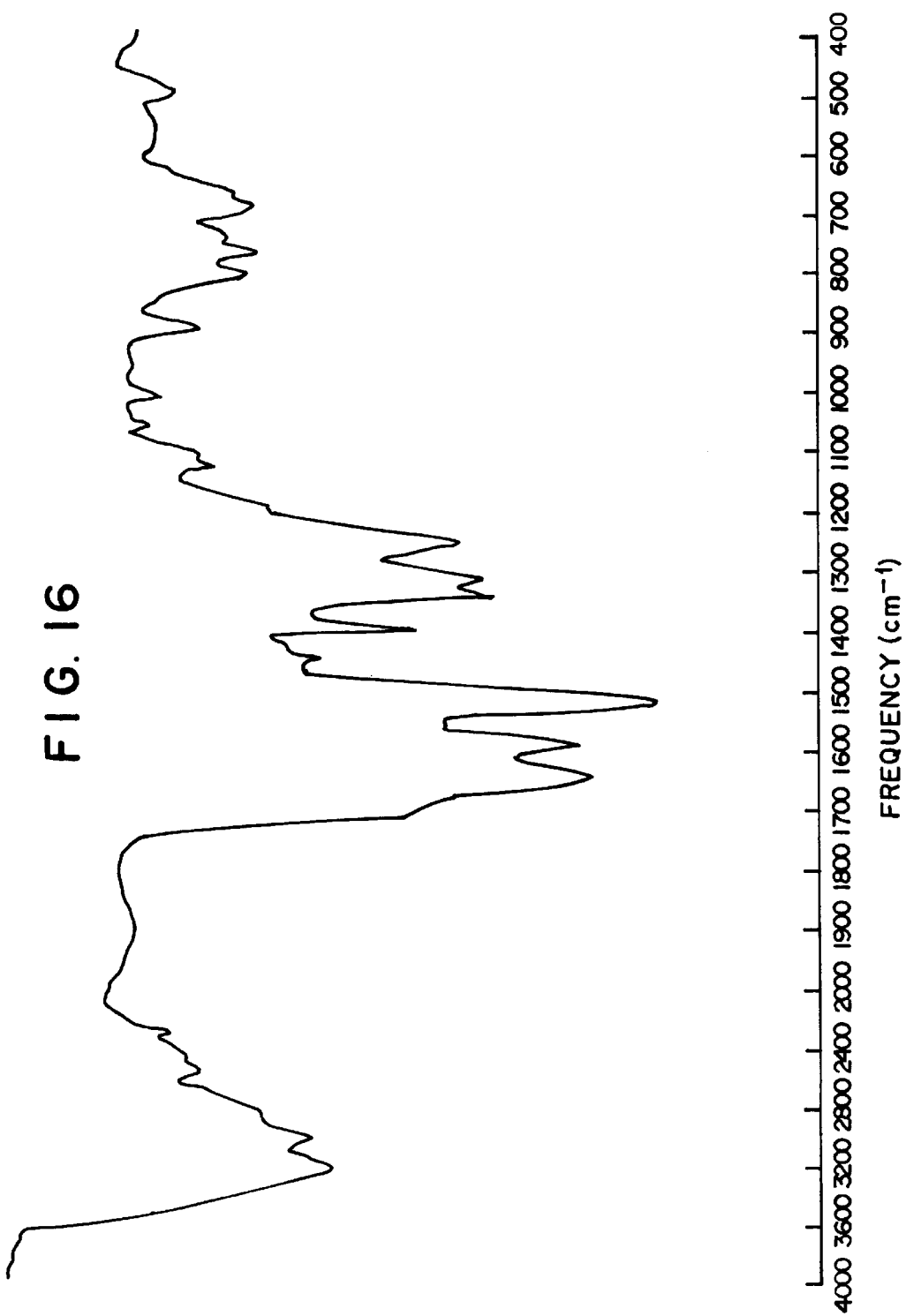
FIG. 16 is an IR spectrum of a compound No. 54 obtained in Preparation Example 18.

FIG. 16 is an infrared spectrum of the Compound No. 54.

Preparation Example 19
[Synthesis of Compound No. 55 shown in TABLE 1]

50 g of 3-nitrophthalic anhydride was dissolved in 100 ml of acetic anhydride. Part of 3-nitrophthalic anhydride remained insoluble and dispersed in the liquid. To this liquid, 24 g of 4,4'-diaminodiphenylether was added in about 20 portions over a period of about one hour. The resultant reaction mixture was stirred for 3 hours.

When the reaction mixture was poured into 1,000 ml of water, light yellow crystals separated out. The light yellow crystals were then collected by filtration and washed with water.

The light yellow crystals thus obtained were dispersed in 500 ml of water again. A 10% aqueous solution of sodium hydroxide was added dropwise to the thus obtained dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH2 to 3, whereby light yellow crystals separated out. The light yellow crystals thus obtained were washed with water and dried under reduced pressure, so that the Compound No. 55 was obtained as light yellow crystals in a yield of 25 g.

The melting point of this compound was 165 to 168° C. According to the analysis by thin-layer chromatography (TLC), the $R_f$ value of this compound was 0.28.

Figure 17:
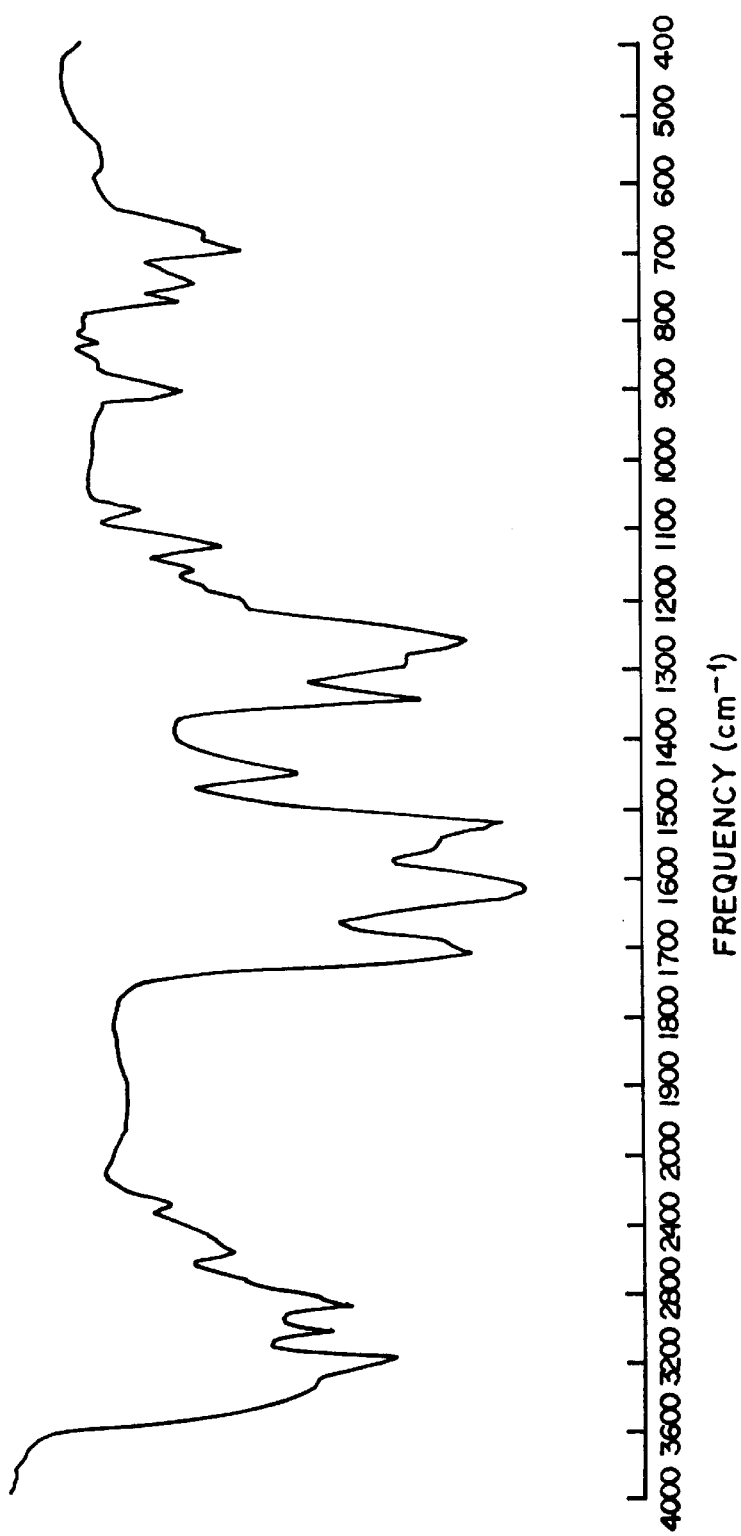
FIG. 17 is an IR spectrum of a compound No. 55 obtained in Preparation Example 19.

FIG. 17 is an infrared spectrum of the Compound No. 55.

Preparation Example 20

[Synthesis of Compound No. 56 shown in TABLE 1]

50 g of 3-nitrophthalic anhydride was dissolved in 100 ml of acetic anhydride. Part of 3-nitrophthalic anhydride remained insoluble and dispersed in the liquid. To this liquid, 30 g of 4,4'-diaminodiphenylsulfone was added in about 20 portions over a period of about one hour. The resultant reaction mixture was stirred for 3 hours.

When the reaction mixture was poured into 1,000 ml of water, white crystals separated out. The white crystals were then collected by filtration and washed with water.

The white crystals thus obtained were dispersed in 500 ml of water again. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that a mixture of the Compound No. 56 and the Compound No. 28 was obtained as white crystals in a yield of 40 g.

Thereafter, the mixture of the Compounds Nos. 56 and 28 was extracted with 500 ml each of a 30% aqueous solution of ethyl alcohol (with a ratio by weight of water to ethyl alcohol of 70:30) for ten times. The resultant extracted layer was concentrated, thereby obtaining white crystals.

These white crystals were dispersed in 200 ml of water. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that the Compound No. 56 was obtained as white crystals in a yield of 12 g.

The melting point of this compound was 172 to 176° C. According to the analysis by thin-layer chromatography (TLC), the $R_f$ value of this compound was 0.33.

Figure 18:
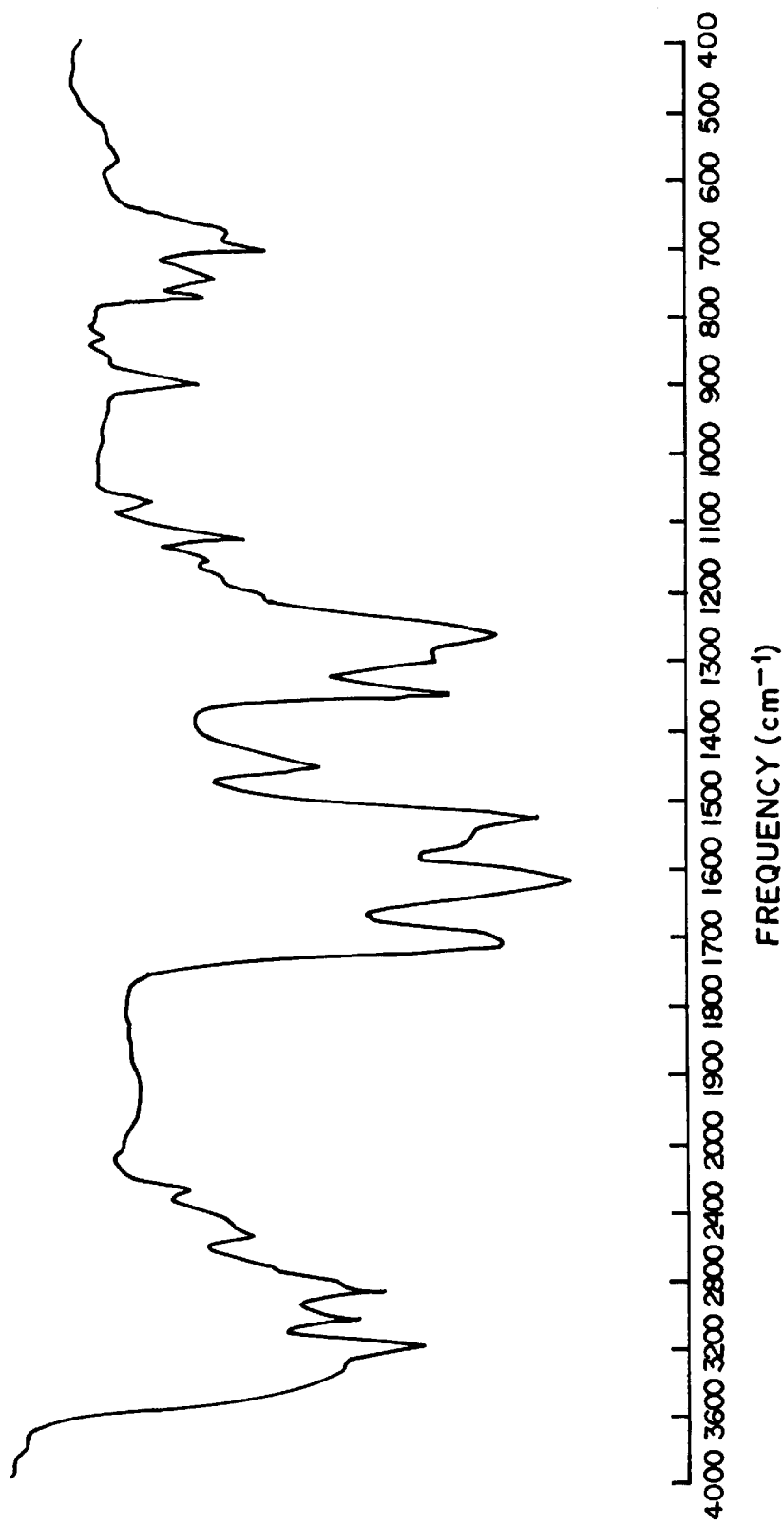
FIG. 18 is an IR spectrum of a compound No. 56 obtained in Preparation Example 20.

FIG. 18 is an infrared spectrum of the Compound No. 56.

Preparation Example 21

[Synthesis of Compound No. 51 shown in TABLE 1]

50 g of 3-nitrophthalic anhydride was dissolved in 100 ml of acetic anhydride. Part of 3-nitrophthalic anhydride remained insoluble and dispersed in the liquid. To this liquid, 30 g of 3,3'-diaminodiphenylsulfone was added in about 20 portions over a period of about one hour. The resultant reaction mixture was stirred for 3 hours.

When the reaction mixture was poured into 1,000 ml of water, white crystals separated out. The white crystals were then collected by filtration and washed with water.

The white crystals thus obtained were dispersed in 500 ml of water again. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that a mixture of the Compound No. 51 and the Compound No. 23 was obtained as white crystals in a yield of 30 g.

Thereafter, the mixture of the Compounds Nos. 51 and 23 was extracted with 500 ml each of a 30% aqueous solution of ethyl alcohol (with a ratio by weight of water to ethyl alcohol of 70:30) for ten times. The resultant extracted layer was concentrated, thereby obtaining white crystals.

These white crystals were dispersed in 200 ml of water. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that the Compound No. 51 was obtained as white crystals in a yield of 12 g.

The melting point of this compound was 164 to 168° C. According to the analysis by thin-layer chromatography (TLC), the $R_f$ value of this compound was 0.37.

Figure 19:
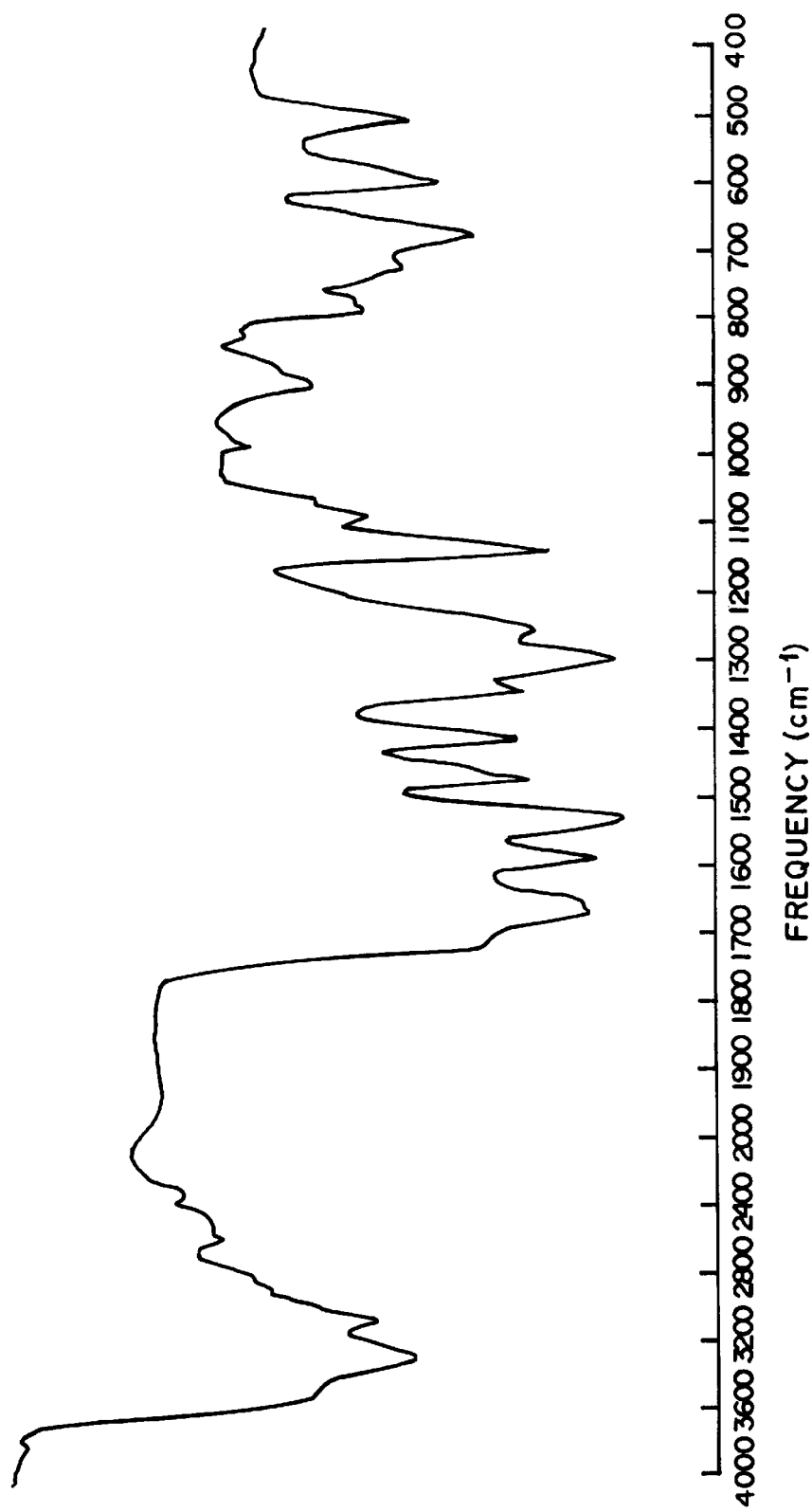
FIG. 19 is an IR spectrum of a compound No. 51 obtained in Preparation Example 21.

FIG. 19 is an infrared spectrum of the Compound No. 51.

Preparation Example 22

(Separation of Compound No. 56 from Compound No. 28)

0.2 g of the mixture of the Compound No. 56 and the Compound No. 28 obtained in the course of Preparation Example 20 was subjected to extracting operation at room temperature for 3 hours using 10 ml of a solvent selected from the following solvents:

(1) 20% aqueous solution of ethyl alcohol (2) 30% aqueous solution of ethyl alcohol (3) 40% aqueous solution of ethyl alcohol (4) 50% aqueous solution of ethyl alcohol In any case, the content of the Compound No. 56 in the extracted layer was examined by thin-layer chromatography (TLC). As a result, it was confirmed that the Compound No. 56 was efficiently extracted when the above-mentioned solvents (1), (2) and (3) were employed.

Preparation Example 23

(Separation of Compound No. 51 from Compound No. 23)

0.2 g of the mixture of the Compound No. 51 and the Compound No. 23 obtained in the course of Preparation Example 21 was subjected to extracting operation at room temperature for 3 hours using 10 ml of a solvent selected from the following solvents:

(1) 20% aqueous solution of ethyl alcohol (2) 30% aqueous solution of ethyl alcohol (3) 40% aqueous solution of ethyl alcohol (4) 50% aqueous solution of ethyl alcohol In any case, the content of the Compound No. 51 in the extracted layer was examined by thin-layer chromatography (TLC). As a result, it was confirmed that the Compound No. 51 was efficiently extracted when the above-mentioned solvents (1), (2) and (3) were employed.

Preparation Example 24
[Synthesis of Compound No. 56 shown in TABLE 1]

2.5 g of 3-nitrophthalic anhydride was dissolved in 10 ml of acetone. To the above prepared solution of 3-nitrophthalic anhydride, a solution prepared by dissolving 1.5 g of 4,4'-diaminodiphenylsulfone in 10 ml of acetone was added dropwise over a period of about 30 minutes.

After the resultant reaction mixture was stirred at room temperature for 3 hours, the solvent component was removed from the reaction mixture, thereby obtaining a yellow-brown solid.

The yellow-brown solid material was dispersed in 100 ml of water, and a 10% aqueous solution of sodium hydroxide was added dropwise to the thus obtained dispersion to adjust the dispersion to pH10 to 11, so that the yellow-brown solid was dissolved therein.

The thus obtained solution was subjected to filtration, and a 10% aqueous solution of hydrochloric acid was added dropwise to the resultant filtrate to adjust the filtrate to pH2 to 3, whereby light yellow crystals separated out. The light yellow crystals thus obtained were washed with water and dried under reduced pressure, so that 1.5 g of light yellow crystals was obtained.

The melting point of the thus obtained crystals was 160 to 165° C. According to the analysis by thin-layer chromatography (TLC), two spots were observed. From the $R_f$ values and the sizes of the spots, it was confirmed that the Compound No. 56 and the Compound No. 28 were contained in substantially the same amounts.

Preparation Example 25
[Synthesis of Compound No. 56 shown in TABLE 1]

10 g of 3-nitrophthalic anhydride was dissolved in 30 ml of methyl ethyl ketone. To the above prepared solution of 3-nitrophthalic anhydride, a solution prepared by dissolving 6.4 g of 4,4'-diaminodiphenylsulfone in 30 ml of methyl ethyl ketone was added dropwise over a period of about 30 minutes.

After the resultant reaction mixture was stirred at room temperature for 3 hours, the solvent component was removed from the reaction mixture, thereby obtaining a yellow-brown solid.

The yellow-brown solid material was dispersed in 100 ml of water, and a 10% aqueous solution of sodium hydroxide was added dropwise to the thus obtained dispersion to adjust the dispersion to pH10 to 11, so that the yellow-brown solid was dissolved therein.

The thus obtained solution was subjected to filtration, and a 10% aqueous solution of hydrochloric acid was added dropwise to the resultant filtrate to adjust the filtrate to pH2 to 3, whereby light yellow crystals separated out. The light yellow crystals thus obtained were washed with water and dried under reduced pressure, so that 1.3 g of light yellow crystals was obtained.

The melting point of the thus obtained crystals was 168 to 179° C. According to the analysis by thin-layer chromatography (TLC), two spots were observed. From the $R_f$ values and the sizes of the spots, it was confirmed that the Compound No. 56 and the Compound No. 28 were contained in substantially the same amounts.

Preparation Example 26
[Synthesis of Compound No. 54 shown in TABLE 1]

A mixture of 20 g of 3-nitrophthalic acid and 20 ml of acetic anhydride was dispersed and stirred under the application of heat thereto. The mixture was heated until 3-nitrophthalic acid was dissolved in acetic anhydride. Then, the reaction mixture was allowed to stand at room temperature, whereby 3-nitrophthalic anhydride separated out.

To the above reaction mixture, 9.0 g of 4,4'-diaminodiphenylmethane was added, and the mixture was stirred at room temperature for 5 hours. After the completion of stirring, the reaction mixture was poured into 1,000 ml of water with stirring at room temperature for 8 hours, so that light yellow crystals separated out.

The thus obtained crystals were collected by filtration and washed with water, and then, dispersed in 200 ml of water again. A 10% aqueous solution of sodium hydroxide was added dropwise to the above prepared dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH2 to 3, whereby light yellow crystals separated out. The light yellow crystals thus obtained were washed with water and dried under reduced pressure, so that 2.0 g of light yellow crystals was obtained.

The melting point of the thus obtained crystals was 154 to 160° C. According to the analysis by thin-layer chromatography (TLC), two spots were observed. From the $R_f$ values and the sizes of the spots, it was confirmed that the Compound No. 54 and the Compound No. 16 were contained in substantially the same amounts.

Preparation Example 27
[Synthesis of Compound No. 56 shown in TABLE 1]

A mixture of 20 g of 3-nitrophthalic acid and 20 ml of acetic anhydride was dispersed and stirred under the application of heat thereto. The mixture was heated until 3-nitrophthalic acid was dissolved in acetic anhydride. Then, the reaction mixture was allowed to stand at room temperature, whereby 3-nitrophthalic anhydride separated out.

To the above reaction mixture, 11.7 g of 4,4'-diaminodiphenylsulfone was added, and the mixture was stirred at room temperature for 5 hours. After the completion of stirring, the reaction mixture was poured into 1,000 ml of water with stirring at room temperature for 8 hours, so that white crystals separated out.

The thus obtained crystals were collected by filtration and washed with water, and then, dispersed in 200 ml of water again. A 10% aqueous solution of sodium hydroxide was added dropwise to the thus obtained dispersion to adjust the dispersion to pH10 to 11, so that the white crystals were dissolved therein.

The thus obtained solution was subjected to filtration, and a 10% aqueous solution of hydrochloric acid was added dropwise to the resultant filtrate to adjust the filtrate to pH2 to 3, whereby white crystals separated out. The white crystals thus obtained were washed with water and dried under reduced pressure, so that 15 g of white crystals was obtained.

The melting point of the thus obtained crystals was 162 to 165° C. According to the analysis by thin-layer chromatography (TLC), two spots were observed. From the $R_f$ values and the sizes of the spots, it was confirmed that the Compound No. 56 and the Compound No. 28 were contained in substantially the same amounts.

Preparation Example 28
[Synthesis of Compound No. 26 shown in TABLE 1]

4.9 g of 4,4'-diaminodiphenylmethane was dissolved in 200 ml of toluene to prepare a solution, and 7.5 g of pyridine was further added to the solution. To the above prepared mixture, a solution prepared by dissolving 13.4 g of 3-nitro-2-methoxycarbonylbenzoyl chloride in 80 ml of toluene was added dropwise at room temperature.

After completion of the addition, the reaction mixture was stirred for 4 hours. Thereafter, the toluene was distilled away from the reaction mixture under reduced pressure, thereby obtaining a yellow liquid.

The yellow liquid thus obtained was poured into 800 ml of ice-cold water with stirring, so that 9.0 g of light yellow crystals was obtained.

9.0 g of the light yellow crystals was dispersed in a solution prepared by dissolving 2 g of potassium hydroxide in 100 ml of water, and the dispersion was refluxed for 10 hours. After cooled to room temperature, the dispersion was adjusted to pH2 with dilute hydrochloric acid, whereby the Compound No. 26 was obtained as pale pink crystals in a yield of 3.0 g.

The melting point of this compound was 170 to 175° C.

Preparation Example 29
[Synthesis of Compound No. 27 shown in TABLE 1]

10.0 g of 4,4'-diaminodiphenylmethane was dissolved in 100 ml of dimethylformamide to prepare a solution, and 13.0 g of pyridine was further added to the solution. To the above prepared mixture, a solution prepared by dissolving 26.2 g of 3-nitro-2-methoxycarbonylbenzoyl chloride in 100 ml of dimethylformamide was added dropwise at room temperature.

After completion of the addition, the reaction mixture was stirred for 4 hours. Thereafter, the dimethylformamide was distilled away from the reaction mixture under reduced pressure, and the reaction mixture was poured into 800 ml of water, thereby obtaining 14.3 g of an orange solid.

14.0 g of the orange solid material thus obtained was dispersed in a solution prepared by dissolving 5 g of potassium hydroxide in 200 ml of water, and the dispersion was refluxed for 10 hours. After cooled to room temperature, the dispersion was adjusted to pH2 with dilute hydrochloric acid, whereby the Compound No. 27 was obtained as light yellow crystals in a yield of 5.0 g.

The melting point of this compound was 175 to 178° C.

Preparation Example 30
[Synthesis of Compound No. 28 shown in TABLE 1]

10.0 g of 4,4'-diaminodiphenylmethane was dissolved in 200 ml of methyl ethyl ketone to prepare a solution, and 8.6 g of pyridine was further added to the solution. To the above prepared mixture, a solution prepared by dissolving 22.0 g of 3-nitro-2-methoxycarbonylbenzoyl chloride in 100 ml of methyl ethyl ketone was added dropwise at room temperature.

After completion of the addition, the reaction mixture was stirred for 4 hours. Thereafter, the methyl ethyl ketone was distilled away from the reaction mixture under reduced pressure, and the reaction mixture was poured into 800 ml of water, thereby obtaining 25.0 g of an orange viscous material.

25.0 g of the orange viscous material thus obtained was dispersed in a solution prepared by dissolving 4.5 g of potassium hydroxide in 300 ml of water, and the dispersion was refluxed for 10 hours. After cooled to room temperature, the dispersion was adjusted to pH2 with dilute hydrochloric acid, whereby the Compound No. 28 was obtained as light yellow crystals in a yield of 11.6 g.

The melting point of this compound was 191 to 194° C.

Preparation Example 31
[Synthesis of Compound No. 50 shown in TABLE 1]

2.9 g of 1,6-hexamethylenediamine was dissolved in 50 ml of toluene to prepare a solution, and 7.5 g of pyridine was further added to the solution. To the above prepared mixture, a solution prepared by dissolving 13.4 g of 2-nitro-6-methoxycarbonylbenzoyl chloride in 50 ml of toluene was added dropwise at room temperature.

After completion of the addition, the reaction mixture was stirred for 4 hours. Thereafter, the toluene was distilled away from the reaction mixture under reduced pressure, and the reaction mixture was poured into 800 ml of water, thereby obtaining 9.1 g of yellow-white crystals.

9.1 g of the yellow-white crystals thus obtained were dispersed in a solution prepared by dissolving 3.8 g of potassium hydroxide in 150 ml of water, and the dispersion was refluxed for 10 hours. After cooled to room temperature, the dispersion was adjusted to pH2 with dilute hydrochloric acid, whereby the Compound No. 50 was obtained as white crystals in a yield of 1.6 g.

The melting point of this compound was 145 to 148° C.

Preparation Example 32
[Synthesis of Compound No. 54 shown in TABLE 1]

2.7 g of 4,4'-diaminodiphenylmethane was dissolved in 200 ml of toluene to prepare a solution, and 10.0 g of pyridine was further added to the solution. To the above prepared mixture, a solution prepared by dissolving 10.0 g of 2-nitro-6-methoxycarbonylbenzoyl chloride in 80 ml of toluene was added dropwise at room temperature.

After completion of the addition, the reaction mixture was stirred for 4 hours. Thereafter, the toluene was distilled away from the reaction mixture under reduced pressure, so that a yellow liquid was obtained.

The yellow liquid thus obtained was poured into 800 ml of ice-cold water with stirring, thereby obtaining 8.0 g of pale yellow crystals.

8.0 g of the pale yellow crystals was dispersed in a solution prepared by dissolving 10 g of potassium hydroxide in 300 ml of water, and the dispersion was refluxed for 10 hours. After cooled to room temperature, the dispersion was adjusted to pH2 with dilute hydrochloric acid, whereby the Compound No. 54 was obtained as light yellow crystals in a yield of 3.0 g.

The melting point of this compound was 170 to 174° C.

Preparation Example 33
[Synthesis of Compound No. 55 shown in TABLE 1]

10.0 g of 4,4'-diaminodiphenylether was dissolved in 200 ml of dimethylformamide to prepare a solution, and 13.0 g of pyridine was further added to the solution. To the above prepared mixture, a solution prepared by dissolving 26.2 g of 2-nitro-6-methoxycarbonylbenzoyl chloride in 100 ml of dimethylformamide was added dropwise at room temperature.

After completion of the addition, the reaction mixture was stirred for 4 hours. Thereafter, the dimethylformamide was distilled away from the reaction mixture under reduced pressure, and the reaction mixture was poured into 800 ml of water, thereby obtaining 19.3 g of a yellow solid.

19.3 g of the yellow solid material thus obtained was dispersed in a solution prepared by dissolving 5 g of potassium hydroxide in 200 ml of water, and the dispersion was refluxed for 10 hours. After cooled to room temperature, the dispersion was adjusted to pH2 with dilute hydrochloric acid, whereby the Compound No. 55 was obtained as pale pink crystals in a yield of 5.0 g.

The melting point of this compound was 162 to 165° C.

Preparation Example 34
[Synthesis of Compound No. 56 shown in TABLE 1]

10.0 g of 4,4'-diaminodiphenylsulfone was dissolved in 200 ml of methyl ethyl ketone to prepare a solution, and 13.0 g of pyridine was further added to the solution. To the above prepared mixture, a solution prepared by dissolving 20.0 g of 2-nitro-6-methoxycarbonylbenzoyl chloride in 100 ml of methyl ethyl ketone was added dropwise at room temperature.

After completion of the addition, the reaction mixture was stirred for 4 hours. Thereafter, the methyl ethyl ketone was distilled away from the reaction mixture under reduced pressure, and the reaction mixture was poured into 800 ml of water, thereby obtaining 15.0 g of an orange viscous material.

15.0 g of the orange viscous material thus obtained was dispersed in a solution prepared by dissolving 3.0 g of potassium hydroxide in 300 ml of water, and the dispersion was refluxed for 10 hours. After cooled to room temperature, the dispersion was adjusted to pH2 with dilute hydrochloric acid, whereby the Compound No. 56 was obtained as pale pink crystals in a yield of 11.6 g.

The melting point of this compound was 175 to 179° C.

Preparation Example 35
[Synthesis of Compound No. 123 shown in TABLE 1]

40 g of trimellitic anhydride was dispersed in 250 ml of acetic acid to prepare a dispersion of trimellitic anhydride. To this dispersion, 25.0 g of 4,4'-diaminodiphenylsulfone was added for three times. The resultant reaction mixture was stirred at room temperature for 3 hours.

After the reaction mixture was poured into 1,000 ml of water and stirred at room temperature, white crystals separated out. The white crystals were then collected by filtration and washed with water.

The white crystals thus obtained were dispersed in 1,000 ml of water again. A 10% aqueous solution of sodium hydroxide was added dropwise to the thus obtained dispersion so as to dissolve the white crystals therein.

The thus obtained solution was subjected to filtration, and a 10% aqueous solution of hydrochloric acid was added dropwise to the resultant filtrate, whereby white crystals separated out. The white crystals thus obtained were washed with water and dried under reduced pressure, so that 53.0 g of an intermediate No. 1 represented by the following formula was obtained.

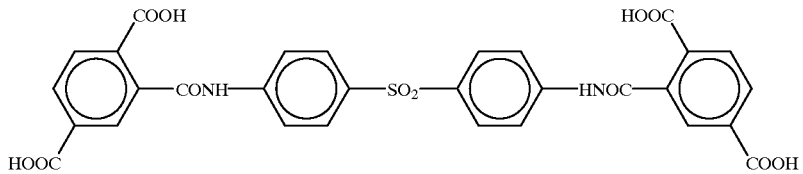

The melting point of this intermediate No. 1 was 231 to 235° C. According to the analysis by thin-layer chromatography (TLC), the $R_f$ value of this compound was 0.06.

7.0 g of the above obtained intermediate was dissolved in 30 ml of dimethyl sulfoxide to prepare a solution. To this solution, 2.4 g of sodium carbonate was added with stirring, whereby a dispersion was obtained. To this dispersion, a solution prepared by dissolving 3.5 g of ethyl bromide in 10 ml of dimethyl sulfoxide was added dropwise at room temperature. The thus obtained reaction mixture was heated on a water bath of 80° C. with stirring for 12 hours, with 1.0 g of ethyl bromide being further added in two portions to the reaction mixture.

The resultant reaction mixture was poured into 400 ml of water, and a 10% aqueous solution of hydrochloric acid was added dropwise to the mixture, whereby white crystals separated out. The white crystals were washed with water and dried under reduced pressure, so that the Compound No. 123 was obtained as white crystals in a yield of 4.5 g.

The melting point of this compound was 143 to 148° C. According to the analysis by thin-layer chromatography (TLC), the $R_f$ value of this compound was 0.10.

Preparation Example 36
[Synthesis of Compound No. 131 shown in TABLE 1]

The intermediate No. 1 was synthesized in the same manner as described in Preparation Example 35.

7.0 g of the above obtained intermediate No. 1 was dissolved in 30 ml of dimethyl sulfoxide to prepare a solution. To this solution, 2.4 g of sodium carbonate was added with stirring, whereby a dispersion was obtained. To this dispersion, a solution prepared by dissolving 3.8 g of benzyl bromide in 10 ml of dimethyl sulfoxide was added dropwise at room temperature. The thus obtained reaction mixture was heated on a water bath of 90 to 95° C. with stirring for 12 hours.

The resultant reaction mixture was poured into 400 ml of water, and a 10% aqueous solution of hydrochloric acid was added dropwise to the mixture, whereby white crystals separated out. The white crystals were washed with water and dried under reduced pressure, so that the Compound No. 131 was obtained as white crystals in a yield of 4.1 g.

The melting point of this compound was 144 to 147° C. According to the analysis by thin-layer chromatography (TLC), the $R_f$ value of this compound was 0.15.

Preparation Example 37
[Synthesis of Compound No. 395 shown in TABLE 1]

23.0 g of 4-hydroxyphthalic anhydride was dissolved in 100 ml of acetic acid to prepare a solution. To this solution, 13.5 g of 4,4'-diaminodiphenylmethane was added in small portions. The thus obtained reaction mixture was stirred for 2 hours.

The resultant reaction mixture was poured into 1,000 ml of water, so that light yellow crystals separated out. The crystals were collected by filtration and washed with water.

The light yellow crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby white crystals separated out. The white crystals were washed with water and dried under reduced pressure, so that the Compound No. 395 was obtained as white crystals in a yield of 29.0 g.

The melting point of this compound was 167 to 171° C. According to the analysis by thin-layer chromatography (TLC), the $R_f$ value of this compound was 0.28.

Preparation Example 38
[Synthesis of Compound No. 407 shown in TABLE 1]

7.0 g of 4-hydroxyphthalic anhydride was dissolved in 50 ml of acetic acid to prepare a solution. To this solution, 5.0 g of 4,4'-diaminodiphenylsulfone was added in a small portions. The thus obtained reaction mixture was stirred for 2 hours.

The resultant reaction mixture was poured into 500 ml of water, so that white crystals separated out. The crystals were collected by filtration and washed with water.

The white crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby white crystals separated out. The white crystals were washed with water and dried under reduced pressure, so that the Compound No. 407 was obtained as white crystals in a yield of 9.5 g.

The melting point of this compound was 183 to 187° C. According to the analysis by thin-layer chromatography (TLC), the $R_f$ value of this compound was 0.11.

Preparation Example 39
[Synthesis of Compound No. 413 shown in TABLE 1]

7.0 g of 4-hydroxyphthalic anhydride was dissolved in 50 ml of acetic acid to prepare a solution. To this solution, 5.0 g of 3,3'-diaminodiphenylsulfone was added in small portions. The thus obtained reaction mixture was stirred for 2 hours.

The resultant reaction mixture was poured into 500 ml of water, so that white crystals separated out. The crystals were collected by filtration and washed with water.

The white crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby white crystals separated out. The white crystals were washed with water and dried under reduced pressure, so that the Compound No. 413 was obtained as white crystals in a yield of 8.6 g.

The melting point of this compound was 185 to 190° C. According to the analysis by thin-layer chromatography (TLC), the $R_f$ value of this compound was 0.11.

Preparation Example 40
[Synthesis of Compound No. 400 shown in TABLE 1]

7.0 g of the Compound No. 43 was dissolved in 30 ml of pyridine to prepare a solution. To this solution, 9.0 g of p-toluenesulfonic acid chloride was added in small portions, with special care being exercised to prevent the sudden increase of the temperature of the reaction system. The thus obtained reaction mixture was heated for one hour so as to maintain the temperature of the reaction system at 45° C., and thereafter poured into 200 ml of ice-cold water, so that milky white crystals separated out. The crystals were collected by filtration and washed with water.

The milky white crystals were dispersed in 200 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby pale pink crystals separated out. The pale pink crystals were washed with water and dried under reduced pressure, so that the Compound No. 400 was obtained as pale pink crystals in a yield of 4.7 g.

The melting point of this compound was 144 to 150° C. According to the analysis by thin-layer chromatography (TLC), the $R_f$ value of this compound was 0.06.

Preparation Example 41
[Synthesis of Compound No. 396 shown in TABLE 1]

17.0 g of 4-(2-phenoxyethyleneoxy)phthalic anhydride was dissolved in 100 ml of acetic acid to prepare a solution. To this solution, 5.5 g of 4,4'-diaminodiphenylmethane was added in small portions. The thus obtained reaction mixture was stirred for 5 hours, and thereafter poured into 1,000 ml of water, so that pale brown crystals separated out. The crystals were collected by filtration and washed with water.

The pale brown crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby white crystals separated out. The white crystals were washed with water and dried under reduced pressure, so that the Compound No. 396 was obtained as white crystals in a yield of 18.1 g.

The melting point of this compound was 128 to 131° C. According to the analysis by thin-layer chromatography (TLC), the $R_f$ value of this compound was 0.20.

Preparation Example 42
[Synthesis of Compound No. 668 shown in TABLE 1]

16.0 g of phthalic anhydride was dissolved in 100 ml of acetic acid to prepare a solution. To this solution, 15.0 g of 2,2-bis(4-aminophenoxy)propylidene was added in small portions. The thus obtained reaction mixture was stirred for 2 hours, and thereafter poured into 700 ml of water, so that gray-white crystals separated out. The crystals were collected by filtration and washed with water.

The gray-white crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby white crystals separated out. The white crystals were washed with water and dried under reduced pressure, so that the Compound No. 668 was obtained as white crystals in a yield of 22.7 g.

The melting point of this compound was 155 to 158° C. According to the analysis by thin-layer chromatography (TLC), the $R_f$ value of this compound was 0.20.

Preparation Example 43
[Synthesis of Compound No. 663 shown in TABLE 1]

10.5 g of phthalic anhydride was dissolved in 100 ml of acetic acid to prepare a solution. To this solution, 15.0 g of bis(4-aminophenoxyphenyl)sulfone was added in small portions. The thus obtained reaction mixture was stirred for 2 hours, and thereafter poured into 700 ml of water, so that gray-white crystals separated out. The crystals were collected by filtration and washed with water.

The gray-white crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby white crystals separated

Preparation Example 44
[Synthesis of Compound No. 673 shown in TABLE 1]

11.5 g of phthalic anhydride was dissolved in 100 ml of acetic acid to prepare a solution. To this solution, 15.0 g of 2,2-bis(4-aminophenoxyphenyl)propylidene was added in small portions. The thus obtained reaction mixture was stirred for 2 hours, and thereafter poured into 700 ml of water, so that white crystals separated out. The crystals were collected by filtration and washed with water.

The white crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby white crystals separated out. The white crystals were washed with water and dried under reduced pressure, so that the Compound No. 673 was obtained as white crystals in a yield of 21.7 g.

The melting point of this compound was 141 to 148° C. According to the analysis by thin-layer chromatography (TLC), the $R_f$ value of this compound was 0.20.

Preparation Example 45
[Synthesis of Compound No. 671 shown in TABLE 1]

20.0 g of phthalic anhydride was dissolved in 100 ml of acetic acid to prepare a solution. To this solution, 16.0 g of bis(4-amino-2-ethylphenyl)methane was added in small portions. The thus obtained reaction mixture was stirred for 2 hours, and thereafter poured into 700 ml of water, so that light yellow crystals separated out. The crystals were collected by filtration and washed with water.

The light yellow crystals were dispersed in 500 ml of water again and a 10% aqueous solution of sodium hydroxide was added dropwise to the dispersion so as to dissolve the crystals therein.

The thus obtained solution was subjected to filtration, and a 10% aqueous solution of hydrochloric acid was added dropwise to the filtrate, whereby light yellow crystals separated out. The light yellow crystals were washed with water and dried under reduced pressure, so that the Compound No. 671 was obtained as light yellow crystals in a yield of 27.9 g.

The melting point of this compound was 144 to 147° C. According to the analysis by thin-layer chromatography (TLC), the $R_f$ value of this compound was 0.15.

Preparation Example 46
[Synthesis of Compound No. 532 shown in TABLE 1]

7.0 g of phthalic anhydride and 9.1 g of 4-nitrophthalic anhydride were dissolved in 100 ml of acetic acid. Part of anhydrides remained insoluble and dispersed in the liquid. To this liquid, 11.0 g of 4,4'-diaminodiphenylsulfone was added in small portions. The resultant reaction mixture was stirred for 2 hours.

When the reaction mixture was poured into 1,000 ml of water, light yellow crystals separated out. The crystals were then collected by filtration and washed with water.

The light yellow crystals thus obtained were dispersed in 500 ml of water again. A 10% aqueous solution of sodium hydroxide was added dropwise to the thus obtained dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH3 to 4, whereby light yellow crystals separated out. The light yellow crystals thus obtained were washed with water and dried under reduced pressure, so that the Compound No. 532 was obtained as light yellow crystals in a yield of 21.2 g.

The melting point of this compound was 168 to 172° C. According to the analysis by thin-layer chromatography (TLC), the $R_f$ value of this compound was 0.30.

Preparation Example 47
[Synthesis of Compound No. 523 shown in TABLE 1]

10.0 g of 4-hydroxyphthalic anhydride and 12.0 g of 4-nitrophthalic anhydride were dissolved in 100 ml of acetic acid. Part of anhydrides remained insoluble and dispersed in the liquid. To this liquid, 11.9 g of 4,4'-diaminodiphenylmethane was added in small portions. The resultant reaction mixture was stirred for 2 hours.

When the reaction mixture was poured into 500 ml of water, light yellow crystals separated out. The crystals were then collected by filtration and washed with water.

The light yellow crystals thus obtained were dispersed in 500 ml of water again. A 10% aqueous solution of sodium hydroxide was added dropwise to the thus obtained dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH3 to 4, whereby light yellow crystals separated out. The light yellow crystals thus obtained were washed with water and dried under reduced pressure, so that the Compound No. 523 was obtained as light yellow crystals in a yield of 20.7 g.

The melting point of this compound was 160 to 164° C. According to the analysis by thin-layer chromatography (TLC), the $R_f$ value of this compound was 0.20.

Preparation Example 48
[Synthesis of Compound No. 522 shown in TABLE 1]

7.0 g of phthalic acid and 9.1 g of 4-nitrophthalic anhydride were dissolved in 100 ml of acetic acid. Part of anhydrides remained insoluble and dispersed in the liquid. To this liquid, 9.0 g of 4,4'-diaminodiphenylmethane was added in small portions. The resultant reaction mixture was stirred for 4 hours.

When the reaction mixture was poured into 500 ml of water, light yellow crystals separated out. The crystals were then collected by filtration and washed with water.

The light yellow crystals thus obtained were dispersed in 500 ml of water again. A 10% aqueous solution of sodium hydroxide was added dropwise to the thus obtained dispersion to adjust the dispersion to pH10 to 11, so that the light yellow crystals were dissolved therein.

The thus obtained solution was subjected to filtration, and a 10% aqueous solution of hydrochloric acid was added dropwise to the resultant filtrate to adjust the filtrate to pH3 to 4, whereby light yellow crystals separated out. The light yellow crystals thus obtained were washed with water and dried under reduced pressure, so that the Compound No. 522 was obtained as light yellow crystals in a yield of 18.8 g.

The melting point of this compound was 154 to 156° C. According to the analysis by thin-layer chromatography (TLC), the $R_f$ value of this compound was 0.20.

Preparation Example 49

[Synthesis of Compound No. 521 shown in TABLE 1]

9.0 g of phthalic anhydride and 10.0 g of 4-hydroxyphthalic anhydride were dissolved in 150 ml of acetic acid. Part of anhydrides remained insoluble and dispersed in the liquid. To this liquid, 11.0 g of 4,4'-diaminodiphenylmethane was added in small portions. The resultant reaction mixture was stirred for 2 hours.

When the reaction mixture was poured into 500 ml of water, light brown crystals separated out. The crystals were then collected by filtration and washed with water.

The light brown crystals thus obtained were dispersed in 350 ml of water again. A 10% aqueous solution of sodium hydroxide was added dropwise to the thus obtained dispersion to adjust the dispersion to pH10 to 11, so that the light brown crystals were dissolved therein.

The thus obtained solution was subjected to filtration, and a 10% aqueous solution of hydrochloric acid was added dropwise to the resultant filtrate to adjust the filtrate to pH3 to 4, whereby light brown crystals separated out. The light brown crystals thus obtained were washed with water and dried under reduced pressure, so that the Compound No. 521 was obtained as light brown crystals in a yield of 19.7 g.

The melting point of this compound was 150 to 155° C. According to the analysis by thin-layer chromatography (TLC), the $R_f$ value of this compound was 0.05.

Preparation Example 50

[Synthesis of Compound No. 528 shown in TABLE 1]

9.0 g of phthalic acid and 10.0 g of 4-hydroxyphthalic anhydride were dissolved in 150 ml of acetic acid. Part of anhydrides remained insoluble and dispersed in the liquid. To this liquid, 13.0 g of 4,4'-diaminodiphenylsulfone was added in small portions. The resultant reaction mixture was stirred for 2 hours.

When the reaction mixture was poured into 600 ml of water, light brown crystals separated out. The crystals were then collected by filtration and washed with water.

The light brown crystals thus obtained were dispersed in 500 ml of water again. A 10% aqueous solution of sodium hydroxide was added dropwise to the thus obtained dispersion to adjust the dispersion to pH10 to 11, so that the light brown crystals were dissolved therein.

The thus obtained solution was subjected to filtration, and a 10% aqueous solution of hydrochloric acid was added dropwise to the resultant filtrate to adjust the filtrate to pH3 to 4, whereby light brown crystals separated out. The light brown crystals thus obtained were washed with water and dried under reduced pressure, so that the Compound No. 528 was obtained as light brown crystals in a yield of 25.0 g.

The melting point of this compound was 168 to 173° C. According to the analysis by thin-layer chromatography (TLC), the $R_f$ value of this compound was 0.05.

In the previously mentioned Preparation Examples, the melting point of the compound was measured using a commercially available micro melting point apparatus, made by Yanaco Co., Ltd. In addition, the TLC analysis was carried out using a commercially available chromato plate "KODAK Chromatogram Sheet 13181 Silica Gel (with fluorescent indicator)" (Trademark), and a mixed solvent of ethyl acetate and ethyl alcohol with a ratio by volume of 1:1 as a developing solution. After the developing solvent was dried, the chromato plate was exposed to ultraviolet light to detect the spot of the compound. The flow rate expressed by the $R_f$ value was obtained in accordance with the following formula:

$$R_f \text{ value} = \frac{\text{Developing distance of a spot of compound}}{\text{Developing distance of developing solution}}$$

The aromatic carboxylic acid compounds according to the present invention are novel and useful as the color developers for use in the thermosensitive recording material. When such an aromatic carboxylic acid compound is used as the color developer in the thermosensitive recording material, the preservation stability of recorded images, particularly in terms of plasticizer resistnace is remarkably improved.

In addition, the aforementioned aromatic carboxylic acid compound can be produced efficiently by the method of the present invention.

Japanese Patent Application No. 09-233381 filed Aug. 14, 1997, Japanese Patent Applications Nos. 09-323851 and 09-323852 filed Nov. 10, 1997, Japanese Patent Applications Nos. 09-335141 and 09-335142 filed Nov. 19, 1997, Japanese Patent Application No. 09-344162 filed Nov. 27, 1997, Japanese Patent Application No. 09-356211 filed Dec. 9, 1997, Japanese Patent Applications Nos. 09-364686 and 09-364687 filed Dec. 18, 1997, Japanese Patent Application No. 10-042936 filed Feb. 9, 1998, Japanese Patent Application No. 10-098156 filed Mar. 27, 1998 and Japanese Patent Application No. 10-153632 filed May 18, 1998 are hereby incorporated by reference.

What is claimed is:

1. A thermosensitive recording material comprising a support and a thermosensitive coloring layer formed thereon comprising a leuco dye and a color developer capable of inducing color formation in said leuco dye upon application of heat thereto, with said color developer comprising at least one compound (A) having in a molecule thereof at least two aromatic ring moieties selected from the group consisting of:

(i) an aromatic ring moiety having at least one carboxyl group and at least one electron-attracting functional group, (ii) an aromatic ring moiety having at least one carboxyl group and at least one electron-donating functional group, and (iii) an aromatic ring moiety having at least one carboxyl group, free of said electron-attracting functional group and said electron-donating functional group, at least two of said aromatic ring moieties in said compound (A) being bonded by either ester linkage or amide linkage, provided that from compounds having two of said aromatic ring moieties (iii) serving as said compound (A), a compound of formula (B) is excluded:

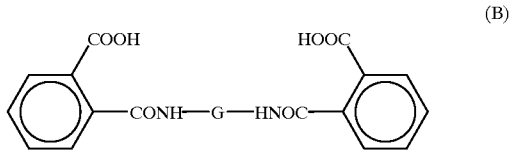

(B)

wherein G is —$C_nH_{2n-2}$— (in which n is an integer of 2 to 6),

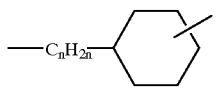

(in which n is an integer of 2 to 6),

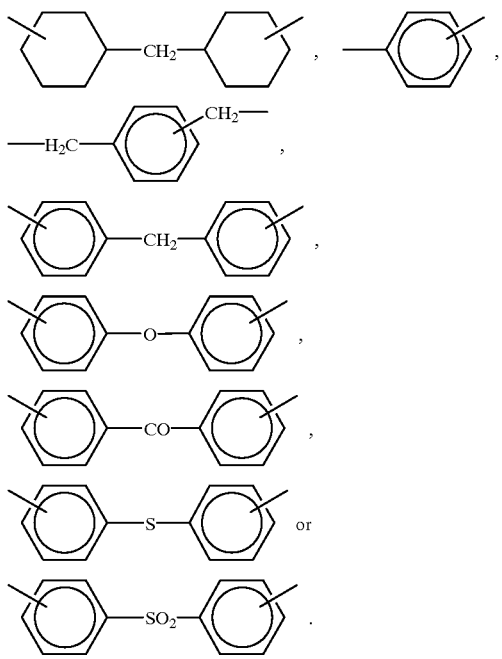

2. The thermosensitive recording material as claimed in claim 1, wherein at least two of said aromatic ring moieties for use in said compound (A) are bonded by ester linkage.

3. The thermosensitive recording material as claimed in claim 2, wherein said aromatic ring moieties in the molecule of said compound (A) are different.

4. The thermosensitive recording material as claimed in claim 2, wherein said electron-attracting functional group is selected from the group consisting of nitro group and ester group.

5. The thermosensitive recording material as claimed in claim 2, wherein said electron-donating functional group is selected from the group consisting of hydroxyl group, alkoxyl group and sulfonyloxy group.

6. The thermosensitive recording material as claimed in claim 1, wherein at least two of said aromatic ring moieties for use in said compound (A) are bonded by amide linkage.

7. The thermosensitive recording material as claimed in claim 6, wherein said aromatic ring moieties in the molecule of said compound (A) are different.

8. The thermosensitive recording material as claimed in claim 6, wherein said electron-attracting functional group is selected from the group consisting of nitro group and ester group.

9. The thermosensitive recording material as claimed in claim 6, wherein said electron-donating functional group is selected from the group consisting of hydroxyl group, alkoxyl group and sulfonyloxy group.

10. The thermosensitive recording material as claimed in claim 1, wherein said compound (A) has in the molecule thereof at least two aromatic ring moieties (i).

11. The thermosensitive recording material as claimed in claim 10, wherein at least two of said aromatic ring moieties (i) are bonded by ester linkage.

12. The thermosensitive recording material as claimed in claim 10, wherein at least two of said aromatic ring moieties (i) are bonded by amide linkage.

13. The thermosensitive recording material as claimed in claim 10, wherein said electron-attracting functional group is selected from the group consisting of nitro group and ester group.

14. The thermosensitive recording material as claimed in claim 1, wherein said compound (A) has in the molecule thereof at least two aromatic ring moieties (ii).

15. The thermosensitive recording material as claimed in claim 14, wherein at least two of said aromatic ring moieties (ii) are bonded by ester linkage.

16. The thermosensitive recording material as claimed in claim 14, wherein at least two of said aromatic ring moieties (ii) are bonded by amide linkage.

17. The thermosensitive recording material as claimed in claim 14, wherein said electron-donating functional group is selected from the group consisting of hydroxyl group, alkoxyl group and sulfonyloxy group.

18. The thermosensitive recording material as claimed in claim 1, wherein said aromatic ring moieties in the molecule of said compound (A) are different.

19. The thermosensitive recording material as claimed in claim 1, wherein said electron-attracting functional group is selected from the group consisting of nitro group and ester group.

20. The thermosensitive recording material as claimed in claim 1, wherein said electron-donating functional group is selected from the group consisting of hydroxyl group, alkoxyl group and sulfonyloxy group.

21. The thermosensitive recording material as claimed in claim 1, wherein said compound having two of said aromatic ring moieties (iii) serving as said compound (A) is of formula (C):

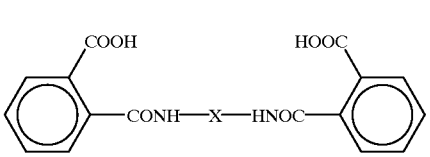

wherein X is;

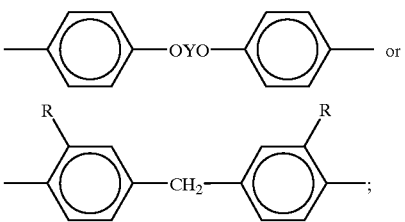

in which Y is

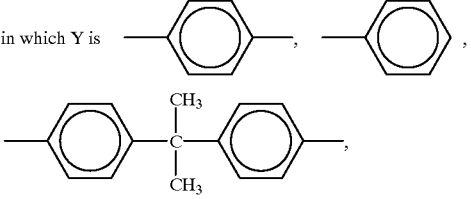

-continued

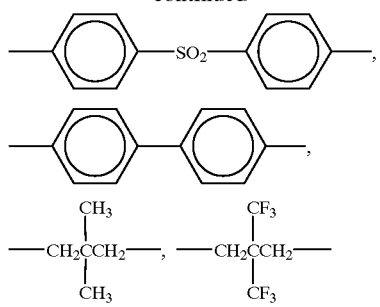

or —($C_nH_{2n}$)— in which n is an integer of 1 to 3;

and R is methyl group, ethyl group or a halogen atom.

22. The thermosensitive recording material. as claimed in claim 1, further comprising an intermediate layer which is provided between said support and said thermosensitive coloring layer.

23. The thermosensitive recording material as claimed in claim 22, wherein said intermediate layer comprises minute spherical void particles which comprise a thermoplastic resin.

* * * * *